US008524699B2

(12) United States Patent
Thede et al.

(10) Patent No.: US 8,524,699 B2
(45) Date of Patent: *Sep. 3, 2013

(54) SUBSTITUTED DIHYDROPYRAZOLONES AND USE THEREOF AS HIF-PROLYL-4-HYDROXYLASE INHIBITORS

(75) Inventors: Kai Thede, Berlin (DE); Ingo Flamme, Reichshof (DE); Felix Oehme, Wuppertal (DE); Jens-Kerim Ergüden, Wülfrath (DE); Friederike Stoll, Düsseldorf (DE); Joachim Schuhmacher, Wuppertal (DE); Hanno Wild, Wuppertal (DE); Peter Kolkhof, Wuppertal (DE); Hartmut Beck, Köln (DE); Metin Akbaba, Ratingen (DE); Mario Jeske, Solingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 494 days.

This patent is subject to a terminal disclaimer.

(21) Appl. No.: 12/447,201

(22) PCT Filed: Oct. 26, 2007

(86) PCT No.: PCT/EP2007/008977
§ 371 (c)(1),
(2), (4) Date: May 20, 2011

(87) PCT Pub. No.: WO2008/049538
PCT Pub. Date: May 2, 2008

(65) Prior Publication Data
US 2012/0264704 A1 Oct. 18, 2012

(30) Foreign Application Priority Data

Oct. 26, 2006 (DE) .......................... 10 2006 050 513

(51) Int. Cl.
*A61K 31/397* (2006.01)
*A61K 31/5377* (2006.01)
*A61K 31/501* (2006.01)
*A61K 31/4965* (2006.01)
*A61K 31/4725* (2006.01)
*A61K 31/4427* (2006.01)
*A61K 31/55* (2006.01)
*C07D 413/14* (2006.01)
*C07D 487/12* (2006.01)
*C07D 403/14* (2006.01)
*C07D 401/14* (2006.01)
*C07D 417/14* (2006.01)

(52) U.S. Cl.
USPC ............... 514/210.2; 514/211.15; 514/235.8; 514/252.03; 514/255.05; 514/256; 514/314; 514/340; 540/598; 544/114; 544/238; 544/333; 544/405; 546/167; 546/268.7; 546/275.4

(58) Field of Classification Search
USPC ................ 514/210.2, 211.15, 235.8, 252.03, 514/255.05, 256, 314, 340; 540/598; 544/114, 544/238, 333, 405; 546/167, 268.7, 275.4
See application file for complete search history.

(56) References Cited

U.S. PATENT DOCUMENTS

| 4,075,003 | A | 2/1978 | Beck et al. |
|---|---|---|---|
| 4,118,574 | A | 10/1978 | Beck et al. |
| 4,663,327 | A | 5/1987 | Sasse et al. |
| 4,698,344 | A | 10/1987 | Sasse et al. |
| 4,806,540 | A | 2/1989 | Sasse et al. |
| 2003/0083351 | A1 | 5/2003 | Almstead et al. |
| 2006/0067927 | A1 | 3/2006 | Chandrasekaran et al. |
| 2006/0160826 | A1 | 7/2006 | Ghanbari et al. |
| 2010/0093803 | A1 | 4/2010 | Thede et al. |
| 2010/0305085 | A1 | 12/2010 | Thede et al. |

FOREIGN PATENT DOCUMENTS

| CA | 1067907 | | 6/1997 |
|---|---|---|---|
| CA | 2364908 | A1 | 9/2000 |
| CA | 2608099 | A1 | 11/2006 |
| CA | 2667392 | | 2/2008 |
| DE | 2651008 | A1 | 6/1977 |
| EP | 165448 | A2 | 12/1985 |
| EP | 0183159 | | 6/1986 |
| EP | 212281 | A1 | 3/1987 |
| WO | WO-96/12706 | A1 | 5/1996 |
| WO | WO-00/51989 | A1 | 9/2000 |
| WO | 02092573 | A2 | 11/2002 |
| WO | 03/051833 | A2 | 6/2003 |
| WO | WO-03/074550 | A2 | 9/2003 |
| WO | 2004052284 | | 6/2004 |
| WO | 2004/089303 | A2 | 10/2004 |
| WO | 2004087066 | | 10/2004 |

(Continued)

OTHER PUBLICATIONS

Ri Dowell et al., "Novel Inhibitors of Prolyl 4-hydroxylase. Part 4. Pyridine-2-Carboxylic Acid Analogues with Alternative 2-Substituents", Eur. J. Med. Chem, 1993, 28, 513-516, Elsevier, Paris.
M. Eder et al (eds.).: "Allgemeine Pathologie und Pathologische Anatomie," Aufl., 33, Springer Verlag, Berlin, 1990.
R. F. Schmidt et al. (eds.): "Physiologie des Menschen," 27, Aufl., Springer Verlag, Berlin, 1997.
G. Löeffler et al, (eds.): "Biochemie und Pathobiochemie," 7, Aufl, Springer Verlag, Berlin, 2003.
M. Simons et al.: "Therapeutic Angiogenesis in Cardiovascular Disease," Nature Reviews Drug Discovery, vol. 2, Nov. 2003, pp. 1-9.
K-U Eckardt: "The Potential of Erythropoietin and Related Strategies to Stimulate Erythropoiesis," Current Opinion in Investigational Drugs, vol. 8, No. 2, 2001, pp. 1081-1085.

(Continued)

*Primary Examiner* — Samantha Shterengarts
(74) *Attorney, Agent, or Firm* — Karen B. King

(57) ABSTRACT

The present application relates to novel substituted dihydropyrazolone derivatives, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

10 Claims, No Drawings

(56) References Cited

FOREIGN PATENT DOCUMENTS

| WO | 2005030121 | 4/2005 |
|---|---|---|
| WO | 2006/0101903 | 9/2006 |
| WO | WO2006/114213 | 11/2006 |
| WO | 2007/008541 A2 | 1/2007 |

OTHER PUBLICATIONS

J. S. Berns: "Should the Target Hemoglobin for Patients with Chronic Kidney Disease Treated with Erythropoietic Replacement Therapy be Changed?," Seminars in Dialysis, vol. 18, No. 1 (Jan.-Feb. 2005), pp. 22-29.
K. Caiola et al.: "Use of Erythropoietin in Heart Failure Management," The Annals of Pharmacotherapy, vol. 38, Dec. 2004, pp. 2145-2149.
S. D. Katz: "Mechanisms and Treatment of Anemia in Chronic Heart Failure," Congestive Heart Failure, vol. 10, 2004, pp. 243-247.
G. L. Semenza: "Hypoxia-Inducible Factor 1: Oxygen Homeostasis and Disease Pathophysiology," Trends in Molecular Medicine, vol. 7, No. 8, Aug. 2001, pp. 345-350.
R. H. Wenger et al.: "Oxygen(es) and the Hypoxia-Inducible Factor-1," Biol. Chem vol. 378, Jul. 1987, pp. 609-616.
A.C.R. Epstein et al.: "Elegans EGL-9 and Mammalian Homologs Define a Family of Dioxygenases that Regulate HIF by Prolyl Hydroxylation," Cell, vol. 107, Oct. 5, 2001, pp. 43-54.
R.K. Bruick et al.: "A Conserved Family of Prolyl-4-Hydroxylases that Modify HIF," Science, vol. 294, Nov. 9, 2001, pp. 1337-1340.
M. Ivan et al.: "Biochemical purification and Pharmacological Inhibition of a Mammalian Prolyl Hydroxylase Acting on Hypoxia-Inducible Factor," Proc. Natl. Acad. Sci, U.S.A., vol. 99, No. 21, Oct. 15, 2002, pp. 13459-13464.
L. Aravind et al.: "The DNA-Repair Protein AlkB, EGL-9, and Leprecan Define New Families of 2-Oxoglutarate- and iron-dependent Dioxygenases," Genome Biology, vol. 2, No. 3, Feb. 19, 2001, pp. 1-8.
C.J. Schofield et al.: "Oxygen Sensing by HIF Hydroxylases," Nature Reviews Molecular Cell Biology, vol. 5, May 2004, pp. 343-354.
J. Büchi et al.: "Synthese und Pharmakologische Eigenschaften Einiger Pyridyl-Pyrazol-5-One," Helvetica Chemie Acta, vol. 49, 1966, pp. 272-280.
S.P. Singh et al.: "Reaction of 1-[-Hydroxy-3-Methyl-1-(2-Thiazolyl)-4-Pyrazolyl]-1,3-Butanediones with Phenyl and Heterocyclic Hydrazines: a Convienient Syntheses of 4,5-Bipyrazoles," Indian Journal of Heterocyclic Chemistry, Jul.-Sep. 1993, 3: 5-8.
J. Elguero et al.: "A 1H and 13C NMR Study of the Structure and Tautomerism of 4-Pyrazolylprazolinones," J. Heterocyclic Chem., May-Jun. 1990, 27: 865-870.
H. Barth er al.: "Konstitution und Synthese des Muscafavins," Liebigs Ann. Chem., 1981, pp. 2164-2179.
R.A. Evans er al.: "Trifluromethyl-substituted Dehydrodizepines and Cyanopyrroles form Azido-/Tetrazolo-pyridines," J. Chem. Commun., 1992, 15: 1062-1064.
F. Oehme et al.: "A Nonradioactive 96-well Plate Assay for the Detection of Hypozia-Inducible Factor Prolyl Hydroxylase Activity," Analytical Biochemistry, 2004, 330: 74-80.
F. Oehme et al.: "Overexpression of Ph-4, a Novel Putative Proline 4-Hydroxylase, Modulates Activity of Hypoxia-Inducible Transcription Factors,"Biochemical and Biophysical Research Communications, 2002, 296: 343-349.
C.A. Heid et al.: "Real Time Quantative PCR," Genome Research, 1996, 6(10): 986-994.
N. Yokoyama et al.: Synthesis and Structure-Activity Relationships of Oxamic Acid and Acetic Acid Derivatives Released to L-Thyronine,: J. Med. Chem., 1995, 38:695-707.
N. Sperber er al.: "Parasympathetic Blocking Agernt, III. N-Alkylpiperidinecarboxylic Esters," J. Am. Chem. Soc, 1959, 81: 704-709.
M.A. Meziane et al.: "A New Route to 1-Oxo-1,2-Dihydropyrimido[1,6-a]Benzimidazole-4-Carboxylates from Ethyl 2-(Benzimidazol-2-yl)-3-(Dimethylamino)Acrylate Using Solvent-Free Conditions," Synthesis, Jul. 1996, pp. 967-969.
Vippagunta et al., "Crystalline Solids," Advanced Drug Delivery Reviews, 2001, 48: 3-26.
West, "Solid Solutions," 1988, Chapter 10, pp. 358 and 365.
Ulrich, "Crystallization: 4. Crystal Characteristics," Kirk-Othmer Encyclopedia of Chemical Technology, Aug. 2002.
B. Djerrari et al.: "3-Methyl-1-(Pyridin-2-yl)-4-(1-Pyridin-2-yl-3-Methyl-1H-Pyrazol-5-yl)-2H-3-Pyrazolin-5(1HI)-one," Acta Crystallographica Section E, Structure Reports Online, 2001, E57, No. 11, pp. o1126-o1127.
Hill et al.: "Inhibition of TRPM2 channels by the antifungal agents clotrimazole and econazole," Naunyn Schmiedebergs Arch. Pharmacol, 2004, 370: 277-238, abstract only.
U.S. Appl. No. 11/919,478, filed Oct. 30, 2009.
U.S. Appl. No. 12/447,192, filed Oct. 12, 2007.
U.S. Appl. No. 12/447,207, filed Dec. 21, 2009.
U.S. Appl. No. 12/427,749, filed Apr. 22, 2009, now US Patent No. 8,067,407.

SUBSTITUTED DIHYDROPYRAZOLONES AND USE THEREOF AS HIF-PROLYL-4-HYDROXYLASE INHIBITORS

RELATED APPLICATIONS/PATENTS AND INCORPORATION BY REFERENCE

This application is a National Stage Application filed under 35 U.S.C. §371 based on International Application No. PCT/EP2007/008977, filed Oct. 17, 2007, which claims priority to German Patent Application Number 102006050513.1, filed Oct. 26, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel substituted dihydropyrazolone derivatives, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

A deficient supply of oxygen to the human organism or its components which either impairs regular functioning of the organism or its components due to its duration and/or its extent or causes its functioning to break down completely is called hypoxia. Hypoxia can be caused by a reduction in the available oxygen in the air breathed in (for example during periods at a high altitude), by disorders of external respiration (for example as a result of disturbed functioning of the lungs or obstruction of the respiratory tract), by a reduction in the cardiac output (for example in the event of cardiac insufficiency, acute right ventricular overloading with pulmonary embolism), by too low an oxygen transport capacity of the blood (for example as a result of an anemia or intoxication, for example with carbon monoxide), locally demarcated by a reduced blood flow as a result of vascular occlusions (ischemia states typically for example of the heart, the lower extremities or the brain, diabetic macro- and microangiopathy) or by an increased oxygen requirement of the tissue (for example as a result of increased muscular activity or local inflammations) [Eder, Gedigk (ed.), *Allgemeine Pathologie and pathologische Anatomie,* 33rd ed., Springer Verlag, Berlin, 1990]

The human organism is capable to a limited extent of adapting acutely and chronically to situations of reduced oxygen supply. In addition to an immediate response, which includes inter alia an increase in the cardiac output and respiratory output and a local dilation of blood vessels by vegetative-nervous control mechanisms, hypoxia brings about a change in the transcription of numerous genes. The function of the gene products here serves to compensate the oxygen deficiency. Thus, expression of several enzymes of glycolysis and glucose transporter I is enhanced, as a result of which anaerobic ATP production increases and survival of the oxygen deficiency is rendered possible [Schmidt, Thews (ed.), *Physiologie des Menschen,* 27th ed., Springer Verlag, Berlin, 1997; Löffler, Petrides (ed.), *Biochemie and Pathobiochemie,* 7th ed., Springer Verlag, Berlin, 2003].

Hypoxia furthermore leads to enhanced expression of vascular endothelial cell growth factor, VEGF, as a result of which regeneration of blood vessels (angiogenesis) is stimulated in hypoxic tissues. The blood flow through ischemic tissue is thereby improved in the long term. This counter-regulation is evidently only very inadequate in the case of various cardiovascular diseases and vascular occlusion diseases [overview in: Simons and Ware, *Therapeutic angiogenesis in cardiovascular disease,* Nat. Rev. Drug. Discov. 2 (11), 863-71 (2003)].

Furthermore, in cases of systemic hypoxia expression of the peptide hormone erythropoietin formed predominantly in the interstitial fibroblasts of the kidneys is enhanced. The formation of red blood cells in the bone marrow is thereby stimulated, and the oxygen transport capacity of the blood is therefore increased. This effect has been and is used by high-performance athletes in so-called high altitude training. A decrease in the oxygen transport capacity of the blood for example as a result of anemia after hemorrhaging usually causes an increase in erythropoietin production in the kidney. With certain forms of anemia, this regulatory mechanism may be disturbed or its normal value may be set lower. Thus for example in patients suffering from renal insufficiency, erythropoietin is indeed produced in the kidney parenchyma, but in significantly reduced amounts with respect to the oxygen transport capacity of the blood, which results in so-called renal anemia. Renal anemia in particular, but also anemias caused by tumors and HIV infection are conventionally treated by parenteral administration of recombinant human erythropoietin (rhEPO). No alternative therapy with a medicament available in oral form currently exists for this expensive therapy [overview in: Eckardt, *The potential of erythropoietin and related strategies to stimulate erythropoiesis,* Curr. Opin. Investig. Drugs 2(8), 1081-5 (2001); Berns, *Should the target hemoglobin for patients with chronic kidney disease treated with erythropoietic replacement therapy be changed?,* Semin Dial. 18 (1), 22-9 (2005)]. Recent studies demonstrate that, in addition to its erythropoiesis-increasing action, erythropoietin also has a protective (anti-apoptotic) action, which is independent thereof, on hypoxic tissue, in particular the heart and the brain. Furthermore, according to recent studies therapy with erythropoietin reduces the average severity of morbidity in patients with cardiac insufficiency [overviews in: Caiola and Cheng, *Use of erythropoietin in heart failure management,* Ann. Pharmacother. 38 (12), 2145-9 (2004); Katz, *Mechanisms and treatment of anemia in chronic heart failure,* Congest. Heart. Fail. 10 (5), 243-7 (2004)].

The genes described above which are induced by hypoxia have the common feature that the increase in their expression under hypoxia is caused by the so-called hypoxia-inducible transcription factor (HIF). HIF is a heterodimeric transcription factor which comprises an alpha and a beta subunit. Three HIF alpha isoforms have been described, of which HIF-1 alpha and HIF-2 alpha are highly homologous and are of importance for hypoxia-induced gene expression. While the beta subunit (of which 2 isoforms have been described), which is also called ARNT (aryl hydrocarbon receptor nuclear translocator), is expressed constitutively, expression of the alpha subunit depends on the oxygen content in the cell. Under normoxia, the HIF alpha protein is poly-ubiquitinized and then degraded proteasomally. Under hypoxia this degradation is inhibited, so that HIF alpha dimerizes with ARNT and can activate its target genes. The HIF dimer bonds here to so-called hypoxia-responsible elements (HRE) in the regulatory sequences of its target genes. The HRE are defined by a consensus sequence. Functional HRE have been detected in the regulatory elements of numerous hypoxia-induced genes (overviews in: Semenza, *Hypoxia-inducible factor 1: oxygen homeostasis and disease pathophysiology,* Trends Mol. Med.

7 (8), 345-50 (2001); Wenger and Gassmann, *Oxygen(es) and the hypoxia-inducible factor*-1, Biol. Chem. 378 (7), 609-16 (1997)].

The molecular mechanism on which this regulation of HIF alpha is based has been clarified by the works of several independent groups of researchers. The mechanism is conserved from species to species: HIF alpha is hydroxylated by a subclass of oxygen-dependent prolyl 4-hydroxylases, called PHD or EGLN, on two specific prolyl radicals (P402 and P564 of the human HIF-1 alpha subunit). The HIF prolyl 4-hydroxylases are iron-dependent, 2-oxoglutarate-converting dioxygenases [Epstein et al., *C. elegans EGL-9 and mammalian homologs define a family of dioxygenases that regulate HIF by prolyl hydroxylation*, Cell 107 (1), 43-54 (2001); Bruick and McKnight, *A conserved family of prolyl-4-hydroxylases that modify HIF*, Science 294 (5545), 1337-40 (2001); Ivan et al., *Biochemical purification and pharmacological inhibition of a mammalian prolyl hydroxylase acting on hypoxia-inducible factor*, Proc. Natl. Acad. Sci. U.S.A. 99 (21), 13459-64 (2002)]. The enzymes were annotated as prolyl hydroxylases for the first time in 2001 [Aravind and Koonin, *The DNA-repair protein AlkB, EGL-9, and leprecan define new families of 2-oxoglutarate- and iron-dependent dioxygenases*, Genome Biol. 2 (3), research0007.1-0007.8, Epub 2001 Feb. 19].

The pVHL tumor suppressor protein, which together with elongin B and C forms the so-called VBC complex, which adapts the HIF alpha subunit to an E3 ubiquitin ligase, bonds to the prolyl-hydroxylated HIF alpha subunit. Since the prolyl 4-hydroxylation of the HIF alpha subunit and its subsequent degradation takes place as a function of the intracellular concentration of oxygen, HIF prolyl 4-hydroxylases have also been called a cellular oxygen sensor. Three isoforms of these enzymes have been identified: EGLN1/PHD2, EGLN2/PHD1 and EGLN3/PHD3. Two of these enzymes (EGLN2/PHD1 and EGLN3/PHD3) are induced transcriptionally even under hypoxia and are possibly responsible for the lowering of the HIF alpha levels to be observed under chronic hypoxia [overview in: Schofield and Ratcliffe, *Oxygen sensing by HIF hydroxylases*, Nat. Rev. Mol. Cell. Biol. 5 (5), 343-54 (2004)].

Selective pharmacological inhibition of HIF prolyl 4-hydroxylases brings about the increase in the gene expression of HIF-dependent target genes and is therefore beneficial for the therapy of numerous disease syndromes. In the case of diseases of the cardiovascular system in particular, an improvement in the course of the disease is to be expected from induction of new blood vessels and the change in the metabolic situation of ischemic organs from aerobic to anaerobic ATP production. An improvement in the vascularization of chronic wounds promotes the healing process, especially in the case of poorly healing ulcera cruris and other chronic skin wounds. The induction of endogenous erythropoietin in certain disease forms, in particular in patients with renal anemia, is likewise a therapeutic goal to be aimed for.

The HIF prolyl 4-hydroxylase inhibitors described hitherto in the scientific literature do not meet the requirements to be imposed on a medicament. These are either competitive oxoglutarate analogs (such as for example N-oxalylglycine), which are characterized by their very low action potency, and therefore in in vivo models have as yet shown no action in the sense of an induction of HIF target genes. Or they are iron-complexing agents (chelators), such as desferroxamine, which act as non-specific inhibitors of iron-containing dioxygenases and, although they bring about an induction of the target genes, such as for example erythropoietin, in vivo, evidently counteract erythropoiesis by complexing of the available iron.

The object of the present invention is to provide novel compounds which can be employed for treatment of diseases, in particular cardiovascular and hematological diseases.

In the context of the present invention, compounds are now described which act as specific inhibitors of HIF prolyl 4-hydroxylases and on the basis of this specific action mechanism bring about in vivo, after parenteral or oral administration, the induction of HIF target genes, such as for example erythropoietin, and the biological processes thereby caused, such as for example erythropoiesis.

2-Heteroaryl-4-aryl-1,2-dihydropyrazolones having a bactericidal and/or fungicidal action are disclosed in EP 165 448 and EP 212 281. The use of 2-heteroaryl-4-aryl-1,2-dihydropyrazolones as lipoxygenase inhibitors for treatment of respiratory tract, cardiovascular and inflammatory diseases is claimed in EP 183 159. 2,4-Diphenyl-1,2-dihydropyrazolones having a herbicidal activity are described in DE 2 651 008. The preparation and pharmacological properties of certain 2-pyridyl-1,2-dihydropyrazolones are reported in *Helv. Chim. Acta* 49 (1), 272-280 (1966). WO 96/12706, WO 00/51989 and WO 03/074550 claim compounds having a dihydropyrazolone partial structure for treatment of various diseases, and WO 2006/101903 discloses hydroxy- or alkoxy-substituted bipyrazoles for treatment of neuropsychiatric disorders. Heteroaryl-substituted pyrazole derivatives for treatment of pain and various CNS diseases are furthermore described in WO 03/051833 and WO 2004/089303. WO 2006/114213 has meanwhile disclosed 2,4-dipyridyl-1,2-dihydropyrazolones as inhibitors of HIF prolyl 4-hydroxylases.

The present invention provides compounds of the general formula (I)

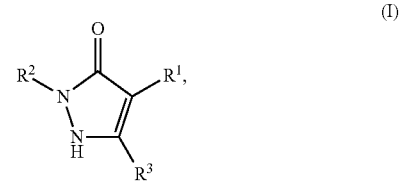

(I)

in which

R$^1$ represents a heteroaryl group of the formula

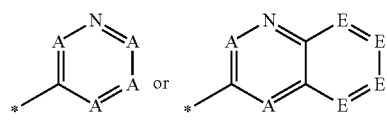

where

* represents the point of attachment to the dihydropyrazolone ring,

A in each individual occurrence represents C—R$^4$ or N, where at most two ring members A represent N at the same time, and E in each individual occurrence represents C—R$^5$ or N, where at most two ring members E represent N at the same time, $R^2$ represents a heteroaryl group of the formula

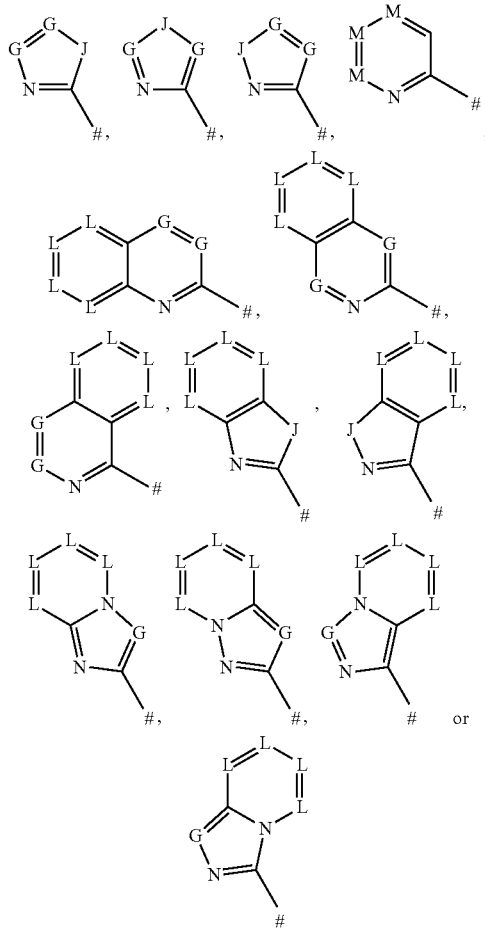

where
# represents the point of attachment to the dihydropyrazolone ring,
G in each individual occurrence represents C—$R^6$ or N,
J represents O, S or N—$R^7$,
L in each individual occurrence represents C—$R^8$ or N, where at most two ring members L represent N at the same time,
and
M in each individual occurrence represents C—$R^9$ or N, where in total one or two ring members M represent N, where
$R^4$, $R^6$, $R^8$ and $R^9$ are identical or different and in each individual case independently of one another represent hydrogen or a substituent selected from the group consisting of halogen, cyano, nitro, $(C_1-C_6)$-alkyl, $(C_3-C_7)$-cycloalkyl, 4- to 10-membered heterocycloalkyl, phenyl, 5- or 6-membered heteroaryl, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$, where
(i) $(C_1-C_6)$-alkyl for its part may be mono- to trisubstituted by identical or different radicals selected from the group consisting of halogen, cyano, oxo, $(C_3-C_7)$-cycloalkyl, 4- to 10-membered heterocycloalkyl, phenyl, 5- or 6-membered heteroaryl, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$,
where the last-mentioned cycloalkyl, heterocycloalkyl, phenyl and heteroaryl radicals for their part may in each case be substituted up to three times by identical or different substituents from the group consisting of halogen, cyano, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl,
(ii) $(C_3-C_7)$-cycloalkyl, 4- to 10-membered heterocycloalkyl, phenyl and 5- or 6-membered heteroaryl for their part may in each case be mono- to trisubstituted by identical or different radicals selected from the group consisting of $(C_1-C_6)$-alkyl, $(C_3-C_7)$-cycloalkyl, halogen, cyano, oxo, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$,
where the last-mentioned alkyl radical for its part may be substituted up to three times by identical or different substituents from the group consisting of halogen, cyano, hydroxyl, trifluoromethoxy, alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl,
(iii) $R^{10}$, $R^{11}$, $R^{12}$, $R^{14}$, $R^{15}$, $R^{18}$, $R^{20}$, $R^{22}$, $R^{25}$, $R^{26}$, $R^{27}$, $R^{29}$, $R^{30}$ and $R^{31}$ independently of one another in each individual occurrence represent a radical selected from the group consisting of hydrogen, $(C_1-C_6)$-alkyl, $(C_3-C_7)$-cycloalkyl, 4- to 7-membered heterocycloalkyl, phenyl and 5- or 6-membered heteroaryl, where
$(C_3-C_7)$-cycloalkyl, 4- to 7-membered heterocycloalkyl, phenyl and 5- or 6-membered heteroaryl for their part may in each case be substituted up to three times by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl
and
$(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl, where the last-mentioned heterocycloalkyl radical for its part may be substituted up to two times by identical or different substituents from the group consisting of $(C_1-C_4)$-alkyl, (iv) $R^{13}$, $R^{16}$, $R^{17}$, $R^{19}$, $R^{21}$, $R^{23}$, $R^{24}$, $R^{28}$ and $R^{32}$ independently of one another in each individual occurrence represent a radical selected from the group consisting of hydrogen and $(C_1-C_6)$-alkyl, where $(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and $(C_1-C_4)$-alkoxycarbonyl, and/or where (v) $R^{12}$ and $R^{13}$, $R^{15}$ and $R^{16}$, $R^{17}$ and $R^{18}$, $R^{19}$ and $R^{20}$, $R^{21}$ and $R^{22}$, $R^{22}$ and $R^{23}$, $R^{24}$ and $R^{25}$, $R^{27}$ and $R^{28}$ and also $R^{31}$ and $R^{32}$ in each case as a pair together with the atoms to which they are attached may form a 5- or 6-membered heterocycloalkyl ring which may be mono- to trisubstituted by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, $R^5$ in each individual case, independently of one another, represents hydrogen or a substituent selected from the group consisting of halogen, cyano, nitro, $(C_1-C_6)$-alkyl, trifluoromethyl, hydroxyl, $(C_1-C_6)$-alkoxy, trifluoromethoxy, amino, mono-$(C_1-C_6)$-alkylamino, alkylamino, hydroxycarbonyl and $(C_1-C_6)$-alkoxycarbonyl and $R^7$ represents hydrogen or a substituent selected from the group consisting of $(C_1-C_6)$-alkyl, $(C_3-C_7)$-cycloalkyl, 4- to 7-membered heterocycloalkyl, phenyl and 5- or 6-membered heteroaryl, where (i) $(C_1-C_6)$-alkyl for its part may be mono- to trisubstituted by identical or different radicals selected from the group consisting of halogen, cyano, oxo, $(C_3-C_7)$-cycloalkyl, 4- to 7-membered heterocycloalkyl, phenyl, 5- or 6-membered heteroaryl, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$, where the last-mentioned cycloalkyl, heterocycloalkyl, phenyl and heteroaryl radicals for their part may in each case be substituted up to three times by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, and (ii) $(C_3-C_7)$-cycloalkyl, 4- to 7-membered heterocycloalkyl, phenyl and 5- or 6-membered heteroaryl for their part may in each case be mono- to trisubstituted by identical or different radicals selected from the group consisting of $(C_1-C_6)$-alkyl, halogen, cyano, oxo, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$, where the last-mentioned alkyl radical for its part may be substituted up to three times by identical or different substituents from the group consisting of halogen, cyano, hydroxyl, trifluoromethoxy, alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl, where (a) $R^{10}$, $R^{11}$, $R^{12}$, $R^{14}$, $R^{15}$, $R^{18}$, $R^{20}$, $R^{22}$, $R^{25}$, $R^{26}$, $R^{27}$, $R^{29}$, $R^{30}$ and $R^{31}$ independently of one another in each individual occurrence represent a radical selected from the group consisting of hydrogen, $(C_1-C_6)$-alkyl, $(C_3-C_7)$-cycloalkyl, 4- to 7-membered heterocycloalkyl, phenyl and 5- or 6-membered heteroaryl, where $(C_3-C_7)$-cycloalkyl, 4- to 7-membered heterocycloalkyl, phenyl and 5- or 6-membered heteroaryl for their part may in each case be substituted up to three times by identical or different substituents from the group consisting of halogen, cyano, $(C_1-C_4$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl and $(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl, (b) $R^{13}$, $R^{16}$, $R^{17}$, $R^{19}$, $R^{21}$, $R^{23}$, $R^{24}$, $R^{28}$ and $R^{32}$ independently of one another in each individual occurrence represent a radical selected from the group consisting of hydrogen and $(C_1-C_6)$-alkyl, where $(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and $(C_1-C_4)$-alkoxycarbonyl, and/or (c) $R^{12}$ and $R^{13}$, $R^{15}$ and $R^{16}$, $R^{17}$ and $R^{18}$, $R^{19}$ and $R^{20}$, $R^{21}$ and $R^{22}$, $R^{22}$ and $R^{23}$, $R^{24}$ and $R^{25}$, $R^{27}$ and $R^{28}$ and also $R^{31}$ and $R^{32}$ in each case as a pair together with the atoms to which they are attached may form a 5- or 6-membered heterocycloalkyl ring which may be mono- to trisubstituted by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, and $R^3$ represents hydrogen, $(C_1-C_6)$-alkyl or $(C_3-C_7)$-cycloalkyl, and salts, solvates and solvates of the salts thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures. The stereoisomerically uniform constituents can be isolated from such mixtures of enantiomers and/or diastereomers in a known manner.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, such as, by way of example and preferably, alkali metal salts (for example sodium and potassium salts), alkaline earth metal salts (for example calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" includes compounds which themselves can be biologically active or inactive, but are converted (for example metabolically or hydrolytically) into compounds according to the invention during their dwell time in the body.

In the context of the present invention, the substituents have the following meaning, unless specified otherwise:

$(C_1-C_6)$-Alkyl and $(C_1-C_4)$-alkyl in the context of the invention represent a straight-chain or branched alkyl radical having 1 to 6 or, respectively, 1 to 4 carbon atoms. A straight-chain or branched alkyl radical having 1 to 4 carbon atoms is preferred. There may be mentioned by way of example and preferably: methyl, ethyl, n-propyl, isopropyl, n-butyl, isobutyl, sec-butyl, tert-butyl, 1-ethylpropyl, n-pentyl and n-hexyl.

$(C_1-C_6)$-Alkoxy and $(C_1-C_4)$-alkoxy in the context of the invention represent a straight-chain or branched alkoxy radical having 1 to 6 or, respectively, 1 to 4 carbon atoms. A straight-chain or branched alkoxy radical having 1 to 4 carbon atoms is preferred. There may be mentioned by way of example and preferably: methoxy, ethoxy, n-propoxy, isopropoxy, n-butoxy, tert-butoxy, n-pentoxy and n-hexoxy.

Mono-$(C_1-C_6)$-alkylamino and mono-$(C_1-C_4)$-alkylamino in the context of the invention represent an amino group with a straight-chain or branched alkyl substituent which contains 1 to 6 or, respectively, 1 to 4 carbon atoms. A straight-chain or branched monoalkylamino radical having 1 to 4 carbon atoms is preferred. There may be mentioned by way of example and preferably: methylamino, ethylamino, n-propylamino, isopropylamino, n-butylamino, tert-butylamino, n-pentylamino and n-hexylamino.

Di-$(C_1-C_6)$-alkylamino and di-$(C_1-C_4)$-alkylamino in the context of the invention represent an amino group with two identical or different straight-chain or branched alkyl substituents which each contain 1 to 6 or, respectively, 1 to 4 carbon atoms. Straight-chain or branched dialkylamino radicals having in each case 1 to 4 carbon atoms are preferred. There may be mentioned by way of example and preferably: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methyl-amino.

$(C_1-C_6)$-Alkoxycarbonyl and $(C_1-C_4)$-alkoxycarbonyl in the context of the invention represent a straight-chain or branched alkoxy radical having 1 to 6 or, respectively, 1 to 4 carbon atoms which is linked via a carbonyl group. A straight-chain or branched alkoxycarbonyl radical having 1 to 4 carbon atoms in the alkoxy group is preferred. There may be mentioned by way of example and preferably: methoxycarbonyl, ethoxycarbonyl, n-propoxycarbonyl, isopropoxycarbonyl, n-butoxycarbonyl and tert-butoxycarbonyl.

$(C_3-C_7)$-Cycloalkyl and $(C_3-C_6)$-cycloalkyl in the context of the invention represent a monocyclic, saturated carbocyclic radical having 3 to 7 or, respectively, 3 to 6 ring carbon atoms. There may be mentioned by way of example and preferably: cyclopropyl, cyclobutyl, cyclopentyl, cyclohexyl and cycloheptyl.

4- to 10-membered heterocycloalkyl in the context of the invention represents a mono- or optionally bicyclic heterocycle which is saturated or contains a double bond and has a total of 4 to 10 ring atoms, which contains one or two ring heteroatoms from the group consisting of N, O and S and which is attached via a ring carbon atom or, if appropriate, via a ring nitrogen atom. There may be mentioned by way of example: azetidinyl, oxetanyl, thietanyl, pyrrolidinyl, pyrrolinyl, pyrazolidinyl, dihydropyrazolyl, tetrahydrofuranyl, thiolanyl, 1,3-oxazolidinyl, 1,3-thiazolidinyl, piperidinyl, tetrahydropyridyl, piperazinyl, tetrahydropyranyl, dihydropyranyl, tetrahydrothio-pyranyl, 1,3-dioxanyl, 1,4-dioxanyl, morpholinyl, thiomorpholinyl, hexahydroazepinyl, hexahydro-1,4-diazepinyl, octahydroazocinyl, octahydropyrrolo[3,4-b]pyrrolyl, octahydroisoindolyl, octa-hydropyrrolo[3,4-b]pyridyl, hexahydropyrrolo[3,4-c]pyridyl, octahydropyrrolo[1,2-a]pyrazinyl, decahydroisoquinolinyl, octahydropyrido[1,2-a]pyrazinyl, 7-azabicyclo[2.2.1]heptanyl, 3-azabicyclo[3.2.0]heptanyl, 3-azabicyclo[3.2.1]octanyl, 8-azabicyclo[3.2.1]octanyl, 8-oxa-3-azabi-cyclo[3.2.1]octanyl. Preference in the context of the invention is given to a monocyclic saturated 4- to 7-membered heterocycloalkyl radical having a total of 4 to 7 ring atoms which contains one or two ring heteroatoms from the group consisting of N, O and S and is attached via a ring carbon atom or, if appropriate, a ring nitrogen atom. There may be mentioned by way of example: azeti-dinyl, oxetanyl, thietanyl, pyrrolidinyl, pyrazolidinyl, tetrahydrofuranyl, thiolanyl, 1,3-oxa-zolidinyl, piperidinyl, piperazinyl, tetrahydropyranyl, tetrahydrothiopyranyl, 1,3-dioxanyl, 1,4-dioxanyl, morpholinyl, thiomorpholinyl, hexahydroazepinyl, hexahydro-1,4-diazepinyl. Particular preference is given to a 4- to 6-membered heterocycloalkyl radical which has a total of 4 to 6 ring atoms and which contains one or two ring heteroatoms from the group consisting of N and O, such as, for example, pyrrolidinyl, tetrahydrofuranyl, piperidinyl, piperazinyl, tetrahydropyranyl and morpholinyl.

5- or 6-membered heteroaryl in the context of the invention represents an aromatic heterocyclic radical (heteroaromatic) having a total of 5 or, respectively, 6 ring atoms which contains up to four identical or different ring heteroatoms from the group consisting of N, O and S and is linked via a ring carbon atom or optionally via a ring nitrogen atom. There may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl. 5- or 6-membered heteroaryl radicals having up to three ring heteroatoms from the group consisting of N, O and S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl and pyrazinyl, are preferred.

Halogen in the context of the invention includes fluorine, chlorine, bromine and iodine. Fluorine, chlorine and bromine are preferred, and fluorine and chlorine are particularly preferred.

If radicals in the compounds according to the invention are substituted, the radicals can be mono- or polysubstituted, unless specified otherwise. In the context of the present invention, for all the radicals which occur several times, the meaning thereof is independent of one another. Substitution by one, two or three identical or different substituents is preferred. Substitution by one or two identical or different substituents is particularly preferred.

Preference in the context of the present invention is given to compounds of the formula (I) in which
$R^1$ represents a heteroaryl group of the formula

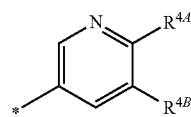

where
* represents the point of attachment to the dihydropyrazolone ring
and
$R^{4A}$ and $R^{4B}$ are identical or different and independently of one another represent hydrogen or a substituent selected from the group consisting of fluorine, chlorine, bromine, cyano, $(C_1-C_6)$-alkyl, hydroxyl, $(C_1-C_6)$-alkoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl, where the $(C_1-C_6)$-alkyl radical mentioned for its part may be substituted up to three times by identical or different substituents from the group consisting of fluorine, chlorine, bromine, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and $(C_1-C_4)$-alkoxycarbonyl, $R^2$ represents a heteroaryl group of the formula

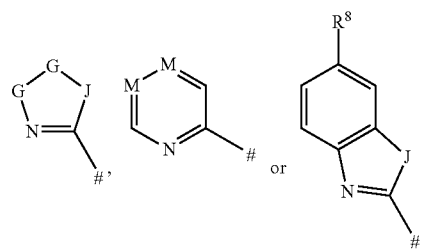

where
# represents the point of attachment to the dihydropyrazolone ring,
G represents in each case C—$R^6$ or N, where not more than one of the two ring members G represents N,
J represents O or S,
M represents in each case C—$R^9$ or N, where one of the two ring members M represents N and the other represents C—$R^9$,
where
$R^6$ and $R^9$ in each individual case independently of one another represent hydrogen or a substituent selected from the group consisting of fluorine, chlorine, bromine, cyano, $(C_3-C_6)$-cycloalkyl, 4- to 6-membered heterocycloalkyl, phenyl, 5- or 6-membered heteroaryl, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$OR^{29}$ and —$NR^{31}R^{32}$, where
(i) $(C_1-C_6)$-alkyl for its part may be mono- to trisubstituted by identical or different radicals selected from the group consisting of fluorine, chlorine, bromine, cyano, $(C_3-C_6)$-cycloalkyl, 4- to 6-membered heterocycloalkyl, phenyl, 5- or 6-membered heteroaryl, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)— and —$NR^{31}R^{32}$,
where the last-mentioned cycloalkyl, heterocycloalkyl, phenyl and heteroaryl radicals for their part may in each case be substituted up to two times by identical or different substituents from the group consisting of fluorine, chlorine, bromine, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl,
(ii) $(C_3-C_6)$-cycloalkyl, 4- to 6-membered heterocycloalkyl, phenyl and 5- or 6-membered heteroaryl for their part may in each case be mono- or disubstituted by identical or different substituents from the group consisting of fluorine, chlorine, bromine, cyano, $(C_1-C_4)$-alkyl, trifluoromethyl, hydroxyl, $(C_1-C_4)$-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, (iii) $R^{11}$, $R^{12}$, $R^{14}$, $R^{15}$, $R^{18}$, $R^{20}$, $R^{22}$, $R^{25}$, $R^{29}$ and $R^{31}$ independently of one another in each individual occurrence represent a radical selected from the group consisting of hydrogen, ($C_1$-$C_6$)-alkyl, ($C_3$-$C_6$)-cycloalkyl, 4- to 6-membered heterocycloalkyl, phenyl and 5- or 6-membered heteroaryl, where ($C_3$-$C_6$)-cycloalkyl, 4- to 6-membered heterocycloalkyl, phenyl and 5- or 6-membered heteroaryl for their part may in each case be substituted up to three times by identical or different substituents from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, alkylamino, hydroxycarbonyl and ($C_1$-$C_4$)-alkoxycarbonyl and ($C_1$-$C_6$)-alkyl may be mono- to trisubstituted by identical or different substituents from the group consisting of fluorine, chlorine, bromine, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and 5- or 6-membered heteroaryl, (iv) $R^{13}$, $R^{16}$, $R^{17}$, $R^{19}$, $R^{21}$, $R^{23}$, $R^{24}$ and $R^{32}$ independently of one another in each individual occurrence represent a radical selected from the group consisting of hydrogen and ($C_1$-$C_6$)-alkyl, where ($C_1$-$C_6$)-alkyl may be mono- or disubstituted by identical or different substituents from the group consisting of fluorine, chlorine, bromine, cyano, hydroxyl, trifluoromethoxy, ($C_1$-$C_4$)-alkoxy, amino, mono-($C_1$-$C_4$)-alkylamino, hydroxycarbonyl and ($C_1$-$C_4$)-alkoxycarbonyl, and/or where (v) $R^{12}$ and $R^{13}$, $R^{15}$ and $R^{16}$, $R^{17}$ and $R^{18}$, $R^{19}$ and $R^{20}$, $R^{21}$ and $R^{22}$, $R^{22}$ and $R^{23}$, $R^{24}$ and $R^{25}$ and also $R^{31}$ and $R^{32}$ in each case as a pair together with the atoms to which they are attached may form a 5- or 6-membered heterocycloalkyl ring which may be mono- or disubstituted by identical or different substituents from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, and $R^8$ represents hydrogen or a substituent selected from the group consisting of fluorine, chlorine, bromine, cyano, ($C_1$-$C_6$)-alkyl, hydroxyl, ($C_1$-$C_6$)-alkoxy, trifluoromethoxy, amino, mono-($C_1$-$C_6$)-alkylamino, di-($C_1$-$C_6$)-alkylamino, hydroxycarbonyl and ($C_1$-$C_6$)-alkoxycarbonyl, and $R^3$ represents hydrogen or methyl, and salts, solvates and solvates of the salts thereof.

Particular preference in the context of the present invention is given to compounds of the formula (I) in which $R^1$ represents a heteroaryl group of the formula

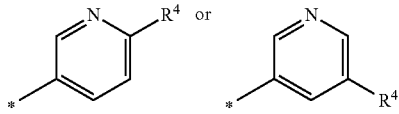

where

* represents the point of attachment to the dihydropyrazolone ring and $R^4$ represents hydrogen, fluorine, chlorine, bromine, cyano, ($C_1$-$C_4$)-alkyl, trifluoromethyl, hydroxymethyl, ($C_1$-$C_4$)-alkoxy, trifluoromethoxy, hydroxycarbonyl or ($C_1$-$C_4$)-alkoxycarbonyl, $R^2$ represents a heteroaryl group of the formula

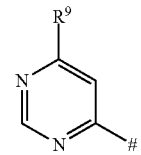

where

\# represents the point of attachment to the dihydropyrazolone ring and $R^9$ represents hydrogen, fluorine, chlorine, bromine, cyano, ($C_1$-$C_4$)-alkyl, trifluoromethyl, hydroxyl, ($C_1$-$C_4$)-alkoxy, trifluoromethoxy, amino, mono-($C_1$-$C_4$)-alkylamino, di-($C_1$-$C_4$)-alkylamino, hydroxycarbonyl, ($C_1$-$C_4$)-alkoxycarbonyl, 4- to 6-membered heterocycloalkyl, phenyl or 5- or 6-membered heteroaryl, where ($C_1$-$C_4$)-alkyl for its part may be substituted by hydroxyl, ($C_1$-$C_4$)-alkoxy or amino and 4- to 6-membered heterocycloalkyl, phenyl and 5- or 6-membered heteroaryl for their part may in each case be mono- or disubstituted by identical or different substituents from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, and $R^3$ represents hydrogen, and salts, solvates and solvates of the salts thereof.

Particular preference in the context of the present invention is also given to compounds of the formula (I) in which $R^1$ represents a heteroaryl group of the formula

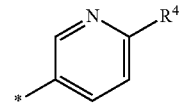

where
* represents the point of attachment to the dihydropyrazolone ring and $R^4$ represents hydrogen, fluorine, chlorine, bromine, cyano, ($C_1$-$C_4$)-alkyl, trifluoromethyl, hydroxymethyl, ($C_1$-$C_4$)-alkoxy, trifluoromethoxy, hydroxycarbonyl or ($C_1$-$C_4$)-alkoxycarbonyl, $R^2$ represents a heteroaryl group of the formula

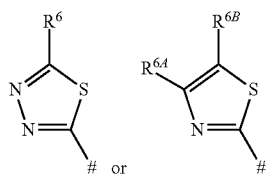

where

\# represents the point of attachment to the dihydropyrazolone ring and $R^6$, $R^{6A}$ and $R^{6B}$ are identical or different and independently of one another represent hydrogen or a substituent selected from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, amino, mono-($C_1$-$C_4$)-alkylamino, di-($C_1$-$C_4$)-alkylamino, hydroxycarbonyl, ($C_1$-$C_4$)-alkoxycarbonyl, 4- to 6-membered heterocycloalkyl, phenyl and 5- or 6-membered heteroaryl, where ($C_1$-$C_4$)-alkyl for its part may be substituted by hydroxyl, ($C_1$-$C_4$)-alkoxy or amino and 4- to 6-membered heterocycloalkyl, phenyl and 5- or 6-membered heteroaryl for their part may in each case be mono- or disubstituted by identical or different substituents from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, and $R^3$ represents hydrogen, and salts, solvates and solvates of the salts thereof.

The radical definitions given in detail in the particular combinations or preferred combinations of radicals are also replaced as desired by radical definitions of other combinations, independently of the particular radical combinations given.

Combinations of two or more of the abovementioned preferred ranges are very particularly preferred.

The 1,2-dihydropyrazol-3-one derivatives of the formula (I) according to the invention can also be in the tautomeric 1H-pyrazol-5-ol form (I') (see Scheme 1 below); the two tautomeric forms are expressly incorporated into the present invention.

Scheme 1

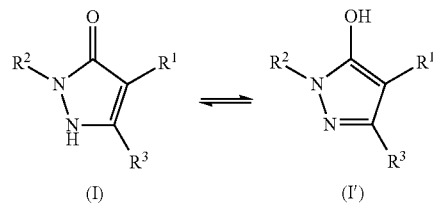

The invention also provides a process for the preparation of the compounds of the formula (I) according to the invention, characterized in that a compound of the formula (II)

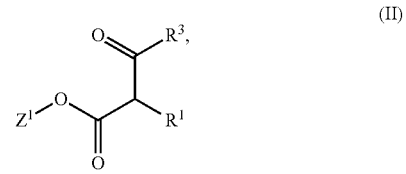

in which $R^1$ and $R^3$ have the meanings given above and $Z^1$ represents methyl or ethyl, is reacted in an inert solvent, if appropriate in the presence of an acid, with a compound of the formula (III)

in which $R^2$ has the meaning given above, to give compounds of the formula (IV)

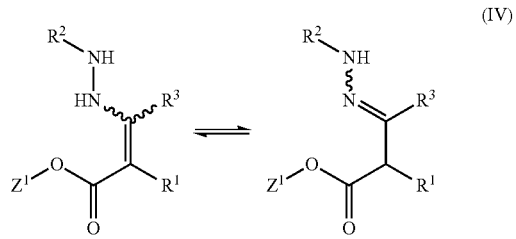

in which $Z^1$, $R^1$, $R^2$ and $R^3$ have the meanings given above, which, already under these reaction conditions or in a subsequent reaction step under the action of a base, cyclize to the compounds of the formula (I), and the compounds of the formula (I) are, if appropriate with the appropriate (i) solvents and/or (ii) bases or acids, converted into their solvates, salts and/or solvates of the salts.

The compounds of the formula (I) according to the invention in which $R^3$ represents hydrogen can also be prepared by initially condensing a compound of the formula (V)

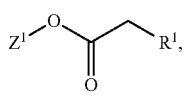

in which $Z^1$ and $R^1$ have the meanings given above, with a compound of the formula (VI)

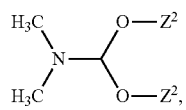

in which
$Z^2$ represents methyl or ethyl,
to give compounds of the formula (VII)

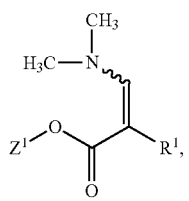

in which $Z^1$ and $R^1$ have the meanings given above, and then reacting it in the presence of an acid with a compound of the formula (III) to give compounds of the formula (IV-A)

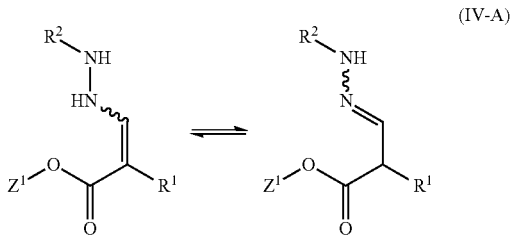

in which $Z^1$, $R^1$ and $R^2$ have the meanings given above, which, already under these reaction conditions or in a subsequent reaction step under the action of a base, cyclize to the compounds of the formula (I) in which $R^3$ represents hydrogen.

Further compounds according to the invention can optionally also be prepared by conversions of functional groups of individual substituents, in particular those listed under $R^1$ and $R^2$, starting from the compounds of the formula (I) obtained by the above processes. These conversions are carried out by conventional methods known to the person skilled in the art and include, for example, reactions such as nucleophilic or electrophilic substitution, oxidation, reduction, hydrogenation, transition metal-catalyzed coupling reactions, alkylation, acylation, amination, esterification, ester cleavage, etherification, ether cleavage, formation of carboxamides, sulfonamides, carbamates and ureas, and the introduction and removal of temporary protective groups.

Suitable inert solvents for the process steps (II)+(III)→(IV), (IV)→(I), (VII)+(III)→(IV-A) and (IV-A)→(I) are, in particular, ethers, such as diethyl ether, methyl tert-butyl ether, 1,2-dimethoxyethane, tetrahydrofuran and dioxane, or alcohols, such as methanol, ethanol, n-propanol, iso-propanol, n-butanol and tert-butanol. Methanol, ethanol tetrahydrofuran or mixtures of these solvents are preferably employed.

The process step (V)+(VI)→(VII) is preferably carried out in dimethylformamide as a solvent or in the presence of an excess of (VI) without a further solvent. The reaction can also optionally advantageously be carried out under microwave irradiation. The reaction in general takes place in a temperature range of from +20° C. to +150° C., preferably at +80° C. to +120° C. [cf. also J. P. Bazureau et al., *Synthesis* 1998, 967; ibid. 2001 (4), 581].

Process steps (II)+(III)→(IV) and (VII)+(III)→(IV-A) can optionally advantageously be carried out with the addition of an acid. Conventional inorganic or organic acids are suitable for this, such as, for example, hydrogen chloride, acetic acid, trifluoroacetic acid, methanesulfonic acid, p-toluenesulfonic acid or camphor-10-sulfonic acid. Acetic acid or, in particular, camphor-10-sulfonic acid or p-toluenesulfonic acid are preferably used.

The reaction (II)+(III)→(IV) is in general carried out in a temperature range of from 0° C. to +100° C., preferably at +10° C. to +50° C. The reaction (VII)+(III)→(IVA) is in general carried out in a temperature range of from +20° C. to +120° C., preferably at +50° C. to +100° C.

The process sequences (II)+(III)→(IV)→(I) and (VII)+(III)→(IV-A)→(I) can be carried out under a two-stage reaction procedure or as a one-pot reaction, without isolation of the intermediate stage (IV) or, respectively, (IV-A). For the latter variant, reaction of the components under microwave irradiation is suitable in particular; the reaction here is in general carried out in a temperature range of from +50° C. to +200° C., preferably at +100° C. to +180° C.

In some cases a cyclization to (I) also already occurs even during preparation of (IV) or, respectively, (IV-A); the cyclization can then optionally be brought to completion by in situ treatment of the reaction mixture with a base.

Conventional inorganic or organic bases are suitable as the base for such a separate cyclization step (IV)→(I) or (IV-A)→(I). These include, in particular, alkali metal hydroxides, such as, for example, sodium or potassium hydroxide, alkali metal or alkaline earth metal carbonates, such as sodium, potassium, calcium or cesium carbonate, alkali metal alcoholates, such as sodium or potassium methanolate, sodium or potassium ethanolate or sodium or potassium tert-butylate, or alkali metal hydrides, such as sodium hydride. Sodium methanolate or ethanolate are preferably used.

The base-induced reaction (IV)→(I) or (IV-A)→(I) is in general carried out in a temperature range of from 0° C. to +60° C., preferably at 0° C. to +30° C.

All the process steps can be carried out under atmospheric, elevated or reduced pressure (e.g. from 0.5 to 5 bar). In general, atmospheric pressure is applied.

The compounds of the formula (II) can be prepared by conventional methods from the literature for C-acylation of carboxylic acid esters from compounds of the formula (V). The compounds of the formulae (III), (V) and (VI) are commercially obtainable or known from the literature or can be prepared analogously to processes described in the literature.

The preparation of the compounds according to the invention can be illustrated by reaction scheme 2 below:

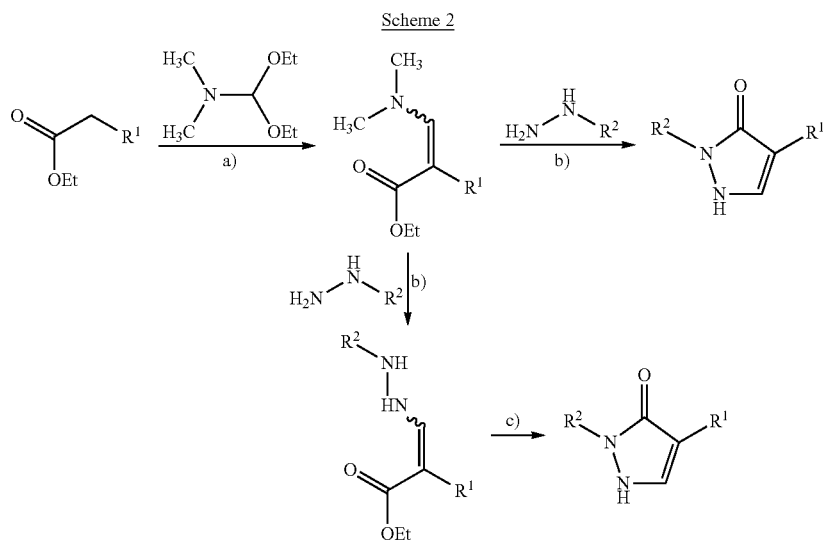

[a]: DMF, 16 h, +100° C.; b): ethanol, cat. camphor-10-sulfonic acid, +78° C.; c): NaOEt, ethanol, 1 h, RT].

The compounds according to the invention show an unforeseeable, valuable pharmacological action spectrum. They are therefore suitable for use as medicaments for treatment and/or prophylaxis of diseases in humans and animals.

The compounds according to the invention are distinguished as specific inhibitors of HIF prolyl 4-hydroxylases.

On the basis of their pharmacological properties, the compounds according to the invention can be employed for treatment and/or prophylaxis of cardiovascular diseases, in particular cardiac insufficiency, coronary heart disease, angina pectoris, myocardial infarction, stroke, arteriosclerosis, essential, pulmonary and malignant hypertension and peripheral arterial occlusive disease.

The compounds according to the invention are furthermore suitable for treatment and/or prophylaxis of blood formation disorders, such as for example idiopathic anemias, renal anemia and anemias accompanying a tumor disease (in particular an anemia induced by chemotherapy), an infection (in particular HIV infection) or another inflammatory disease, such as for example rheumatoid arthritis. The compounds according to the invention are moreover suitable for supporting treatment of anemias as a result of blood loss, iron deficiency anemia, vitamin deficiency anemia (for example as a result of vitamin B12 deficiency or as a result of folic acid deficiency), hypoplastic and aplastic anemia or hemolytic anemia, or for supporting treatment of anemias as a result of iron utilization disorders (sideroachrestic anemia) or anemias as a result of other endocrine disorders (for example hypothyroidosis).

The compounds are furthermore suitable for increasing the hematocrit with the aim of obtaining blood for autodonation of blood before operations.

The compounds according to the invention can moreover be used for treatment and/or prophylaxis of operation-related states of ischemia and their sequelae after surgical interventions, in particular interventions on the heart using a heart-lung machine (for example bypass operations, heart valve implants), interventions on the carotid arteries, interventions on the aorta and interventions with instrumental opening or penetration of the skull cap. The compounds are furthermore suitable for general treatment and/or prophylaxis in the event of surgical interventions with the aim of accelerating wound healing and shortening the reconvalescence time.

The compounds are moreover suitable for treatment and prophylaxis of sequelae of acute and protracted ischemic states of the brain (for example stroke, birth asphyxia).

The compounds can furthermore be employed for treatment and/or prophylaxis of cancer and for treatment and/or prophylaxis of an impairment in the state of health occurring in the course of treatment of cancer, in particular after therapy with cytostatics, antibiotics and irradiations.

The compounds are furthermore suitable for treatment and/or prophylaxis of diseases of the rheumatic type and other diseases forms to be counted as autoimmune diseases, and in particular for treatment and/or prophylaxis of an impairment in the state of health occurring in the course of medicamentous treatment of such diseases.

The compounds according to the invention can moreover be employed for treatment and/or prophylaxis of diseases of the eye (for example glaucoma), the brain (for example Parkinson's disease, Alzheimer's disease, dementia, chronic pain sensation), of chronic kidney diseases, renal insufficiency and acute renal failure and for promoting wound healing.

The compounds are moreover suitable for treatment and/or prophylaxis of general physical weakness, up to cachexia, in particular occurring to an increased extent in the elderly.

The compounds are furthermore suitable for treatment and/or prophylaxis of sexual dysfunction.

The compounds are moreover suitable for treatment and/or prophylaxis of diabetes mellitus and its sequelae, such as for example diabetic macro- and microangiopathy, diabetic nephropathy and neuropathy.

The compounds according to the invention are moreover suitable for treatment and/or prophylaxis of fibrotic diseases for example of the heart, the lungs and the liver.

In particular, the compounds according to the invention are also suitable for prophylaxis and treatment of retinopathy in premature babies (retinopathia prematurorum).

The present invention moreover provides the use of the compounds according to the invention for treatment and/or prevention of diseases, in particular the abovementioned diseases.

The present invention moreover provides the use of the compounds according to the invention for the preparation of a medicament for treatment and/or prevention of diseases, in particular the abovementioned diseases.

The present invention moreover provides a method for treatment and/or prevention of diseases, in particular the abovementioned diseases, using an effective amount of at least one of the compounds according to the invention.

The compounds according to the invention can be employed by themselves or, if required, in combination with other active compounds. The present invention moreover provides medicaments comprising at least one of the compounds according to the invention and one or more further active compounds, in particular for treatment and/or prevention of the abovementioned diseases. Suitable active compounds in combination which may be mentioned by way of example and preferably are: ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, digitalis (digoxin) derivatives, tumor chemotherapeutics and antibiotics.

In a preferred embodiment of the invention, the compounds according to the invention are administered in combination with an ACE inhibitor, such as, by way of example and preferably, enalapril, captopril, lisinopril, ramipril, delapril, fosinopril, quinoprol, perindopril or trandopril.

In a preferred embodiment of the invention, the compounds according to the invention are administered in combination with an angiotensin AII antagonist, such as, by way of example and preferably, losartan, candesartan, valsartan, telmisartan or embusartan.

In a preferred embodiment of the invention, the compounds according to the invention are administered in combination with a beta receptor blocker, such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a calcium antagonist, such as, by way of example and preferably, nifedipine, amlopidine, verapamil or diltiazem.

In a preferred embodiment of the invention, the compounds according to the invention are administered in combination with a phosphodiesterase (PDE) inhibitor, such as, by way of example and preferably, milrinone, aminone, pimobendan, cilostazol, sildenafil, vardenafil or tadalafil.

In a preferred embodiment of the invention, the compounds according to the invention are administered in combination with a mineralocorticoid receptor antagonist, such as, by way of example and preferably, spironolactone, eplerenone, canrenone or potassium canrenoate.

In a preferred embodiment of the invention the compounds according to the invention are administered in combination with a diuretic, such as, by way of example and preferably, furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerin, isosorbide, mannitol, amiloride or triamterene.

In a preferred embodiment of the invention, the compounds according to the invention are administered in combination with an HMG-CoA reductase inhibitor from the class of statins, such as, by way of example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a tumor chemotherapeutic, by way of example and preferably from the group consisting of platinum complexes, such as for example cisplatin and carboplatin, the alkylating agents, such as for example cyclophosphamide and chlorambucil, the antimetabolites, such as for example 5-fluorouracil and methotrexate, the topoisomerase inhibitors, such as for example etoposide and camptothecin, the antibiotics, such as for example doxorubicin and daunorubicin, or the kinase inhibitors, such as for example sorafenib and sunitinib.

In a preferred embodiment of the invention, the compounds according to the invention are administered in combination with an antibiotic, by way of example and preferably from the group consisting of penicillins, cephalosporins or quinolones, such as for example ciprofloxacin and moxifloxacin.

The present invention moreover provides medicaments which comprise at least one compound according to the invention, conventionally together with one or more inert, non-toxic, pharmaceutically suitable auxiliaries, and the use thereof for the abovementioned purposes.

The compounds according to the invention can act systemically and/or locally. They can be administered in a suitable manner for this purpose, such as for example orally, parenterally, pulmonally, nasally, sublingually, lingually, buccally, rectally, dermally, transdermally, conjunctivally, otically or as an implant or stent.

The compounds according to the invention can be administered in suitable administration forms for these administration routes.

Administration forms which function according to the prior art, release the compounds according to the invention rapidly and/or in a modified manner and comprise the compounds according to the invention in crystalline and/or amorphized and/or dissolved form are suitable for oral administration, such as for example tablets (non-coated or coated tablets, for example coatings which are resistant to gastric juice or dissolve in a delayed manner or are insoluble and control the release of the compound according to the invention), tablets or films/oblates, films/lyophilisates or capsules which disintegrate rapidly in the oral cavity (for example hard or soft gelatin capsules), sugar-coated tablets, granules, pellets, powders, emulsions, suspensions, aerosols or solutions.

Parenteral administration can be effected with bypassing of an absorption step (for example intravenously, intraarterially, intracardially, intraspinally or intralumbally) or with inclusion of an absorption (for example intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilisates or sterile powders.

For the other administration routes, inhalation medicament forms (inter alia powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (for example patches), milk, pastes, foams, sprinkling powders, implants or stents are suitable, for example.

Oral and parenteral administration are preferred, in particular oral and intravenous administration.

The compounds according to the invention can be converted into the administration forms mentioned. This can be effected in a manner known per se by mixing with inert, non-toxic, pharmaceutically suitable auxiliaries. These auxiliaries include inter alia carrier substances (for example microcrystalline cellulose, lactose, mannitol), solvents (for example liquid polyethylene glycols), emulsifiers and dispersing or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), dyestuffs (for example inorganic pigments, such as, for example, iron oxides) and flavor and/or smell correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, depending on the body weight, administration route, individual behavior toward the active compound, nature of the formulation and point of time or interval at which administration takes place. Thus in some cases it may be sufficient to manage with less than the abovementioned minimum amount, while in other cases the upper limit mentioned must be exceeded. In the case where relatively large amounts are administered, it may be advisable to distribute these into several individual doses over the day.

The following embodiment examples illustrate the invention. The invention is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

A. EXAMPLES

Abbreviations and Acronyms aq. aqueous solution
cat. catalytic
d day(s)
DCI direct chemical ionization (in MS)
DMF dimethylformamide
DMSO dimethyl sulfoxide
EI electron impact ionization (in MS)
ESI electrospray ionization (in MS)
Et ethyl
h hour(s)
HPLC high pressure, high performance liquid chromatography
conc. concentrated
LC-MS liquid chromatography-coupled mass spectroscopy
Meth. method
min minute(s)
MS mass spectroscopy
NMR nuclear magnetic resonance spectroscopy
rac racemic
$R_t$ retention time (in HPLC)
RT room temperature
TFA trifluoroacetic acid
THF tetrahydrofuran LC-MS, GC-MS and HPLC Methods:
Method 1:
Instrument: Micromass Platform LCZ with HPLC Agilent Series 1100; column: Thermo Hypersil GOLD 3µ, 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.
Method 2:
MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 3:
Instrument: Micromass Quattro LCZ with HPLC Agilent Series 1100; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.
Method 4:
MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 5:
MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min 2.5 min/3.0 min/4.5 min 2 ml/min; oven: 50° C.; UV detection: 210 nm.
Method 6:
MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A 4.01 min 90% A; flow rate: 2 ml/min; oven: 50° C.; UV detection: 210 nm.
Method 7:
Instrument: Micromass Quattro Micro MS with HPLC Agilent Series 1100; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
Method 8:
MS instrument type: Waters ZQ; HPLC instrument type: Agilent 1100 Series; UV DAD; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A; flow rate: 2.5 ml/min; oven: 55° C.; UV detection: 210 nm.
Method 9:

Instrument: Micromass QuattroPremier with Waters HPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A 0.1 min 90% A→1.5 min 10% A→2.2 min 10% A; flow rate: 0.33 ml/min; oven: 50° C.; UV detection: 210 nm.
Method 10:

Instrument: Micromass QuattroPremier with Waters HPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 100% A→0.1 min 100% A→1.5 min 10% A→2.2 min 10% A; flow rate: 0.33 ml/min; oven: 50° C.; UV detection: 210 nm.
Method 11:

MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.
Method 12:

Instrument: Micromass Quattro LCZ with HPLC Agilent Series 1100; column: Phenomenex Synergi 2.5µ MAX-RP 100A Mercury 20 mm×4 mm; mobile phase A: 1 l of water+ 0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.
Method 13 (Preparative LC-MS):

Instrument MS: Waters ZQ 2000; Instrument HPLC: Agilent 1100, 2-column system; autosampler: HTC PAL; column: YMC-ODS-AQ, 50 mm×4.6 mm, 3.0 µm; mobile phase A: water+0.1% formic acid, mobile phase B: acetonitrile+ 0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Starting Materials and Intermediates

Example 1A

Ethyl (6-chloropyridin-3-yl)acetate

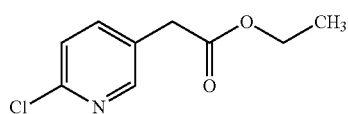

22.0 g (144 mmol) of (6-chloropyridin-3-yl)acetonitrile are added to a mixture of 270 ml of ethanol and 101 ml conc. sulfuric acid, and the mixture is stirred under reflux for 24 h. With stirring, the reaction mixture is then slowly added dropwise to a mixture of 350 g of sodium bicarbonate and 1 liter of water. The aqueous phase is extracted with dichloromethane (five times 400 ml each). The combined organic phases are dried over sodium sulfate, filtered and freed from the solvent using a rotary evaporator. This gives 23.1 g (80% of theory) of the title compound, which is reacted without further purification.

$^1$H-NMR (400 MHz, DMSO-$d_6$): δ=8.32 (d, 1H), 7.78 (dd, 1H), 7.49 (d, 1H), 4.10 (q, 2H), 3.77 (s, 2H), 1.19 (t, 3H).

LC-MS (Method 3): $R_t$=1.91 min; MS (ESIpos): m/z=200 [M+H]$^+$.

Example 2A

Ethyl 2-(6-chloropyridin-3-yl)-3-(dimethylamino)acrylate

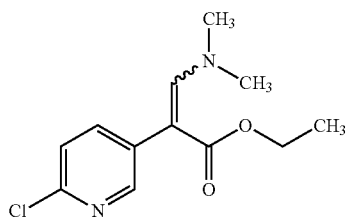 [SMILES: CCOC(=O)C(=CN(C)C)c1ccc(Cl)nc1]

3.99 g (20.0 mmol) of the compound from Example 1A are dissolved in 13.7 ml of dimethylformamide diethyl acetal, and the mixture is stirred with microwave irradiation at 90° C. for 30 min. The mixture is then concentrated on a rotary evaporator, and the residue is chromatographed on silica gel 60 (mobile phase: dichloromethane→dichloromethane/methanol 20:1).

Yield: 5.06 g (99% of theory)

$^1$H-NMR (300 MHz, DMSO-$d_6$): δ=8.13 (d, 1H), 7.61 (s, 1H), 7.58 (dd, 1H), 7.41 (d, 1H), 4.01 (q, 2H), 2.70 (s, 6H), 1.12 (t, 3H).

LC-MS (Method 3): $R_t$=1.98 min; MS (ESIpos): m/z=255 [M+H]$^+$.

Example 3A

Ethyl 3-(dimethylamino)-2-pyridin-3-ylacrylate

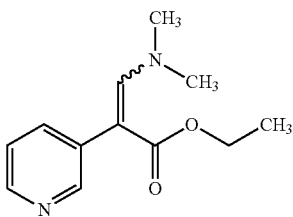 [SMILES: CCOC(=O)C(=CN(C)C)c1cccnc1]

37.4 g (226 mmol) of ethyl pyridin-3-ylacetate in 100 g (679 mmol) of dimethylformamide diethyl acetal are heated at 100° C. overnight. After cooling, the mixture is concentrated and the residue is initially pre-purified by flash chromatography on silica gel (mobile phase: gradient cyclohexane/ethyl acetate 1:1 ethyl acetate/ethanol 9:1). The product obtained in this manner is then subjected to fine purification by distillation under reduced pressure (1 mbar, bath temperature 200° C.).

Yield: 35.0 g (70% of theory)

$^1$H-NMR (400 MHz, DMSO-$d_6$): δ=8.37 (dd, 1H), 8.31 (dd, 1H), 7.59 (s, 1H), 7.51 (dt, 1H), 7.29 (ddd, 1H), 4.00 (q, 2H), 2.67 (s, 6H), 1.11 (t, 3H).

LC-MS (Method 1): $R_t$=2.38 min; MS (ESIpos): m/z=221 [M+H]$^+$.

Example 4A

Benzophenone (6-chloropyrimidin-4-yl)hydrazone

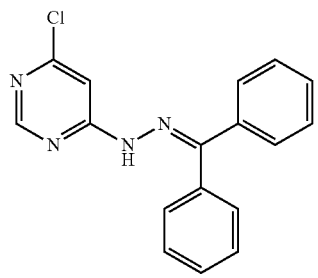 [SMILES: Clc1cc(NN=C(c2ccccc2)c2ccccc2)ncn1]

10.0 g (67.1 mmol) of 4,6-dichloropyrimidine, 14.5 g (73.8 mmol) of benzophenone hydrazone, 9.03 g (94.0 mmol) of sodium tert-butoxide, 409 mg (3.36 mmol) of phenylboronic acid, 301 mg (1.34 mmol) of palladium(II) acetate and 384 mg (1.34 mmol) of rac-2,2'-bis-(diphenylphosphino)-1,1'-binaphthalene are combined. The mixture is degassed and vented twice with argon, 400 ml of dry degassed toluene are added, the mixture is again degassed and vented twice with argon and heated at 90° C. overnight. After cooling, the reaction mixture is poured into water, the aqueous phase is extracted with ethyl acetate, the combined organic phases are concentrated and the residue is taken up in a mixture of dichloromethane and diethyl ether. The precipitate that remains is filtered off with suction (and discarded), the filtrate is concentrated and the residue is purified by column chromatography on silica gel 60 (mobile phase: toluene/ethyl acetate 8:2).

Yield: 6.00 g (29% of theory)
LC-MS (Method 3): $R_t$=2.86 min; MS (ESIpos): m/z=309 $[M+H]^+$.

Example 5A

Benzophenone [6-(4-methylpiperazin-1-yl)pyrimidin-4-yl]hydrazone

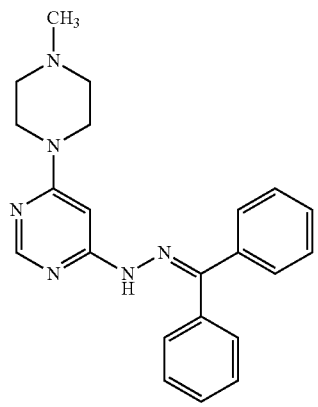 [SMILES: CN1CCN(c2cc(NN=C(c3ccccc3)c3ccccc3)ncn2)CC1]

500 mg (1.62 mmol) of the compound from Example 4A, 178 mg (1.78 mmol) of N-methylpiperazine, 58 mg (0.12 mmol) of dicyclohexyl-(2',4',6'-triisopropylbiphenyl-2-yl)phosphine, 22 mg (24 μmol) of tris(dibenzylideneacetone)dipalladium and 1.32 g (4.05 mmol) of cesium carbonate are combined. The mixture is degassed and vented twice with argon, 12.5 ml of a mixture of tert-butanol and toluene (1:5) are added, the mixture is again degassed and vented twice with argon and heated at 120° C. for 24 h. Another 58 mg (0.12 mmol) of dicyclohexyl-(2',4',6'-triisopropylbiphenyl-2-yl)phosphine and 22 mg (24 μmol) of tris(dibenzylideneacetone)dipalladium are then added, the mixture is heated at 120° C. overnight, another 324 mg (3.24 mmol) of N-methylpiperazine are then added and the mixture is heated at 120° C. for a further night. After cooling, the reaction mixture is filtered through kieselguhr, the filtrate is concentrated and the residue is purified by preparative HPLC (RP18 column; mobile phase: acetonitrile/water gradient with addition of 0.1% conc. hydrochloric acid).

Yield: 312 mg (52% of theory)
LC-MS (Method 5): $R_t$=1.64 min; MS (ESIpos): m/z=373 $[M+H]^+$.

Example 6A

4-Hydrazino-6-(4-methylpiperazin-1-yl)pyrimidine

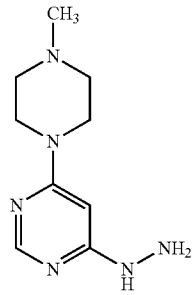

300 mg (808 μmol) of the compound from Example 5A in 15 ml conc. hydrochloric acid are heated at 65° C. for 4 h. After cooling, the reaction mixture is washed with dichloromethane and the aqueous phase is concentrated. This gives 162 mg of the crude product as the hydrochloride. This is stirred with polymer-bound tris-(2-aminoethyl)amine in dichloromethane at RT. After filtration, the filtrate is concentrated and the residue is dried under high vacuum.

Yield: 115 mg (69% of theory)
$^1$H-NMR (400 MHz, DMSO-$d_6$): δ=7.93 (s, 1H), 7.64 (s, 1H), 5.91 (s, 1H), 4.13 (s, 2H), 3.48-3.44 (m, 4H), 2.36-2.31 (m, 4H), 2.20 (s, 3H).
LC-MS (Method 1): $R_t$=0.41 min; MS (ESIpos): m/z=209 $[M+H]^+$.

Example 7A

4-Chloro-6-hydrazinopyrimidine

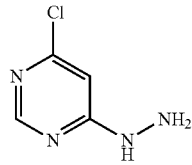

With stirring and at RT, 11.8 ml (12.1 g, 241.6 mmol) of hydrazine hydrate are added dropwise to a solution of 20.0 g (134.3 mmol) of 4,6-dichloropyrimidine in 300 ml of ethanol. If the solution becomes turbid during the addition of the hydrazine hydrate, more solvent (about 400 ml of ethanol) is added. The reaction solution is stirred at RT for a further 12 h. For work-up, the precipitated solid is filtered off, the filter residue is washed twice with in each case 150 ml of water and twice with in each case 100 ml of diethyl ether and the product is dried under reduced pressure. A further crystalline fraction is obtained from the concentrated mother liquor.

Yield: 16.8 g (87% of theory)

LC-MS (Method 1): $R_t$=1.17 min; MS (ESIpos): m/z=145 [M+H]$^+$;

$^1$H-NMR (400 MHz, DMSO-d$_6$): δ=8.81 (s, 1H), 8.17 (br. s, 1H), 6.75 (s, 1H), 4.48 (br. s, 2H).

Example 8A

4-Hydrazino-6-piperidin-1-ylpyrimidine

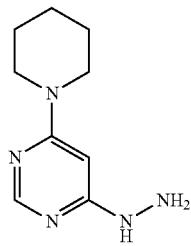 [SMILES: NNc1cc(N2CCCCC2)ncn1]

Step a): 4-Chloro-6-piperidin-1-ylpyrimidine

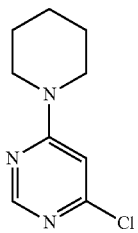 [SMILES: Clc1cc(N2CCCCC2)ncn1]

A mixture of 10.0 g (67.1 mmol) of 4,6-dichloropyrimidine and 5.7 g (67.1 mmol) of piperidine in 100 ml of water is stirred at a bath temperature of 115° C. for 16 h. After cooling to RT, the precipitate is filtered off, washed with water and dried under reduced pressure.

Yield: 6.4 g (47% of theory)

LC-MS (Method 4): $R_t$=2.16 min; MS (ESIpos): m/z=198 [M+H]$^+$;

$^1$H-NMR (400 MHz, DMSO-d$_6$): δ=8.29 (s, 1H), 6.92 (s, 1H), 3.65-3.58 (m, 4H), 1.66-1.62 (m, 2H), 1.60-1.48 (m, 4H).

Step b): 4-Hydrazino-6-piperidin-1-ylpyrimidine

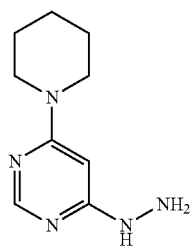 [SMILES: NNc1cc(N2CCCCC2)ncn1]

With stirring and at RT, 17.7 ml (18.2 g, 364.2 mmol) of hydrazine hydrate are added dropwise to a solution of 6.0 g (30.4 mmol) of 4-chloro-6-piperidin-1-ylpyrimidine in 50 ml of ethanol. The reaction solution is stirred at 80° C. for a further 16 h. For work-up, the mixture is concentrated under reduced pressure, the residue is stirred in water, the precipitated solid is filtered off, the filter residue is washed twice with in each case 150 ml of water and twice with in each case 100 ml of diethyl ether and the product is dried under reduced pressure.

Yield: 4.0 g (69% of theory)

LC-MS (Method 1): $R_t$=2.06 min; MS (ESIpos): m/z=194 [M+H]$^+$;

$^1$H-NMR (400 MHz, DMSO-d$_6$): δ=7.91 (s, 1H), 7.54 (br. s, 1H), 5.89 (s, 1H), 4.11 (br. s, 2H), 3.50-3.47 (m, 4H), 1.61-1.58 (m, 2H), 1.51-1.46 (m, 4H).

Example 9A 4-(6-Hydrazinopyrimidin-4-yl)morpholine

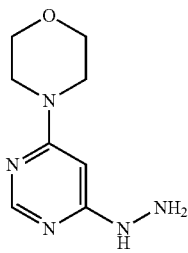 [SMILES: NNc1cc(N2CCOCC2)ncn1]

Step a): 4-(6-Chloropyrimidin-4-yl)morpholine

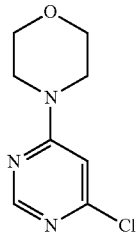 [SMILES: Clc1cc(N2CCOCC2)ncn1]

45.0 g (302.1 mmol) of 4,6-dichloropyrimidine are initially charged in 450 ml of water. 26.3 g (302.1 mmol) of morpholine are added, and the mixture is stirred at 90° C. for 16 h. The mixture is then cooled to 0° C., and the precipitate formed is filtered off. The precipitate is washed once with 50 ml of water and air-dried.

Yield: 51.0 g (85% of theory)

LC-MS (Method 4): $R_t$=1.09 min; MS (ESIpos): m/z=200 [M+H]$^+$;

$^1$H-NMR (400 MHz, DMSO-d$_6$): δ=8.35 (s, 1H), 6.95 (s, 1H), 3.62 (s, 8H).

Step b): 4-(6-Hydrazinopyrimidin-4-yl)morpholine

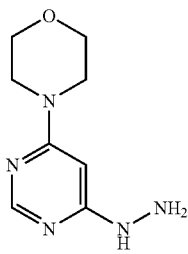 [SMILES: NNc1cc(N2CCOCC2)ncn1]

53.0 g (0.27 mol) of 4-(6-chloropyrimidin-4-yl)morpholine are initially charged in 260 ml of ethanol. 132.9 g (2.7 mol) of hydrazine hydrate are added, and the mixture is stirred under reflux for 16 h. The mixture is cooled to RT, and half of the solvent is removed by distillation. The mixture is then cooled to 0° C., and the solid formed is filtered off. The solid is washed with cold ethanol and initially air-dried and then dried under reduced pressure.

Yield: 35.0 g (68% of theory)

LC-MS (Method 1): $R_t$=0.17 min; MS (ESIpos): m/z=196 [M+H]$^+$;

$^1$H-NMR (400 MHz, DMSO-d$_6$): δ=7.94 (s, 1H), 7.70 (s, 1H), 5.91 (s, 1H), 4.15 (s, 2H), 3.66-3.60 (m, 4H), 3.45-3.37 (m, 4H).

Example 10A

Ethyl (5-bromopyridin-3-yl)acetate

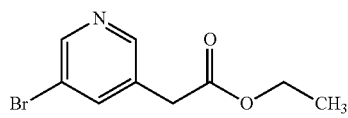

5.0 g (23.1 mmol) of (5-bromopyridin-3-yl)acetic acid in 30 ml of ethanol and 25 drops of conc. sulfuric acid are stirred at boiling point for 16 h. For work-up, the reaction mixture is concentrated under reduced pressure, the residue is taken up in ethyl acetate and washed repeatedly with semiconcentrated sodium bicarbonate solution, the organic phase is dried over sodium sulfate, the drying agent is filtered off, the solvent is removed completely on a rotary evaporator and the product is dried under reduced pressure for 16 h.

Yield: 5.2 g (91% of theory)

LC-MS (Method 1): $R_t$=1.48 min; MS (ESIpos): m/z=246 [M+H]$^+$;

$^1$H-NMR (400 MHz, DMSO-d$_6$): δ=8.59 (d, 1H), 8.48 (d, 1H), 8.00 (dd, 1H), 4.11 (q, 2H), 3.78 (s, 2H), 1.21 (t, 3H).

Example 11A

Ethyl 3-(dimethylamino)-2-(5-bromopyridin-3-yl)acrylate

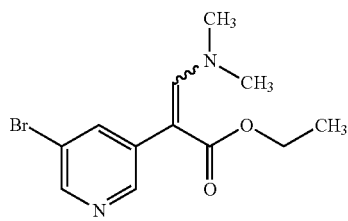 [SMILES: CCOC(=O)C(=CN(C)C)c1cncc(Br)c1]

5.1 g (20.9 mmol) of the compound from Example 10A are stirred in 7.2 ml (6.2 g, 41.8 mmol) of dimethylformamide diethyl acetal at a bath temperature of 100° C. for 16 h. After cooling, the mixture is concentrated under reduced pressure, the residue is stirred in diisopropyl ether, and the solid is filtered off and finally washed with diisopropyl ether. The crude product is dried under reduced pressure for 16 h.

Yield: 6.1 g (73% of theory)

LC-MS (Method 7): $R_t$=1.86 min; MS (ESIpos): m/z=299 [M+H]$^+$;

$^1$H-NMR (400 MHz, DMSO-d$_6$): δ=8.49 (d, 1H), 8.29 (d, 1H), 7.78 (dd, 1H), 7.61 (s, 1H), 4.02 (q, 2H), 2.71 (s, 6H), 1.12 (t, 3H).

Example 12A

2-Hydrazinopyrazine

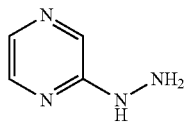

20.0 g (174.6 mmol) of chloropyrazine are added dropwise to 61.7 g (1.2 mol) of hydrazine hydrate, and the mixture is stirred at 120° C. for 45 min. The mixture is then allowed to stand at 2° C. for 24 h. The solid is filtered off and washed twice with petroleum ether. The solid is initially air-dried and then dried under high vacuum. The solid is then recrystallized from toluene and again dried under high vacuum.

Yield: 6.5 g (34% of theory)

LC-MS (Method 1): $R_t$=0.41 min; MS (ESIpos): m/z=111 [M+H]$^+$.

Example 13A

2-Hydrazinoquinoxaline

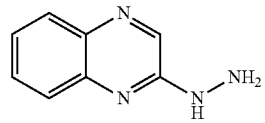 [SMILES: NNc1cnc2ccccc2n1]

15.0 g (91.1 mmol) of 2-chloroquinoxaline are initially charged in 150 ml of ethanol. 45.6 g (911.3 mmol) of hydrazine hydrate are added, and the mixture is stirred under reflux for 16 h. The mixture is then cooled to 0° C., and the solid formed is filtered off, washed with ethanol and dried under high vacuum.

Yield: 11.5 g (79% of theory)

LC-MS (Method 1): $R_t$=1.75 min; MS (ESIpos): m/z=161 [M+H]$^+$;

$^1$H-NMR (400 MHz, DMSO-d$_6$): δ=8.70 (s, 1H), 8.35 (s, 1H), 7.78 (d, 1H), 7.60-7.50 (m, 2H), 7.37-7.28 (m, 1H), 4.50-4.38 (m, 2H).

Example 14A

2-Hydrazinoquinoline

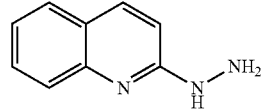 [SMILES: NNc1ccc2ccccc2n1]

21.0 g (128.4 mmol) of 2-chloroquinoline are initially charged in 210 ml of ethanol. 64.3 g (1.3 mol) of hydrazine hydrate are added, and the mixture is stirred under reflux for 16 h. The mixture is then cooled to 0° C., and the solid formed is filtered off and washed with a little ethanol. The product is initially air-dried and then dried under high vacuum.

Yield: 14.5 g (71% of theory)

LC-MS (Method 1): $R_t$=1.95 min; MS (ESIpos): m/z=160 [M+H]$^+$;

$^1$H-NMR (400 MHz, DMSO-d$_6$): δ=8.08 (br. s, 1H), 7.87 (d, 1H), 7.63 (d, 1H), 7.57-7.43 (m, 2H), 7.16 (t, 1H), 6.85 (d, 1H), 4.35 (br. s, 2H).

EXEMPLARY EMBODIMENTS

Example 1

2-(6-Piperidin-1-yl-pyrimidin-4-yl)-4-pyridin-3-yl-1,2-dihydro-3H-pyrazol-3-one hydrochloride

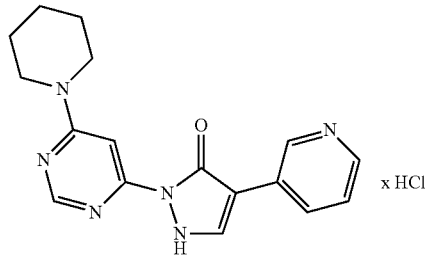 [SMILES: O=c1c(-c2cccnc2)c[nH]n1-c1cc(N2CCCCC2)ncn1]

137 mg (621 μmol) of the compound from Example 3A, 100 mg (517 μmol) of 4-hydrazino-6-piperidin-1-ylpyrimidine [Postovskii, I. Ya., Smirnova, N. B., *Doklady Akademii Nauk SSSR* 1966, 166, 1136-1139; *Chem. Abstr.* 64:93457 (1966)] and 12 mg (52 μmol) of camphor-10-sulfonic acid are dissolved in 3.5 ml of anhydrous ethanol and heated under reflux overnight. After cooling, the mixture is concentrated and the residue is purified by preparative HPLC (RP18 column; mobile phase: acetonitrile/water gradient with addition of 0.1% conc. hydrochloric acid). This gives 108 mg (58% of theory) of the title compound.

$^1$H-NMR (400 MHz, DMSO-d$_6$): δ=9.27 (s, 1H), 8.85 (d, 1H), 8.52 (s, 1H), 8.48 (s, 1H), 8.45 (d, 1H), 7.93 (dd, 1H), 7.41 (s, 1H), 3.83-3.70 (m, 4H), 1.73-1.56 (m, 6H).

LC-MS (Method 4): $R_t$=1.13 min; MS (ESIpos): m/z=323 [M+H]$^+$.

The compounds listed in Table 1 below are prepared analogously to Example 1 from the appropriate starting materials. The respective crude product can be purified by preparative HPLC with or without addition of 0.1% conc. hydrochloric acid (Method A). In an alternative work-up, after cooling, the precipitate formed is filtered off with suction, washed with ethanol and/or diethyl ether, dried and, if appropriate, subjected to fine-purification by preparative HPLC (RP18 column; mobile phase: acetonitrile/water gradient with or without addition of 0.1% conc. hydrochloric acid) (Method B).

TABLE 1

| Example No. | Structure | Starting materials; Yield (% of theory), Method | MS (ESI) [M + H]$^+$; LC-MS $R_t$ (Meth.) | $^1$H-NMR (400 MHz, DMSO-d$_6$) |
|---|---|---|---|---|
| 2 | 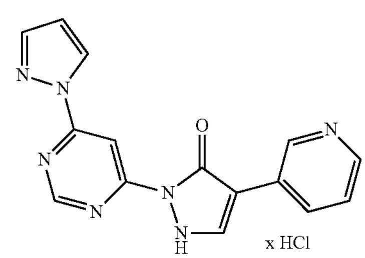 [SMILES: O=c1c(-c2cccnc2)c[nH]n1-c1cc(-n2cccn2)ncn1] | 3A, a; 19%, A | m/z = 306; 1.08 min (4) | δ = 9.37 (s, 1H), 8.98 (d, 1H), 9.02-8.95 (m, 2H), 8.88 (d, 1H), 8.72 (d, 1H), 8.62 (d, 1H), 8.00 (s, 1H), 7.96-7.90 (m, 1H), 6.70 (s, 1H). |
| 3 | 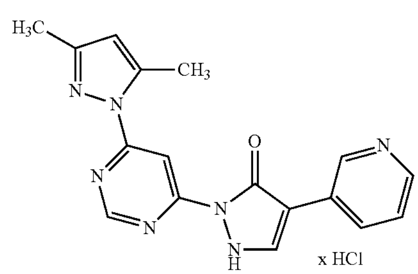 [SMILES: Cc1cc(C)n(-c2cc(-n3[nH]cc(-c4cccnc4)c3=O)ncn2)n1] | 3A, a; 18%, A | m/z = 334; 1.38 min (4) | δ = 9.42 (s, 1H), 9.02-8.95 (m, 3H), 8.90 (s, 1H), 8.67 (d, 1H), 8.03 (dd, 1H), 6.26 (s, 1H), 2.70 (s, 3H), 2.26 (s, 3H). |

TABLE 1-continued

| Example No. | Structure | Starting materials; Yield (% of theory), Method | MS (ESI) [M + H]+; LC-MS R_t (Meth.) | 1H-NMR (400 MHz, DMSO-d_6) |
|---|---|---|---|---|
| 4 | 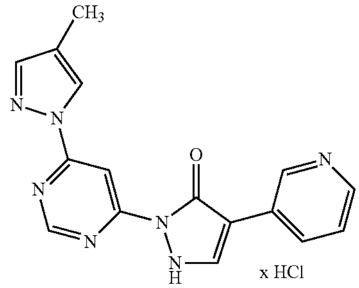 [SMILES: Cc1cnn(-c2cc(-n3[nH]cc(-c4cccnc4)c3=O)ncn2)c1] | 3A, a; 21%, A | m/z = 320; 1.43 min (3) | δ = 9.40 (s, 1H), 9.00-8.95 (m, 3H), 8.89 (s, 1H), 8.67 (d, 1H), 8.48 (s, 1H), 8.02 (dd, 1H), 7.83 (s, 1H), 2.14 (s, 3H). |
| 5 | 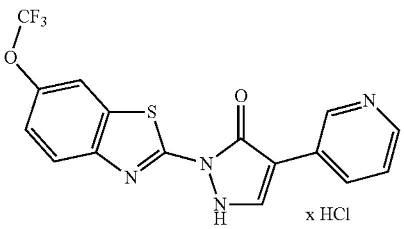 [SMILES: O=c1c(-c2cccnc2)c[nH]n1-c1nc2ccc(OC(F)(F)F)cc2s1] | 3A, b; 4%, A | m/z = 379; 1.63 min (4) | δ = 9.33 (s, 1H), 8.87 (d, 1H), 8.73 (s, 1H), 8.52 (d, 1H), 8.22 (s, 1H), 7.98-7.90 (m, 2H), 7.48 (d, 1H). |
| 6 | 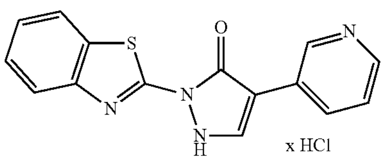 [SMILES: O=c1c(-c2cccnc2)c[nH]n1-c1nc2ccccc2s1] | 3A, a; 18%, A | m/z = 295; 1.46 min (5) | δ = 9.36 (s, 1H), 8.96-8.88 (m, 2H), 8.61 (d, 1H), 8.12 (d, 1H), 8.01 (dd, 1H), 7.89 (d, 1H), 7.53 (t, 1H), 7.41 (t, 1H). |
| 7 | 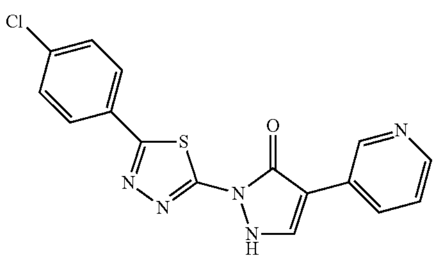 [SMILES: O=c1c(-c2cccnc2)c[nH]n1-c1nnc(-c2ccc(Cl)cc2)s1] | 3A, a; 10%, B | m/z = 356; 1.72 min (5) | δ = 9.01 (d, 1H), 8.13 (d, 1H), 8.05 (d, 1H), 8.01-7.95 (m, 3H), 7.62-7.57 (m, 2H), 7.17 (dd, 1H). |
| 8 | 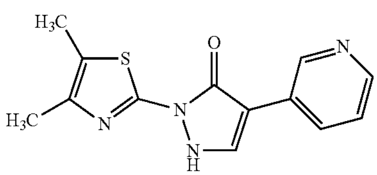 [SMILES: Cc1nc(-n2[nH]cc(-c3cccnc3)c2=O)sc1C] | 3A, d; 60%, B | m/z = 273; 0.83 min (4) | δ = 9.14 (s, 1H), 8.47-8.35 (m, 2H), 8.33-8.29 (m, 1H), 7.52-7.45 (m, 1H), 2.31 (s, 3H), 2.24 (s, 3H). |
| 9 | 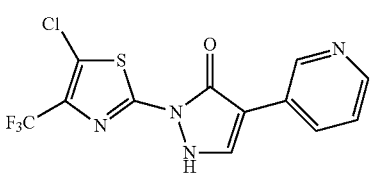 [SMILES: O=c1c(-c2cccnc2)c[nH]n1-c1nc(C(F)(F)F)c(Cl)s1] | 3A, e; 7%, B | m/z = 347; 1.53 min (4) | δ = 9.00 (s, 1H), 8.22 (d, 1H), 8.10 (d, 1H), 8.03 (s, 1H), 7.29 (dd, 1H). |
| 10 | 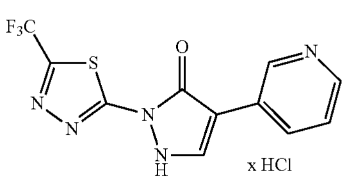 [SMILES: O=c1c(-c2cccnc2)c[nH]n1-c1nnc(C(F)(F)F)s1] | 3A; 43%, B | m/z = 314; 1.36 min (3) | δ = 9.21 (s, 1H), 8.75 (d, 1H), 8.36-8.27 (m, 2H), 7.88-7.79 (m, 1H). |

TABLE 1-continued

| Example No. | Structure | Starting materials; Yield (% of theory), Method | MS (ESI) [M + H]+; LC-MS $R_t$ (Meth.) | 1H-NMR (400 MHz, DMSO-$d_6$) |
|---|---|---|---|---|
| 11 | (4-cyano-5-chlorothiazol-2-yl pyrazolone with pyridin-3-yl) | 3A, e; 4%, B | m/z = 304; 1.22 min (4) | δ = 8.96 (d, 1H), 8.11-8.04 (m, 2H), 8.02 (s, 1H), 7.17 (dd, 1H). |
| 12 | (3-methylthio-1,2,4-thiadiazol-5-yl pyrazolone with pyridin-3-yl) x HCl | 3A, f; 12%, B | m/z = 292; 1.21 min (3) | (DCOOD): δ = 10.1 (s, 1H), 9.62 (d, 1H), 9.49-9.35 (m, 2H), 8.87-8.77 (m, 1H), 3.30 (s, 3H). |
| 13 | (4-methyl-5-(4-methoxyphenyl)thiazol-2-yl pyrazolone with pyridin-3-yl) | 3A; 35%, B | m/z = 356; 1.49 min (4) | δ = 9.19 (s, 1H), 8.51-8.27 (m, 3H), 7.69-7.63 (m, 2H), 7.59-7.52 (m, 1H), 7.06-7.01 (m, 2H), 3.81 (s, 3H). | re: the synthesis of the corresponding hydrazinopyrimidine derivatives:
a): the synthesis of the corresponding hydrazinopyrimidine can be carried out analogously to Example 6A;
b): 2-hydrazino-6-trifluoromethoxybenzothiazole: S. Mignani et al., *Synth. Commun.* 1992, 22, 2769-2780;
c): 2-hydrazino-5-(4-chlorophenyl)-1,3,4-thiadiazole: S. Turner et al., *J. Med. Chem.* 1988, 31, 902-906;
d): 2-hydrazino-4,5-dimethylthiazole: Beyer et al., *Chem. Ber.* 1954, 87, 1385;
e): 5-chloro-2-hydrazino-4-trifluoromethylthiazole and 5-chloro-4-cyano-2-hydrazinothiazole: DE 39 40 794-A1;
f): 5-hydrazino-3-methylthio-1,2,4-thiadiazole: K.T. Potts, R. Armbruster, *J. Heterocycl. Chem.* 1972, 9, 651-7.

Example 14

2-(6-Pyrrolidin-1-ylpyrimidin-4-yl)-4-pyridin-3-yl-1,2-dihydro-3H-pyrazol-3-one hydrochloride

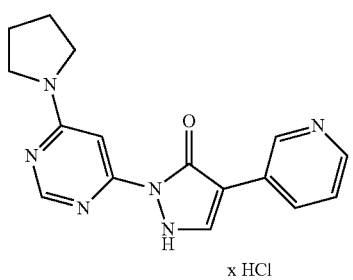 [SMILES: O=c1c(-c2cccnc2)c[nH]n1-c1cc(N2CCCC2)ncn1]

x HCl 148 mg (670 μmol) of the compound from Example 3A, 100 mg (558 μmol) of 4-hydrazino-6-pyrrolidin-1-ylpyrimidine [Postovskii, I. Ya., Smirnova, N. B., *Doklady Akademii Nauk SSSR* 1966, 166, 1136-1139; *Chem. Abstr.* 64:93457 (1966)] and 13 mg (56 μmol) of camphor-10-sulfonic acid are dissolved in 3.7 ml of anhydrous ethanol and heated under reflux overnight. After cooling, the mixture is concentrated, the residue is taken up in 5 ml of ethanol, 0.25 ml (837 μmol) of a 21% strength ethanolic sodium methoxide solution is added and the mixture is stirred at RT for 1 h. By addition of 1 M hydrochloric acid, the pH is then adjusted to 5-6, the mixture is concentrated and the residue is purified by preparative HPLC (RP18 column; mobile phase: acetonitrile/water gradient with addition of 0.1% conc. hydrochloric acid). This gives 30 mg (16% of theory) of the title compound.

1H-NMR (400 MHz, DMSO-$d_6$): δ=9.26 (s, 1H), 8.83 (d, 1H), 8.53 (s, 1H), 8.46 (s, 1H), 8.43 (d, 1H), 7.92 (dd, 1H), 7.09 (s, 1H), 3.75-3.45 (m, 4H), 2.10-1.91 (m, 4H).

LC-MS (Method 4): $R_t$=0.94 min; MS (ESIpos): m/z=309 [M+H]+.

The compounds listed in Table 2 below are prepared analogously to Example 14 from the appropriate starting materials. Alternatively, the base used can be an appropriate amount of methanolic sodium methoxide solution, the solvent used can be methanol and purification can be carried out by preparative HPLC without addition of 0.1% conc. hydrochloric acid.

TABLE 2

| Example No. | Structure | Starting materials; yield (% of theory) | MS (ESI) [M + H]+; LC-MS $R_t$ (Meth.) | 1H-NMR (400 MHz, DMSO-$d_6$) |
|---|---|---|---|---|
| 15 | (piperidinyl-pyrimidinyl-pyrazolone-chloropyridine) x HCl | 2A, g; 98% | m/z = 357; 2.56 min (3) | δ = 8.89 (d, 1H), 8.48 (s, 1H), 8.45 (s, 1H), 8.28 (dd, 1H), 7.46 (d, 1H), 7.42 (s, 1H), 3.74-3.66 (m, 4H), 1.71-1.49 (m, 6H). |
| 16 | (morpholinyl-pyrimidinyl-pyrazolone-chloropyridine) x HCl | 2A, g; 86% | m/z = 359; 2.09 min (3) | δ = 8.91 (d, 1H), 8.53-8.46 (m, 2H), 8.29 (d, 1H), 7.53-7.44 (m, 2H), 3.74-3.64 (m, 8H). |
| 17 | (pyrrolidinyl-pyrimidinyl-pyrazolone-chloropyridine) x HCl | 2A, g; 99% | m/z = 343; 2.19 min (3) | δ = 8.88 (d, 1H), 8.47 (s, 1H), 8.37 (s, 1H), 8.27 (d, 1H), 7.44 (d, 1H), 7.08 (s, 1H), 3.66-3.40 (m, 4H), 2.07-1.90 (m, 4H). | g): 4-hydrazino-6-piperidin-1-ylpyrimidine, 4-hydrazino-6-pyrrolidin-1-ylpyrimidine and 4-hydrazino-6-morpholin-4-ylpyrimidine: Postovskii, I. Ya., Smirnova, N. B., *Doklady Akademii Nauk SSSR* 1966, 166, 1136-1139; *Chem.* Abstr. 64: 93457 (1966).

Example 18

2-(6-Morpholin-4-yl-pyrimidin-4-yl)-4-pyridin-3-yl-1,2-dihydro-3H-pyrazol-3-one hydrochloride

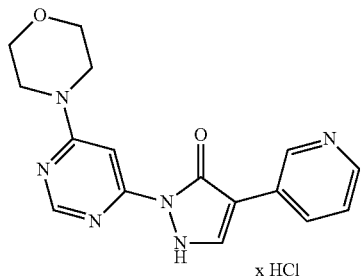 [SMILES: O=c1c(-c2cccnc2)c[nH]n1-c1cc(N2CCOCC2)ncn1]

677 mg (3.07 mmol) of the compound from Example 3A, 500 mg (2.56 mmol) of 4-hydrazino-6-morpholin-4-ylpyrimidine [Postovskii, I. Ya., Smirnova, N. B., *Doklady Akademii Nauk SSSR* 1966, 166, 1136-1139; *Chem. Abstr.* 64:93457 (1966)] and 60 mg (256 μmol) of camphor-10-sulfonic acid are dissolved in 20 ml of anhydrous ethanol and heated under reflux overnight. After cooling, the mixture is concentrated, the residue is suspended in a little ethanol, the precipitate is filtered off with suction, washed with ethanol and diethyl ether, resuspended in methanol, an excess of a 4 N solution of hydrogen chloride in 1,4-dioxane is added and the mixture is concentrated again. This gives 423 mg (46% of theory) of the title compound.

1H-NMR (400 MHz, DMSO-$d_6$): δ=9.29 (s, 1H), 8.87 (s, 1H), 8.57-8.55 (m, 2H), 8.50 (d, 1H), 7.96 (dd, 1H), 7.47 (s, 1H), 5.20-4.40 (m, 4H), 3.77-3.70 (m, 4H).

LC-MS (Method 3): $R_t$=0.94 min; MS (ESIpos): m/z=325 [M+H]+.

Example 19

2-[6-(4-Methylpiperazin-1-yl)-pyrimidin-4-yl]-4-pyridin-3-yl-1,2-dihydro-3H-pyrazol-3-one dihydrochloride

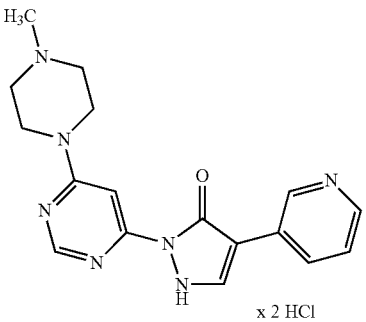 [SMILES: CN1CCN(c2cc(-n3[nH]cc(-c4cccnc4)c3=O)ncn2)CC1]

146 mg (663 µmol) of the compound from Example 3A, 115 mg (552 µmol) of the compound from Example 6A and 13 mg (55 µmol) of camphor-10-sulfonic acid are dissolved in 5 ml of anhydrous ethanol, and the mixture is heated under reflux overnight. After cooling, the mixture is concentrated and the residue is purified by preparative HPLC (RP18 column; mobile phase: acetonitrile/water gradient with addition of 0.1% conc. hydrochloric acid). The resulting mixture of target product and intermediate is dissolved in 5 ml of anhydrous ethanol, 109 mg (607 µmol) of a 30% strength methanolic sodium methoxide solution are added and the mixture is stirred at RT for 1 h. The mixture is then neutralized with 1 M hydrochloric acid and concentrated, and the residue is purified by preparative HPLC (RP18 column; mobile phase: acetonitrile/water gradient with addition of 0.1% conc. hydrochloric acid). The mixture of target product and intermediate obtained this time is again dissolved in 5 ml of anhydrous ethanol, 99 mg (552 µmol) of a 30% strength methanolic sodium methoxide solution are added and the mixture is stirred at RT for 2 h. The mixture is then again neutralized with 1 M hydrochloric acid and concentrated, and the residue is purified by preparative HPLC (RP18 column; mobile phase: acetonitrile/water gradient with addition of 0.1% conc. hydrochloric acid). This gives 9 mg (4% of theory) of the title compound.

$^1$H-NMR (400 MHz, DMSO-d$_6$): δ=11.1 (s, 1H), 9.30 (s, 1H), 8.84 (d, 1H), 8.67 (s, 1H), 8.62 (s, 1H), 8.55 (d, 1H), 7.93 (dd, 1H), 7.64 (s, 1H), 4.62-4.50 (m, 2H), 3.57-3.44 (m, 4H), 3.18-3.05 (m, 2H), 2.81 (s, 3H).

LC-MS (Method 1): R$_t$=1.97 min; MS (ESIpos): m/z=338 [M+H]$^+$.

Example 20

2-(4-Hydroxyquinazolin-2-yl)-4-pyridin-3-yl-1,2-dihydro-3H-pyrazol-3-one hydrochloride

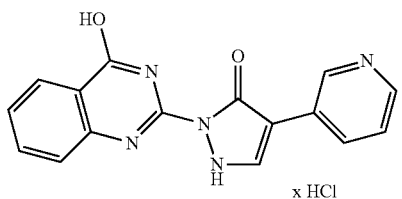 [SMILES: O=c1c(-c2cccnc2)c[nH]n1-c1nc(O)c2ccccc2n1]

200 mg (908 µmol) of the compound from Example 3A, 133 mg (757 µmol) of 2-hydrazinoquinazolin-4(3H)-one and 18 mg (76 µmol) of camphor-10-sulfonic acid are dissolved in 5 ml of anhydrous ethanol and heated under reflux overnight. After cooling, the precipitate is filtered off with suction, washed with diethyl ether and dried, and the precipitate is pre-purified by preparative HPLC (RP18 column; mobile phase: acetonitrile/water gradient with addition of 0.1% conc. hydrochloric acid). The product fractions are concentrated, and an excess of a 4 N solution of hydrogen chloride in 1,4-dioxane is added and the mixture is concentrated again. The residue is washed with diethyl ether and dried. This gives 75 mg (28% of theory) of the title compound.

$^1$H-NMR (400 MHz, DMSO-d$_6$): δ=9.10 (s, 1H), 8.39 (d, 1H), 8.21 (d, 1H), 8.08 (s, 1H), 8.06 (d, 1H), 7.74 (t, 1H), 7.59 (d, 1H), 7.48-7.42 (m, 1H), 7.35 (t, 1H).

LC-MS (Method 1): R$_t$=2.61 min; MS (ESIpos): m/z=306 [M+H]$^+$.

Example 21

2-[5-(4-Fluorophenyl)-1,3,4-thiadiazol-2-yl]-4-pyridin-3-yl-1,2-dihydro-3H-pyrazol-3-one hydrochloride

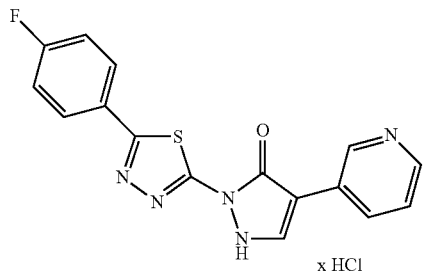 [SMILES: O=c1c(-c2cccnc2)c[nH]n1-c1nnc(-c2ccc(F)cc2)s1]

200 mg (908 µmol) of the compound from Example 3A, 159 mg (757 µmol) of 2-(4-fluorophenyl)-5-hydrazino-1,3,4-thiadiazole [for the preparation, cf. WO 2001/062208] and 18 mg (76 µmol) of camphor-10-sulfonic acid are dissolved in 5 ml of anhydrous ethanol and heated under reflux overnight. After cooling, the precipitate is separated off, the filtrate is concentrated, the filter residue is washed with acetonitrile and an excess of a 4 N solution of hydrogen chloride in 1,4-dioxane is added. After reconcentration, the residue is washed with diethyl ether and dried. This gives 80 mg (31% of theory) of the title compound.

$^1$H-NMR (400 MHz, DMSO-d$_6$): δ=9.27 (s, 1H), 8.79 (d, 1H), 8.40 (s, 1H), 8.37 (d, 1H), 8.06-8.00 (m, 2H), 7.86 (dd, 1H), 7.43-7.36 (m, 2H).

LC-MS (Method 1): R$_t$=2.80 min; MS (ESIpos): m/z=340 [M+H]$^+$.

Example 22

2-(6-Phenylpyridazin-3-yl)-4-pyridin-3-yl-1,2-dihydro-3H-pyrazol-3-one hydrochloride

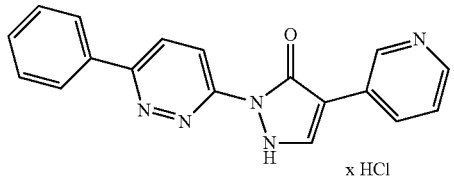 [SMILES: O=c1c(-c2cccnc2)c[nH]n1-c1ccc(-c2ccccc2)nn1]

142 mg (644 µmol) of the compound from Example 3A, 100 mg (537 µmol) of 3-hydrazino-6-phenylpyridazine and 13 mg (54 µmol) of camphor-10-sulfonic acid are dissolved in 4 ml of anhydrous ethanol and heated under reflux overnight. After cooling, the mixture is concentrated, a mixture of methanol and acetonitrile is added to the residue and the pH is adjusted to 5 by addition of 1 M hydrochloric acid. The precipitate is filtered off with suction and dried. This gives 123 mg (65% of theory) of the title compound.

$^1$H-NMR (400 MHz, DMSO-d$_6$): δ=9.40 (s, 1H), 8.97-8.92 (m, 2H), 8.83 (d, 1H), 8.64 (d, 1H), 8.51 (d, 1H), 8.21-8.15 (m, 2H), 7.98 (dd, 1H), 7.64-7.54 (m, 3H).

LC-MS (Method 4): R$_t$=1.24 min; MS (ESIpos): m/z=316 [M+H]$^+$.

Example 23

2-(6-Chloropyrimidin-4-yl)-4-pyridin-3-yl-1,2-dihydro-3H-pyrazol-3-one

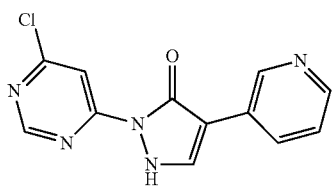 [SMILES: O=c1c(-c2cccnc2)c[nH]n1-c1cc(Cl)ncn1]

At RT, 30.0 g (207.5 mmol) of the compound from Example 7A and 50.3 g (228.3 mmol) of the compound from Example 3A are stirred in 1000 ml of glacial acetic acid for 16 h. For work-up, the solvent is removed on a rotary evaporator, the residue is taken up in ethyl acetate and washed with saturated sodium bicarbonate solution until neutral, and the organic phase is concentrated under reduced pressure. The residue is dissolved in 1000 ml of ethanol, 42.8 ml (41.1 g, 228.3 mmol) of 30% strength methanolic sodium methoxide solution are added and the mixture is stirred at RT for 2 h. The reaction mixture is then adjusted to pH 5 using 1 N hydrochloric acid and stirred for 16 h. The precipitate is filtered off, the filter residue is washed with water and ethanol and the product is dried under reduced pressure.

Yield: 43.5 g (77% of theory)

LC-MS (Method 1): $R_t$=2.19 min; MS (ESIpos): m/z=274 [M+H]$^+$;

$^1$H-NMR (400 MHz, DMSO-d$_6$): δ=9.18 (s, 1H), 8.78 (s, 1H), 8.70 (s, 1H), 8.20 (d, 1H), 8.08 (d, 1H), 8.02 (s, 1H), 7.22 (t, 1H).

Example 24

2-(6-Hydroxypyrimidin-4-yl)-4-pyridin-3-yl-1,2-dihydro-3H-pyrazol-3-one

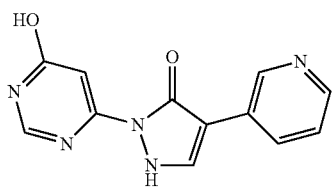 [SMILES: O=c1c(-c2cccnc2)c[nH]n1-c1cc(O)ncn1]

For 16 h, 2.8 g (19.6 mmol) of the compound from Example 7A and 4.3 g (19.6 mmol) of the compound from Example 3A are stirred in 50 ml of glacial acetic acid at boiling point (bath temperature 125° C.). For work-up, the resulting precipitate is filtered off, the filter residue is washed with diethyl ether and the filtrate is concentrated on a rotary evaporator. The filter residue is dissolved in 50 ml of ethanol, 18.5 ml (2.7 g, 39.2 mmol) of 21% strength ethanolic sodium methoxide solution are added and the solution is stirred at RT for 16 h. The reaction mixture is then adjusted to pH 5 using 1 N hydrochloric acid and stirred at RT for 2 h, the precipitate is then filtered off, the filter residue is washed with water and ethanol and the product is dried under reduced pressure.

Yield: 2.0 g (40% of theory)

LC-MS (Method 1): $R_t$=1.84 min; MS (ESIpos): m/z=256 [M+H]$^+$;

$^1$H-NMR (400 MHz, DMSO-d$_6$): δ=12.80 (br. s, 1H), 9.18 (s, 1H), 8.63 (s, 1H), 8.48 (d, 1H), 8.43 (d, 1H), 8.34 (s, 1H), 7.76 (dd, 1H), 7.22 (s, 1H).

Example 25

2-{6-[(2-Methoxyethyl)amino]pyrimidin-4-yl}-4-pyridin-3-yl-1,2-dihydro-3H-pyrazol-3-one hydrochloride

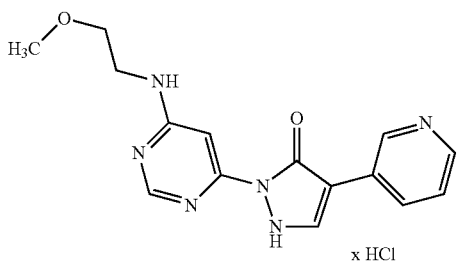 [SMILES: COCCNc1cc(-n2[nH]cc(-c3cccnc3)c2=O)ncn1]

100 mg (0.4 mmol) of the compound from Example 23, 64 µl (55 mg, 0.7 mmol) of 2-methoxyethylamine and 127 µl of N,N-diisopropylethylamine (94 mg, 0.7 mmol) are stirred in 3 ml of n-butanol under reflux for 1.5 h. The solvent is then removed completely on a rotary evaporator. The residue is stirred with diethyl ether/methanol, the precipitate is filtered off and the filter residue is washed with diethyl ether. The solid is stirred in 1.5 ml of 1 N hydrochloric acid and concentrated again, and the product is dried under reduced pressure.

Yield: 87 mg (68% of theory)

LC-MS (Method 1): $R_t$=2.11 min; MS (ESIpos): m/z=313 [M+H]$^+$;

$^1$H-NMR (400 MHz, D$_2$O): δ=8.98 (s, 1H), 8.62 (s, 1H), 8.47-8.32 (m, 1H), 8.26 (d, 1H), 8.11 (s, 1H), 7.81 (t, 1H), 6.91 (s, 1H), 3.73-3.43 (m, 4H), 3.31 (s, 3H).

Example 26

2-{6-[2-(Dimethylamino)ethoxy]pyrimidin-4-yl}-4-pyridin-3-yl-1,2-dihydro-3H-pyrazol-3-one hydrochloride

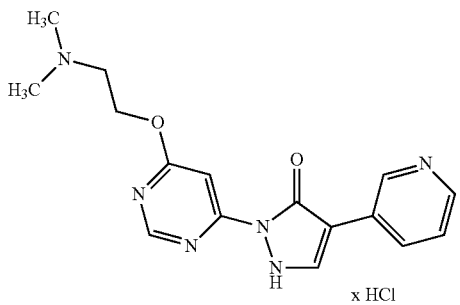 [SMILES: CN(C)CCOc1cc(-n2[nH]cc(-c3cccnc3)c2=O)ncn1]

99 mg (0.4 mmol, 60% in mineral oil) of sodium hydride are added to a solution of 35 µl (31 mg, 0.4 mmol) of N,N-dimethylethanolamine and 2 ml of anhydrous THF, and the mixture is stirred for 10 min 100 mg (0.4 mmol) of the compound from Example 23, suspended in 3 ml of anhydrous THF, and 6 mg (0.02 mmol) of tetra-n-butylammonium iodide are added, and the mixture is stirred at RT for 16 h. 1 N hydrochloric acid and water are then added, the mixture is concentrated on a rotary evaporator and the residue is stirred in methanol. The precipitated solid is filtered off, and the filtrate is concentrated under reduced pressure. The filter residue is stirred in diethyl ether, the precipitate is filtered off and the filter residue is purified further by preparative HPLC (RP18 column; mobile phase: acetonitrile/water gradient with addition of 0.1% formic acid). The resulting formate salt of the target compound is converted into the hydrochloride by addition of 2 ml 1 M hydrochloric acid and reconcentration.

Yield: 121 mg (96% of theory)

LC-MS (Method 1): $R_t$=1.83 min; MS (ESIpos): m/z=327 [M+H]$^+$;

$^1$H-NMR (400 MHz, D$_2$O): δ=9.34 (s, 1H), 8.85 (d, 1H), 8.62 (s, 1H), 8.54 (d, 1H), 8.48 (s, 1H), 8.02 (dd, 1H), 7.73 (s, 1H), 4.92-4.40 (m, 2H), 3.69 (t, 2H), 3.01 (s, 6H).

Example 27

4-Pyridin-3-yl-2-[6-(4-pyrrolidin-1-ylpiperidin-1-yl)pyrimidin-4-yl]-1,2-dihydro-3H-pyrazol-3-one dihydrochloride

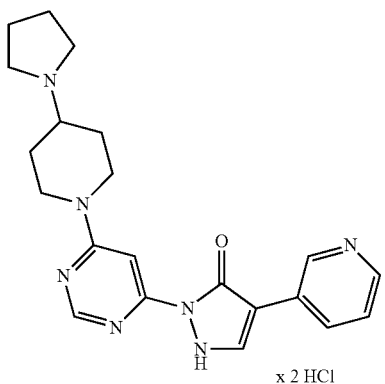 [SMILES: O=c1c(-c2cccnc2)c[nH]n1-c1cc(N2CCC(N3CCCC3)CC2)ncn1]

100 mg (0.4 mmol) of the compound from Example 23 and 113 mg (0.7 mmol) of 4-pyrrolidin-1-ylpiperidine are initially charged in 3 ml of THF. The reaction mixture is reacted in a single-mode microwave oven (Emrys Optimizer) at 120° C. for 24 min. The cooled reaction solution is then concentrated on a rotary evaporator, and the residue is chromatographed by preparative HPLC (RP18 column; mobile phase: acetonitrile/water gradient with addition of 0.1% formic acid). 1 ml of a 4 N solution of hydrogen chloride in dioxane is added to the resulting formate salt of the target compound, and the mixture is stirred at RT for 30 min. The suspension is then concentrated under reduced pressure, and the residue is dried.

Yield: 166 mg (98% of theory)

LC-MS (Method 1): $R_t$=1.92 min; MS (ESIpos): m/z=392 [M+H]$^+$;

$^1$H-NMR (400 MHz, DMSO-d$_6$): δ=11.45 (s, 1H), 9.48-9.28 (m, 1H), 8.88 (d, 1H), 8.67 (d, 1H), 8.49 (d, 1H), 8.47 (dd, 1H), 7.50 (s, 1H), 3.57-3.27 (m, 5H), 3.21-2.93 (m, 3H), 2.87-2.83 (m, 1H), 2.28-2.14 (m, 2H), 2.08-1.68 (m, 6H).

Example 28

2-{6-[4-(2-Methoxyethyl)piperazin-1-yl]pyrimidin-4-yl}-4-pyridin-3-yl-1,2-dihydro-3H-pyrazol-3-one dihydrochloride

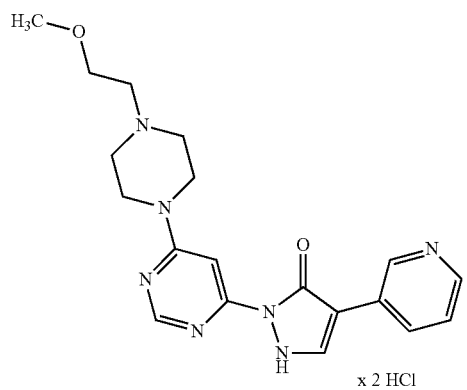 [SMILES: COCCN1CCN(c2cc(-n3[nH]cc(-c4cccnc4)c3=O)ncn2)CC1]

100 mg (0.4 mmol) of the compound from Example 23 and 113 mg (0.7 mmol) of N-(methoxy-ethyl)piperazine are initially charged in 3 ml of THF. The reaction mixture is reacted in a single-mode microwave oven (Emrys Optimizer) at 120° C. for 20 min. The cooled reaction solution is then concentrated on a rotary evaporator, and the residue is chromatographed by preparative HPLC (RP18 column; mobile phase: acetonitrile/water gradient with addition of 0.1% formic acid). 1 ml of a 4 N solution of hydrogen chloride in dioxane is added to the resulting formate salt of the target compound, and the mixture is stirred at RT for 30 min. The suspension is then concentrated under reduced pressure, and the residue is dried.

Yield: 124 mg (98% of theory)

LC-MS (Method 8): $R_t$=0.82 min; MS (ESIpos): m/z=382 [M+H]$^+$;

$^1$H-NMR (400 MHz, DMSO-d$_6$): δ=11.41 (br. s, 1H), 9.86 (br. s, 1H), 9.34 (s, 1H), 8.92 (d, 1H), 8.70 (s, 1H), 8.62 (s, 1H), 8.57 (d, 1H), 7.99 (dd, 1H), 7.62 (s, 1H), 3.82-3.71 (m, 4H), 3.68-3.28 (m, 9H), 3.26-3.10 (m, 2H).

Example 29

2-{6-[4-(Dimethylamino)piperidin-1-yl]pyrimidin-4-yl}-4-pyridin-3-yl-1,2-dihydro-3H-pyrazol-3-one dihydrochloride

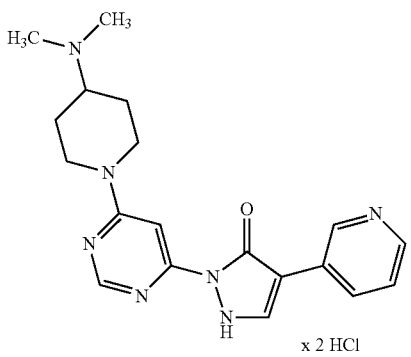 [SMILES: CN(C)C1CCN(c2cc(-n3[nH]cc(-c4cccnc4)c3=O)ncn2)CC1]

200 mg (0.7 mmol) of the compound from Example 23 and 187 mg (1.5 mmol) of 4-(N-(dimethyl-amino)piperidine are initially charged in 3 ml of THF. The reaction mixture is reacted in a single-mode microwave oven (Emrys Optimizer) at 180° C. for 5 min. The cooled reaction solution is then concentrated on a rotary evaporator, and the residue is chromatographed by preparative HPLC (RP18 column; mobile phase: acetonitrile/water gradient with addition of 0.1% formic acid). 1 ml of a 4 N solution of hydrogen chloride in dioxane is added to the resulting formate salt of the target compound, and the mixture is stirred at RT for 30 min. The suspension is then concentrated under reduced pressure, and the residue is dried.

Yield: 257 mg (80% of theory)

LC-MS (Method 9): $R_t$=0.76 min; MS (ESIpos): m/z=366 [M+H]$^+$;

$^1$H-NMR (400 MHz, DMSO-d$_6$): δ=11.32-11.05 (m, 1H), 9.34 (s, 1H), 9.03 (br. s, 1H), 8.87 (d, 1H), 8.58 (s, 2H), 8.49 (d, 1H), 7.95 (dd, 1H), 7.51 (s, 1H), 4.62-4.58 (m, 1H), 3.59-3.33 (m, 2H), 3.13-3.09 (m, 1H), 2.90-2.88 (m, 1H), 2.71 (s, 6H), 2.14-2.10 (m, 2H), 1.95-1.91 (m, 1H), 1.69-1.67 (m, 1H).

The compounds listed in Table 3 below are obtained from the appropriate starting materials using the reaction conditions and work-up methods below:

1 equivalent of the Exemplary Compound 23 is reacted in THF mit 2 equivalents of the appropriate amine in a single mode microwave (Emrys Optimizer) for 10-30 min at 120° C. If the starting material used is an ammonium salt of the amine component, 1 equivalent of N,N-diisopropylethylamine is added. The purification of the respective crude product from the concentrated reaction mixture is carried out by trituration in isopropanol. The precipitate obtained is filtered off and the filter residue is washed with isopropanol and/or diisopropyl ether, which gives the target product as the free base (Method A). In an alternative work-up, the concentrated filtrate or the concentrated reaction solution is purified by preparative HPLC (RP18 column; mobile phase: acetonitrile/water gradient with addition of 0.1% formic acid). A 4 N solution of hydrogen chloride in dioxane is then added to the resulting formate salt, and the mixture is stirred at RT for 30 min. The suspension is then concentrated under reduced pressure, and the residue is dried (Method B).

Alternatively, 1 equivalent of the Exemplary Compound 23 and 2 equivalents of the amine component are dissolved in THF and reacted at 180° C. in a single-mode microwave oven (Emrys Optimizer) for 5 min. The reaction mixture is then concentrated, and the crude product is purified by preparative HPLC (RP18 column; mobile phase: acetonitrile/water gradient with addition of 0.1% formic acid). A 4 N solution of hydrogen chloride in dioxane is then added to the resulting formate salt of the target compound, and the mixture is stirred at RT for 30 min. The suspension is then concentrated under reduced pressure, and the residue is dried (Method C).

TABLE 3

| Example No. | Structure | Yield (% of theory) [Method] | MS (ESI): [M + H]$^+$; LC-MS: $R_t$ (Method) | $^1$H-NMR (400 MHz, DMSO-d$_6$) |
|---|---|---|---|---|
| 30 | (4,4-dimethylpiperidinyl-pyrimidinyl-pyrazolone-pyridine) | 42% [A] | m/z = 351; 1.58 min (8) | δ = 9.03 (s, 1H), 8.48 (s, 1H), 8.39 (s, 1H), 8.33 (d, 1H), 8.19 (d, 1H), 7.41 (br. s, 1H), 7.34 (dd, 1H), 3.70-3.68 (m, 4H), 1.41-1.37 (m, 4H), 0.99 (s, 6H). |
| 31 | (4,4-dimethylpiperidinyl-pyrimidinyl-pyrazolone-pyridine) x HCl | 42% [B] | m/z = 351; 1.57 min (8) | δ = 9.28 (s, 1H), 8.84 (d, 1H), 8.53 (s, 1H), 8.49-8.43 (m, 2H), 7.93 (dd, 1H), 7.41 (s, 1H), 3.79-3.75 (m, 4H), 1.44-1.40 (m, 4H), 1.01 (s, 6H). |

TABLE 3-continued
| Example No. | Structure | Yield (% of theory) [Method] | MS (ESI): [M + H]+; LC-MS: R_t (Method) | $^1$H-NMR (400 MHz, DMSO-$d_6$) |
|---|---|---|---|---|
| 32 | 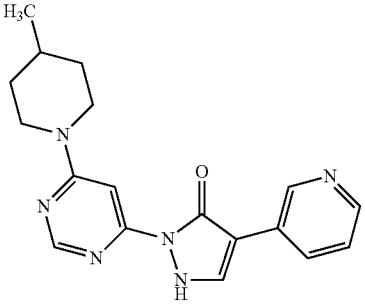 [SMILES: CC1CCN(c2cc(-n3[nH]cc(-c4cccnc4)c3=O)ncn2)CC1] | 17% [A] | m/z = 337; 2.69 min (1) | δ = 9.01 (s, 1H), 8.37 (s, 1H), 8.18 (d, 1H), 8.12 (s, 1H), 8.01 (s, 1H), 7.71 (s, 1H), 7.20 (dd, 1H), 2.94-2.90 (m, 2H), 1.71-1.53 (m, 4H), 1.30-1.27 (m, 1H), 1.18-1.01 (m, 2H), 0.99-0.83 (m, 3H). |
| 33 | 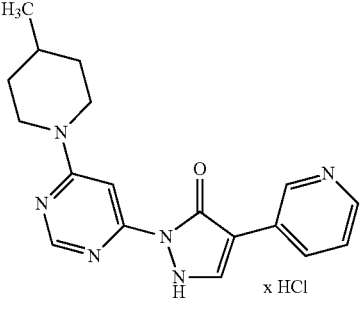 [SMILES: CC1CCN(c2cc(-n3[nH]cc(-c4cccnc4)c3=O)ncn2)CC1] | 26% [B] | m/z = 337; 1.44 min (8) | δ = 9.28 (s, 1H), 8.84 (d, 1H), 8.53 (s, 1H), 8.49-8.42 (m, 2H), 7.93 (dd, 1H), 7.42 (s, 1H), 3.13-3.11 (m, 2H), 1.85-1.69 (m, 4H), 1.28-1.05 (m, 3H), 0.95 (d, 3H). |
| 34 | 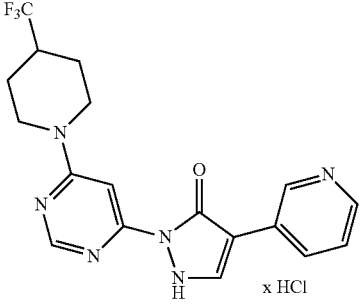 [SMILES: O=c1c(-c2cccnc2)c[nH]n1-c1cc(N2CCC(C(F)(F)F)CC2)ncn1] | 54% [B] | m/z = 391; 2.75 min (8) | δ = 9.30 (s, 1H), 8.86 (d, 1H), 8.54 (s, 2H), 8.49 (d, 1H), 7.94 (dd, 1H), 7.48 (s, 1H), 4.57-4.55 (m, 2H), 3.18-3.14 (m, 2H), 2.79-2.77 (m, 1H), 2.02-1.99 (m, 2H), 1.49-1.47 (m, 2H). |
| 35 | 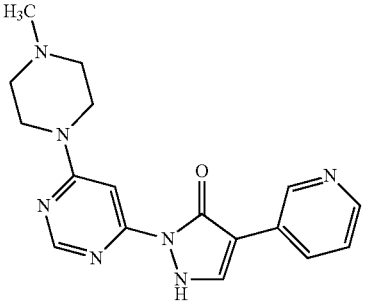 [SMILES: CN1CCN(c2cc(-n3[nH]cc(-c4cccnc4)c3=O)ncn2)CC1] | 17% [A] | m/z = 338; 0.76 min (8) | δ = 9.05 (s, 1H), 8.47 (s, 1H), 8.32 (s, 1H), 8.28 (d, 1H), 8.21 (d, 1H), 7.61 (s, 1H), 7.32 (dd, 1H), 3.74-3.71 (m, 4H), 2.60-2.57 (m, 4H), 2.34 (s, 3H). |

TABLE 3-continued

| Example No. | Structure | Yield (% of theory) [Method] | MS (ESI): [M + H]+; LC-MS: R_t (Method) | 1H-NMR (400 MHz, DMSO-d6) |
|---|---|---|---|---|
| 36 | (4-fluoropiperidinyl-pyrimidinyl-pyrazolone-pyridine) × HCl | 26% [B] | m/z = 341; 1.25 min (7) | δ = 9.28 (s, 1H), 8.86 (d, 1H), 8.55-8.53 (m, 2H), 8.48 (d, 1H), 7.97-7.90 (m, 1H), 7.50 (s, 1H), 5.09-4.89 (m, 1H), 3.91-3.72 (m, 4H), 2.07-1.90 (m, 2H), 1.89-1.76 (m, 2H). |
| 37 | (4-cyclobutylpiperazinyl-pyrimidinyl-pyrazolone-pyridine) × 2 HCl | 55% [B] | m/z = 378; 0.85 min (7) | δ = 9.30 (s, 1H), 8.86 (d, 1H), 8.65 (s, 1H), 8.60 (s, 1H), 8.54 (d, 1H), 7.98-7.89 (m, 1H), 7.60 (s, 1H), 4.64-4.46 (m, 1H), 3.13-2.82 (m, 4H), 2.42-2.27 (m, 3H), 2.21-2.08 (m, 3H), 1.82-1.60 (m, 3H), 1.30-1.22 (m, 1H). |
| 38 | (2,6-dimethylmorpholinyl-pyrimidinyl-pyrazolone-pyridine) × HCl | 65% [B] | m/z = 353; 1.24 min (8) | (500 MHz, D2O) δ = 9.05 (s, 1H), 8.67 (d, 1H), 8.47 (s, 1H), 8.34 (d, 1H), 8.17 (s, 1H), 7.94-7.85 (m, 1H), 7.07 (s, 1H), 4.02-3.94 (m, 1H), 3.84-3.73 (m, 1H), 3.36-3.29 (m, 1H), 2.98-2.75 (m, 3H), 1.29-1.21 (m, 6H). |
| 39 | (4-hydroxymethylpiperidinyl-pyrimidinyl-pyrazolone-pyridine) × HCl | 49% [C] | m/z = 353; 1.06 min (7) | δ = 9.26 (s, 1H), 8.84 (d, 1H), 8.52 (s, 1H), 8.48-8.41 (m, 2H), 7.95-7.89 (m, 1H), 7.42 (s, 1H), 4.64-4.39 (m, 1H), 3.32-3.23 (m, 3H), 3.16-3.07 (m, 1H), 1.88-1.72 (m, 3H), 1.20-1.10 (m, 1H). |

TABLE 3-continued

| Example No. | Structure | Yield (% of theory) [Method] | MS (ESI): [M + H]+; LC-MS: $R_t$ (Method) | $^1$H-NMR (400 MHz, DMSO-$d_6$) |
|---|---|---|---|---|
| 40 | 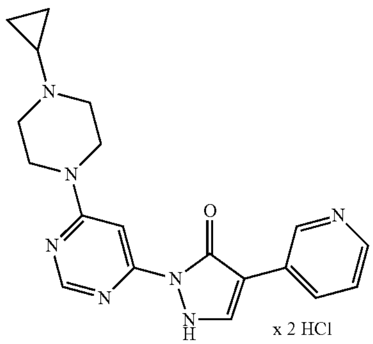 [SMILES: O=c1c(-c2cccnc2)c[nH]n1-c1cc(N2CCN(C3CC3)CC2)ncn1] | 39% [B] | m/z = 364; 0.90 min (7) | δ = 9.33 (s, 1H), 8.91 (d, 1H), 8.68 (s, 1H), 8.62 (s, 1H), 8.57 (d, 1H), 8.02-7.96 (m, 1H), 8.02-7.96 (m, 1H), 7.64 (s, 1H), 3.66-3.49 (m, 4H), 3.40-3.22 (m, 2H), 2.90-2.79 (m, 1H), 1.31-1.24 (m, 2H), 1.22-1.15 (m, 2H), 0.87-0.80 (m, 2H). |
| 41 | 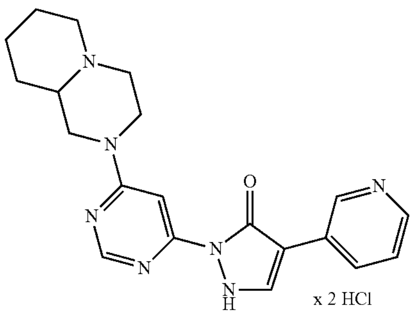 [SMILES: O=c1c(-c2cccnc2)c[nH]n1-c1cc(N2CCN3CCCCC3C2)ncn1] | 22% [C] | m/z = 378; 0.77 min (10) | δ = 9.32 (s, 1H), 8.91 (d, 1H), 8.68 (s, 1H), 8.62 (s, 1H), 8.57 (d, 1H), 8.02-7.95 (m, 1H), 7.61 (s, 1H), 4.87-4.44 (m, 1H), 3.70-2.83 (m, 8H), 2.02-1.61 (m, 4H), 1.54-1.39 (m, 2H). |

Example 42

4-(5-Bromopyridin-3-yl)-2-(6-piperidin-1-ylpyrimidin-4-yl)-1,2-dihydro-3H-pyrazol-3-one hydrochloride

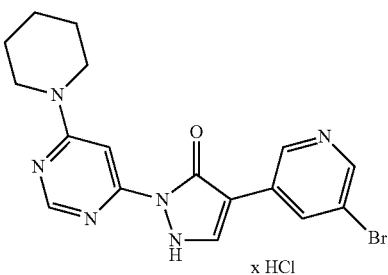 [SMILES: O=c1c(-c2cncc(Br)c2)c[nH]n1-c1cc(N2CCCCC2)ncn1]

At 100° C., 500 mg (1.7 mmol) of the compound from Example 11A, 323 mg (1.7 mmol) of the compound from Example 8A and 58 mg (0.3 mmol) of p-toluenesulfonic acid are stirred in 2 ml of ethanol for 16 h. After cooling to RT, 0.5 ml of a 4 N solution of hydrogen chloride in dioxane is added, and the mixture is stirred at RT for 30 min. The precipitate is filtered off, washed first with ethanol and then with diethyl ether and dried under reduced pressure.

Yield: 260 mg (36% of theory)

LC-MS (Method 7): $R_t$=2.22 min; MS (ESIpos): m/z=401 [M+H]+;

$^1$H-NMR (400 MHz, DMSO-$d_6$): δ=9.12 (s, 1H), 8.75 (s, 1H), 8.53-8.46 (m, 3H), 7.42 (s, 1H), 3.83-3.63 (m, 4H), 1.73-1.54 (m, 6H).

Example 43

4-(5-Bromopyridin-3-yl)-2-(6-morpholin-4-ylpyrimidin-4-yl)-1,2-dihydro-3H-pyrazol-3-one hydrochloride

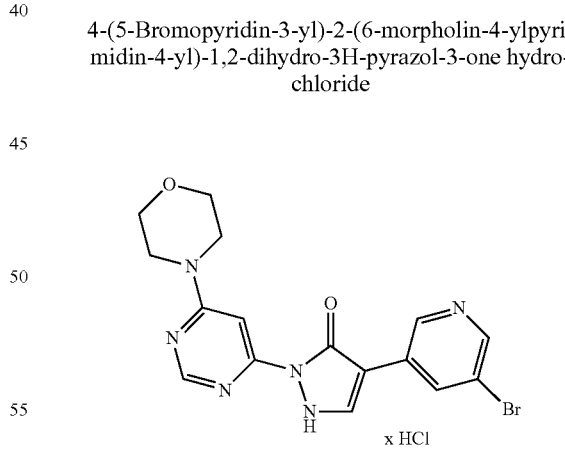

At 100° C., 500 mg (1.7 mmol) of the compound from Example 11A, 326 mg (1.7 mmol) of the compound from Example 9A and 58 mg (0.3 mmol) of p-toluenesulfonic acid are stirred in 4 ml of ethanol for 16 h. After cooling to RT, 0.5 ml of a 4 N solution of hydrogen chloride in dioxane is added, and the mixture is stirred at RT for 30 min. The precipitate is filtered off, washed first with ethanol and then with diethyl ether and dried under reduced pressure.

Yield: 235 mg (32% of theory)

LC-MS (Method 7): R$_t$=1.85 min; MS (ESIpos): m/z=403 [M+H]$^+$;
$^1$H-NMR (400 MHz, DMSO-d$_6$): δ=9.12 (s, 1H), 8.73 (s, 1H), 8.56-8.50 (m, 3H), 7.49 (s, 1H), 3.75-3.67 (m, 8H).

Example 44

5-[3-oxo-2-(6-piperidin-1-ylpyrimidin-4-yl)-2,3-dihydro-1H-pyrazol-4-yl]pyridine-3-carbonitrile hydrochloride

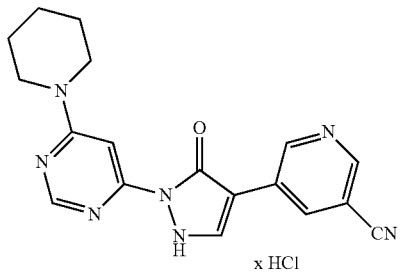 [SMILES: N#Cc1cncc(-c2c[nH]n(-c3cc(N4CCCCC4)ncn3)c2=O)c1]

100 mg (0.2 mmol) of the compound from Example 42, 20 mg (0.2 mmol) of zinc cyanide and 8 mg (0.007 mmol) of tetrakis(triphenylphosphine)palladium in 2 ml DMF are reacted for a total of 75 min at 220° C. in a single-mode microwave oven (Emrys Optimizer). After cooling to RT, the reaction mixture is concentrated under reduced pressure and the residue is taken up in formic acid and purified by preparative HPLC (RP18 column; mobile phase: acetonitrile/water gradient with 0.1% formic acid added to the water). The resulting formate salt is converted by addition of 0.5 ml of a 4 N solution of hydrogen chloride in dioxane into the hydrochloride. The product is washed first with ethyl acetate and then with diethyl ether and dried under reduced pressure.

Yield: 22 mg (25% of theory)
LC-MS (Method 7): R$_t$=1.97 min; MS (ESIpos): m/z=348 [M+H]$^+$;
$^1$H-NMR (400 MHz, DMSO-d$_6$): δ=9.34 (s, 1H), 8.73-8.59 (m, 2H), 8.54-8.37 (m, 2H), 7.41 (s, 1H), 3.77-3.58 (m, 4H), 1.75-1.49 (m, 6H).

Example 45

5-[2-(6-Morpholin-4-ylpyrimidin-4-yl)-3-oxo-2,3-dihydro-1H-pyrazol-4-yl]pyridine-3-carbonitrile hydrochloride

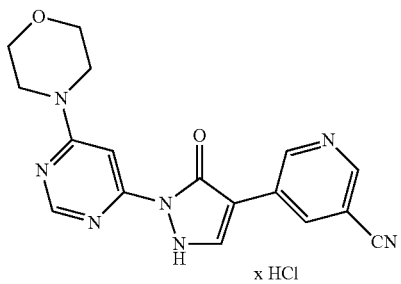 [SMILES: N#Cc1cncc(-c2c[nH]n(-c3cc(N4CCOCC4)ncn3)c2=O)c1]

100 mg (0.2 mmol) of the compound from Example 43, 20 mg (0.2 mmol) of zinc cyanide and 8 mg (0.007 mmol) of tetrakis(triphenylphosphine)palladium in 2 ml DMF are reacted at 220° C. in a single-mode microwave oven (Emrys Optimizer) for a total of 105 min. After cooling to RT, the reaction mixture is concentrated under reduced pressure and the residue is taken up in formic acid and purified by preparative HPLC (RP18 column; mobile phase: acetonitrile/water gradient with 0.1% formic acid added to the water). The resulting formate salt is converted into the hydrochloride by addition of 0.5 ml of a 4 N solution of hydrogen chloride in dioxane.

Yield: 11 mg (13% of theory)
LC-MS (Method 7): R$_t$=1.64 min; MS (ESIpos): m/z=350 [M+H]$^+$;
$^1$H-NMR (400 MHz, DMSO-d$_6$): δ=9.36 (s, 1H), 8.75-8.64 (m, 2H), 8.59-8.49 (m, 2H), 7.49 (s, 1H), 3.76-3.65 (m, 8H).

Example 46

2-Pyrazin-2-yl-4-pyridin-3-yl-1,2-dihydro-3H-pyrazol-3-one hydrochloride

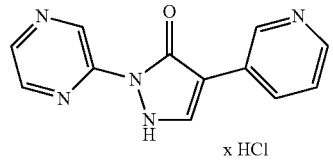 [SMILES: O=c1c(-c2cccnc2)c[nH]n1-c1cnccn1]

441 mg (2.0 mmol) of the compound from Example 12A and 220 mg (2.0 mmol) of the compound from Example 3A are initially charged in 10 ml of ethanol. 93 mg (0.4 mmol) of camphor-10-sulfonic acid are added, and the mixture is stirred under reflux for 5 h. The mixture is allowed to cool to RT, and the solid formed is filtered off and washed once with a little ethanol. 10 ml of a 4 N solution of hydrogen chloride in dioxane are then added, and the mixture is stirred at RT for 30 min. The mixture is then concentrated on a rotary evaporator, and the residue is dried under high vacuum.

Yield: 260 mg (47% of theory)
LC-MS (Method 1): R$_t$=1.93 min; MS (ESIpos): m/z=240 [M+H]$^+$;
$^1$H-NMR (400 MHz, DMSO-d$_6$): δ=9.70 (s, 1H), 9.43 (s, 1H), 9.08 (d, 1H), 9.01 (s, 1H), 8.70 (d, 1H), 8.61 (s, 2H), 8.08 (dd, 1H).

Example 47

4-Pyridin-3-yl-2-quinoxalin-2-yl-1,2-dihydro-3H-pyrazol-3-one hydrochloride

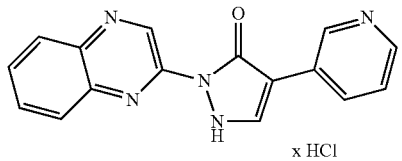 [SMILES: O=c1c(-c2cccnc2)c[nH]n1-c1cnc2ccccc2n1]

1.5 g (6.8 mmol) of the compound from Example 3A and 1.0 g (6.8 mmol) of the compound from Example 13A are initially charged in 35 ml of ethanol. 316 mg (1.4 mmol) of camphor-10-sulfonic acid are added, and the mixture is stirred under reflux for 6 h. The mixture is then cooled to 0° C., and the solid formed is filtered off and washed with ethanol. 10 ml of a 4 N solution of hydrogen chloride in dioxane are then added, and the mixture is stirred at RT for 30 min. The mixture is then concentrated on a rotary evaporator, and the residue is dried under high vacuum.

Yield: 470 mg (21% of theory)

LC-MS (Method 11): $R_t$=1.22 min; MS (ESIpos): m/z=290 [M+H]$^+$;

$^1$H-NMR (400 MHz, DMSO-d$_6$): δ=10.03 (s, 1H), 9.45 (s, 1H), 9.10-9.05 (m, 2H), 8.70 (d, 1H), 8.14 (d, 1H), 8.11-8.02 (m, 2H), 7.92 (dd, 1H), 7.85 (dd, 1H).

Example 48

4-Pyridin-3-yl-2-quinolin-2-yl-1,2-dihydro-3H-pyrazol-3-one hydrochloride

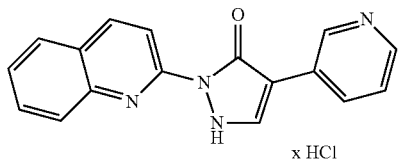 [SMILES: O=c1c(-c2cccnc2)c[nH]n1-c1ccc2ccccc2n1]

750 mg (3.4 mmol) of the compound from Example 14A and 542 mg (3.4 mmol) of the compound from Example 3A are initially charged in 17.5 ml of ethanol. 130 mg (0.7 mmol) of p-toluenesulfonic acid are added, and the mixture is stirred under reflux for 16 h. The mixture is then allowed to cool and concentrated on a rotary evaporator. The residue is stirred in a mixture of 6 ml of DMSO and 10 ml of water for 30 min, and the solid is filtered off and dried under high vacuum. 10 ml of a 4 N solution of hydrogen chloride in dioxane are then added, and the mixture is stirred at RT for 30 min. The mixture is then concentrated on a rotary evaporator, and the residue is dried under high vacuum.

Yield: 750 mg (65% of theory)

LC-MS (Method 12): $R_t$=1.14 min; MS (ESIpos): m/z=289 [M+H]$^+$;

$^1$H-NMR (400 MHz, DMSO-d$_6$): δ=9.40 (s, 1H), 9.03 (d, 1H), 8.85 (s, 1H), 8.71-8.57 (m, 3H), 8.12-8.02 (m, 3H), 7.88 (dd, 1H), 7.64 (dd, 1H).

Example 49

2-(6-Azetidin-1-ylpyrimidin-4-yl)-4-pyridin-3-yl-1,2-dihydro-3H-pyrazol-3-one

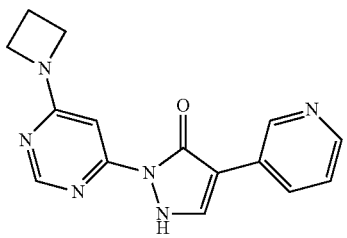 [SMILES: O=c1c(-c2cccnc2)c[nH]n1-c1cc(N2CCC2)ncn1]

150 mg (0.5 mmol) of the compound from Example 23 and 63 mg (1 1 mmol) of azetidine are suspended in 4 ml of ethanol and reacted at 120° C. in a single-mode microwave oven (CEM Explorer) for 40 min. The solid is filtered off, washed twice with in each case 0.5 ml of ethanol and discarded. The mother liquor is combined with the wash solutions, and the solvent is removed on a rotary evaporator. The residue is purified by preparative HPLC (RP18 column; mobile phase: acetonitrile/water gradient with addition of 0.1% TFA). The product-containing fractions are combined and concentrated on a rotary evaporator. The residue is stirred under reflux in ethanol for 20 min and then filtered off while still hot. The solid obtained is dried under high vacuum.

Yield: 45 mg (28% of theory)

LC-MS (Method 9): $R_t$=0.38 min; MS (ESIpos): m/z=295 [M+H]$^+$;

$^1$H-NMR (400 MHz, DMSO-d$_6$): δ=9.19 (s, 1H), 8.64 (d, 1H), 8.45 (s, 1H), 8.41 (d, 2H), 7.75 (dd, 1H), 6.88 (s, 1H), 4.20 (dd, 4H), 2.46-2.38 (m, 2H).

Example 50

2-[6-(3-Hydroxyazetidin-1-yl)pyrimidin-4-yl]-4-pyridin-3-yl-1,2-dihydro-3H-pyrazol-3-one hydrochloride

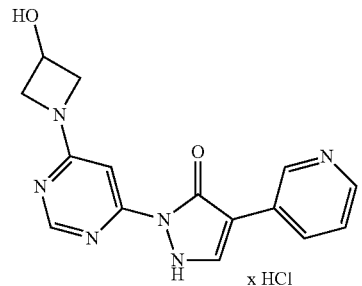 [SMILES: O=c1c(-c2cccnc2)c[nH]n1-c1cc(N2CC(O)C2)ncn1]

100 mg (0.4 mmol) of the compound from Example 23, 94 mg (0.7 mmol) of N,N-diisopropylethylamine and 80 mg (0.7 mmol) of azetidin-3-ol hydrochloride are suspended in 3 ml of THF and reacted at 120° C. in a single-mode microwave oven (CEM Explorer) for 20 min. 2 ml of ethanol are then added, and the mixture is again reacted in a single-mode microwave oven (CEM Explorer) for 20 min. The mixture is then reacted initially at 120° C. for a further 60 min and then at 175° C. for 60 min in a single-mode microwave oven (CEM Explorer). The mixture is then separated directly by preparative HPLC (RP18 column; mobile phase: acetonitrile/water gradient with addition of 0.1% TFA). The product-containing fractions are combined and concentrated on a rotary evaporator, and the residue is dried under high vacuum. The residue is then stirred in 5 ml of a 4 N solution of hydrogen chloride in dioxane for 30 min. The solid is filtered off, washed with tert-butyl methyl ether and dried under high vacuum.

Yield: 26 mg (20% of theory)

LC-MS (Method 7): $R_t$=0.92 min; MS (ESIpos): m/z=311 [M+H]$^+$;

$^1$H-NMR (400 MHz, DMSO-d$_6$): δ=9.25 (s, 1H), 8.84 (d, 1H), 8.50-8.42 (m, 3H), 7.94 (dd, 1H), 6.93 (s, 1H), 4.70-4.62 (m, 1H), 4.43 (dd, 2H), 3.95 (dd, 2H).

Example 51

2-[6-(3,3-Difluoroazetidin-1-yl)pyrimidin-4-yl]-4-pyridin-3-yl-1,2-dihydro-3H-pyrazol-3-one hydrochloride

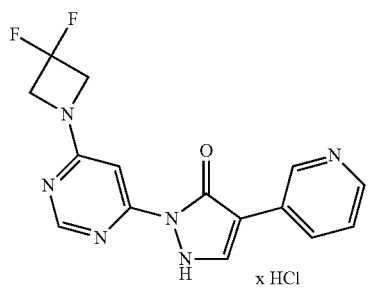 [SMILES: O=c1c(-c2cccnc2)c[nH]n1-c1cc(N2CC(F)(F)C2)ncn1]

100 mg (0.4 mmol) of the compound from Example 23, 94 mg (0.7 mmol) of N,N-diisopropylethylamine and 95 mg (0.731 mmol) of 3,3-difluoroazetidine hydrochloride are suspended in 3 ml of ethanol and reacted at 120° C. in a single-mode microwave oven (CEM Explorer) for 40 min. The solvent is then removed, and the residue is taken up in 6 ml of DMSO. Undissolved components are removed by filtration, and the solution obtained is purified by preparative HPLC (RP18 column; mobile phase: acetonitrile/water gradient with addition of 0.1% TFA). The product-containing fractions are combined and concentrated on a rotary evaporator, and the residue is dried under high vacuum. The residue is then stirred in 5 ml of a 4 N solution of hydrogen chloride in dioxane for 30 min. The solid is filtered off, washed with tert-butyl methyl ether and dried under high vacuum.

Yield: 64 mg (44% of theory)

LC-MS (Method 7): $R_t$=1.13 min; MS (ESIpos): m/z=331 [M+H]$^+$;

$^1$H-NMR (400 MHz, DMSO-d$_6$): δ=9.32 (s, 1H), 8.91 (d, 1H), 8.68 (s, 1H), 8.60-8.53 (m, 2H), 7.97 (dd, 1H), 7.26 (s, 1H), 4.66 (dd, 4H).

Example 52 tert-Butyl {1-[6-(5-oxo-4-pyridin-3-yl-2,5-dihydro-1H-pyrazol-1-yl)pyrimidin-4-yl]azetidin-3-yl}-carbamate

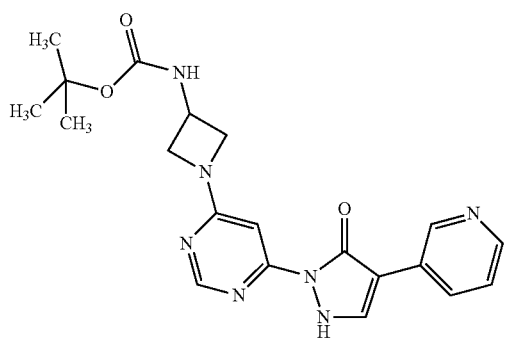 [SMILES: CC(C)(C)OC(=O)NC1CN(c2cc(-n3[nH]cc(-c4cccnc4)c3=O)ncn2)C1]

200 mg (0.7 mmol) of the compound from Example 23 and 252 mg (1.5 mmol) of tert-butyl azetidin-3-ylcarbamate are suspended in 6 ml of ethanol and reacted at 120° C. in a single-mode microwave oven (CEM Explorer) for 40 min. The solid formed is filtered off, washed twice with in each case 0.5 ml of ethanol and dried under high vacuum.

Yield: 227 mg (76% of theory)

LC-MS (Method 9): $R_t$=0.72 min; MS (ESIpos): m/z=410 [M+H]$^+$;

$^1$H-NMR (400 MHz, DMSO-d$_6$): δ=9.05 (s, 1H), 9.45 (s, 1H), 9.40 (s, 1H), 9.32 (d, 1H), 8.20 (d, 1H), 7.67 (d, 1H), 7.36 (dd, 1H), 4.55-4.45 (m, 1H), 4.35 (t, 2H), 3.98-3.91 (m, 2H), 1.40 (s, 9H).

Example 53

2-[6-(3-Aminoazetidin-1-yl)pyrimidin-4-yl]-4-pyridin-3-yl-1,2-dihydro-3H-pyrazol-3-one bistrifluoroacetate

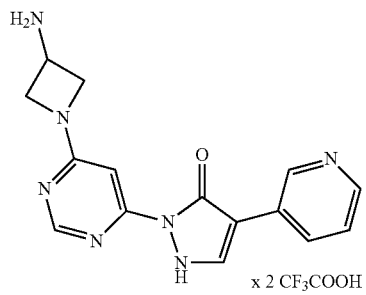 [SMILES: NC1CN(c2cc(-n3[nH]cc(-c4cccnc4)c3=O)ncn2)C1]

200 mg (0.5 mmol) of the compound from Example 52 are dissolved in 5 ml of dichloromethane, 111 mg (1.0 mmol) of TFA are added and the mixture is stirred at RT for 18 h. A further 1.10 g (9.8 mmol) of TFA are added, and the mixture is again stirred at RT for 5 h. The mixture is then concentrated on a rotary evaporator, and the residue is stirred twice in succession in dichloromethane, by adding 5 ml of dichloromethane each time and then concentrating again on a rotary evaporator. In the same manner, the mixture is then stirred twice in tert-butyl methyl ether and once in methanol, and the residue is then dried under high vacuum.

Yield: 249 mg (95% of theory)

LC-MS (Method 7): $R_t$=0.72 min; MS (ESIpos): m/z=310 [M+H]$^+$;

$^1$H-NMR (400 MHz, DMSO-d$_6$): δ=9.24 (s, 1H), 8.71 (d, 1H), 8.60-8.51 (m, 3H), 8.47 (d, 1H), 7.77 (dd, 1H), 7.10 (s, 1H), 4.46 (dd, 2H), 4.25-4.15 (m, 3H).

Example 54

2-[6-(3-Aminoazetidin-1-yl)pyrimidin-4-yl]-4-pyridin-3-yl-1,2-dihydro-3H-pyrazol-3-one dihydrochloride

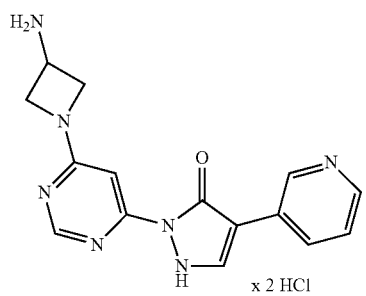 [SMILES: NC1CN(c2cc(-n3[nH]cc(-c4cccnc4)c3=O)ncn2)C1]

278 mg (0.5 mmol) of the compound from Example 53 are stirred in 10 ml of a 4 N solution of hydrogen chloride in dioxane for 30 min. The solid is then filtered off, washed twice in each case with 0.5 ml of tert-butyl methyl ether and dried under high vacuum.

Yield: 188 mg (95% of theory)

LC-MS (Method 7): $R_t$=0.74 min; MS (ESIpos): m/z=310 [M+H]$^+$;

$^1$H-NMR (400 MHz, DMSO-d$_6$): δ=9.29 (s, 1H), 8.89-8.75 (m, 4H), 8.59 (s, 1H), 8.55 (s, 1H), 8.51 (d, 1H), 7.95 (dd, 1H), 7.10 (s, 1H), 4.50-4.42 (m, 2H), 4.28-4.20 (m, 3H).

Example 55

2-(6-{[6-(Diethylamino)hexyl]amino}pyrimidin-4-yl)-4-pyridin-3-yl-1,2-dihydro-3H-pyrazol-3-one

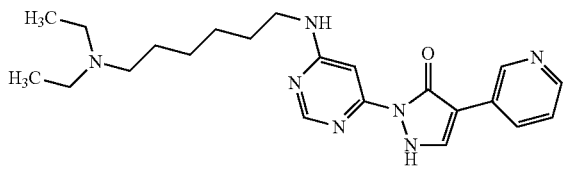 [SMILES: CCN(CC)CCCCCCNc1cc(-n2[nH]cc(-c3cccnc3)c2=O)ncn1]

2.7 g (10.0 mmol) of the Exemplary Compound 23 are dissolved in 60 ml of n-butanol and provided as a stock solution.

17 mg (0.1 mmol) of N,N-diethylhexane-1,6-diamine are initially charged, and 600 μl (0.1 mmol) of the above stock solution and 35 μl (26 mg, 0.2 mmol) of N,N-diisopropylethylamine (Hünig-Base) are added in succession. The reaction mixture is stirred at 120° C. for 16 h. For work-up, the n-butanol is evaporated. The residue is taken up in DMSO and filtered. The filtrate is purified by preparative LC-MS (Method 13). The product fractions are concentrated under reduced pressure, and the residue is dried.

Yield: 3 mg (7% of theory)

LC-MS (Method 13): $R_t$=1.24 min; MS (ESIpos): m/z=410 [M+H]$^+$.

Analogoulsy to the procedure of Example 55, the compounds listed in Table 4 are prepared from 0.1 mmol of the Exemplary Compound 23 and 0.1 mmol of the appropriate amine:

TABLE 4

| Example No. | Structure | Yield (% of theory) | MS (ESI): [M + H]$^+$; LC-MS: $R_t$ (Method 13) |
|---|---|---|---|
| 56 | 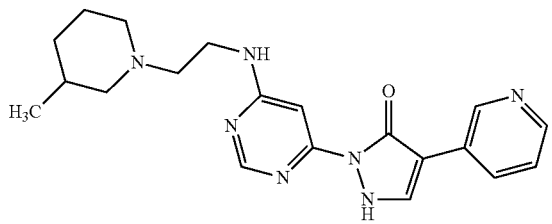 [SMILES: CC1CCCN(CCNc2cc(-n3[nH]cc(-c4cccnc4)c3=O)ncn2)C1] | 15% | m/z = 380; 1.19 min |
| 57 | 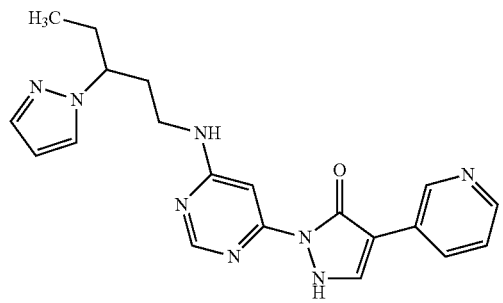 [SMILES: CCC(CCNc1cc(-n2[nH]cc(-c3cccnc3)c2=O)ncn1)n1cccn1] | 28% | m/z = 391; 1.52 min |
| 58 | 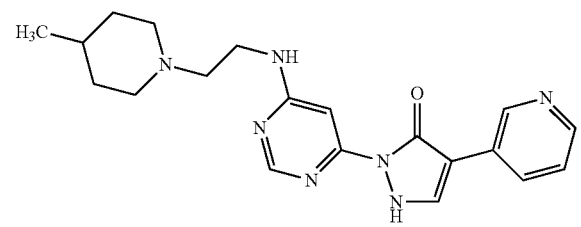 [SMILES: CC1CCN(CCNc2cc(-n3[nH]cc(-c4cccnc4)c3=O)ncn2)CC1] | 6% | m/z = 380; 0.30 min |

TABLE 4-continued

| Example No. | Structure | Yield (% of theory) | MS (ESI): [M + H]+; LC-MS: R$_t$ (Method 13) |
|---|---|---|---|
| 59 | 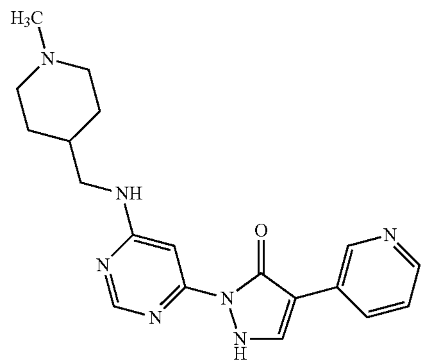 [SMILES: CN1CCC(CNc2cc(-n3[nH]cc(-c4cccnc4)c3=O)ncn2)CC1] | 7% | m/z = 366; 0.30 min |
| 60 | 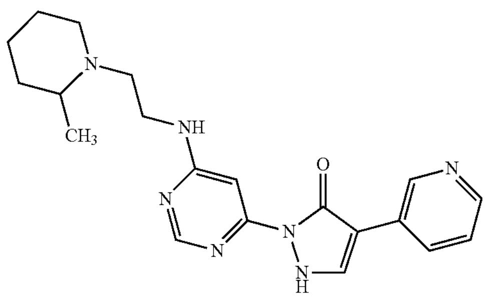 [SMILES: CC1CCCCN1CCNc1cc(-n2[nH]cc(-c3cccnc3)c2=O)ncn1] | 20% | m/z = 380; 1.18 min |
| 61 | 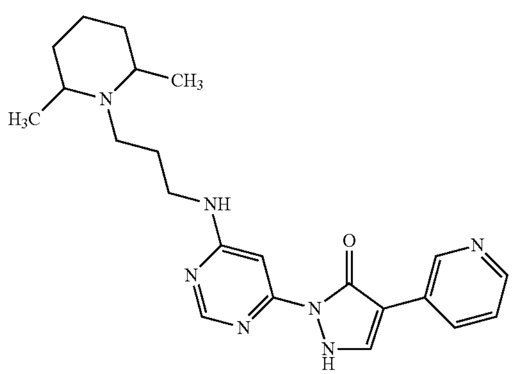 [SMILES: CC1CCCC(C)N1CCCNc1cc(-n2[nH]cc(-c3cccnc3)c2=O)ncn1] | 26% | m/z = 408; 1.20 min |
| 62 | 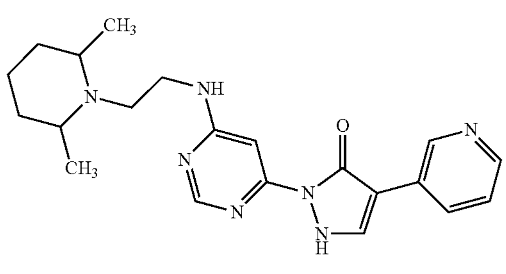 [SMILES: CC1CCCC(C)N1CCNc1cc(-n2[nH]cc(-c3cccnc3)c2=O)ncn1] | 12% | m/z = 394; 1.21 min |

TABLE 4-continued

| Example No. | Structure | Yield (% of theory) | MS (ESI): [M + H]+; LC-MS: R_t (Method 13) |
|---|---|---|---|
| 63 | 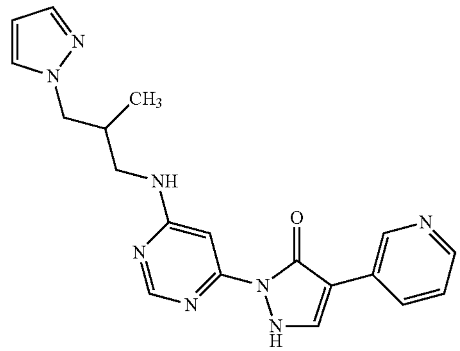 [SMILES: CC(CNc1cc(-n2[nH]cc(-c3cccnc3)c2=O)ncn1)Cn1cccn1] | 34% | m/z = 377; 1.41 min |
| 64 | 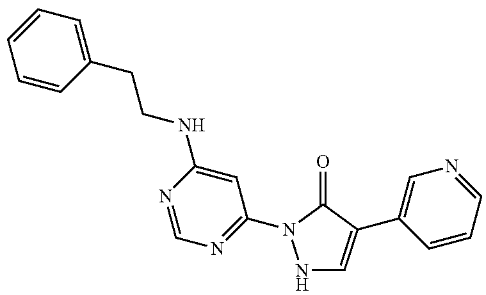 [SMILES: O=c1c(-c2cccnc2)c[nH]n1-c1cc(NCCc2ccccc2)ncn1] | 15% | m/z = 359; 1.57 min |
| 65 | 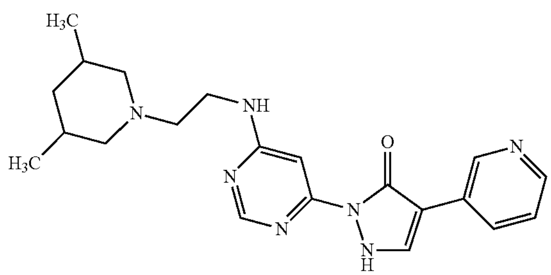 [SMILES: CC1CC(C)CN(CCNc2cc(-n3[nH]cc(-c4cccnc4)c3=O)ncn2)C1] | 22% | m/z = 394; 1.21 min |
| 66 | 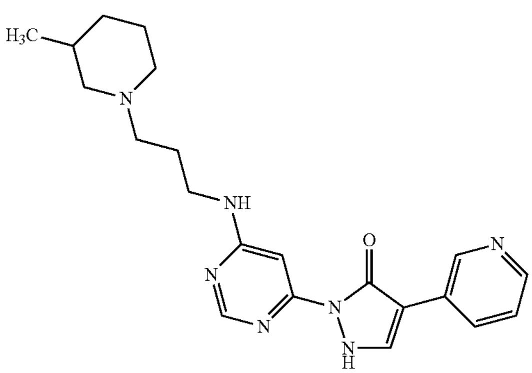 [SMILES: CC1CCCN(CCCNc2cc(-n3[nH]cc(-c4cccnc4)c3=O)ncn2)C1] | 62% | m/z = 394; 1.20 min |
| 67 | 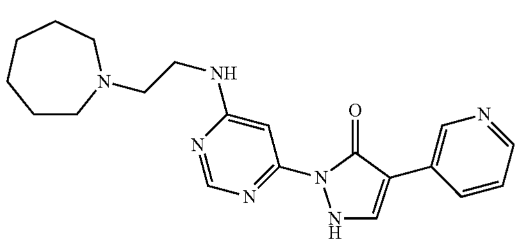 [SMILES: O=c1c(-c2cccnc2)c[nH]n1-c1cc(NCCN2CCCCCC2)ncn1] | 18% | m/z = 379; 1.18 min |

TABLE 4-continued

| Example No. | Structure | Yield (% of theory) | MS (ESI): [M + H]⁺; LC-MS: R$_t$ (Method 13) |
|---|---|---|---|
| 68 | 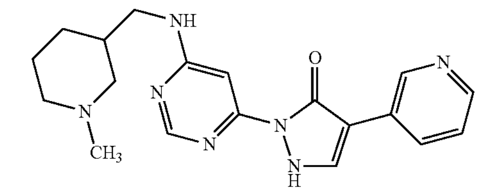 [SMILES: CN1CCCC(CNc2cc(-n3[nH]cc(-c4cccnc4)c3=O)ncn2)C1] | 24% | m/z = 366; 1.16 min |
| 69 | 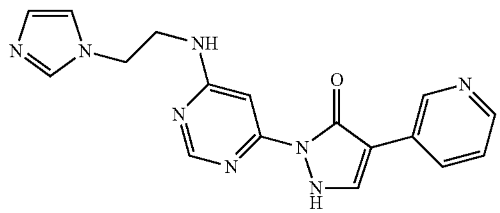 [SMILES: O=c1c(-c2cccnc2)c[nH]n1-c1cc(NCCn2ccnc2)ncn1] | 5% | m/z = 349; 0.30 min |
| 70 | 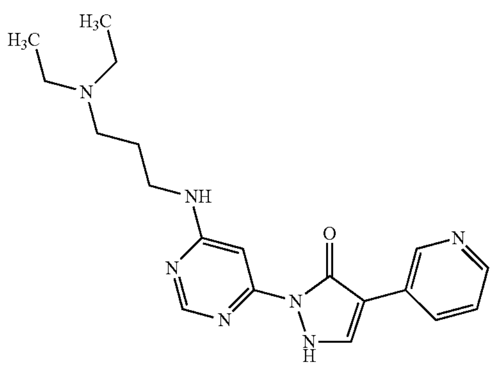 [SMILES: CCN(CC)CCCNc1cc(-n2[nH]cc(-c3cccnc3)c2=O)ncn1] | 4% | m/z = 368; 0.30 min |
| 71 | 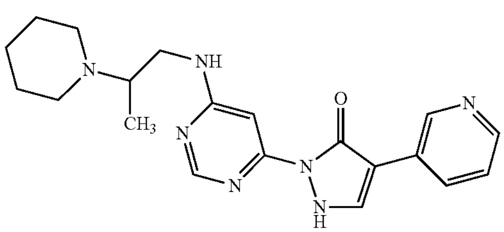 [SMILES: CC(CNc1cc(-n2[nH]cc(-c3cccnc3)c2=O)ncn1)N1CCCCC1] | 25% | m/z = 380; 1.18 min |
| 72 | 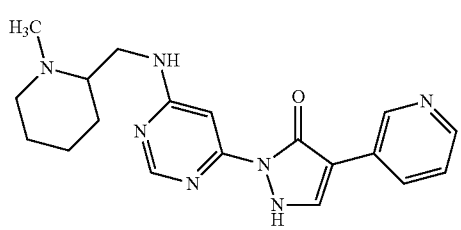 [SMILES: CN1CCCCC1CNc1cc(-n2[nH]cc(-c3cccnc3)c2=O)ncn1] | 14% | m/z = 366; 0.30 min |

TABLE 4-continued
| Example No. | Structure | Yield (% of theory) | MS (ESI): [M + H]+; LC-MS: $R_t$ (Method 13) |
|---|---|---|---|
| 73 | 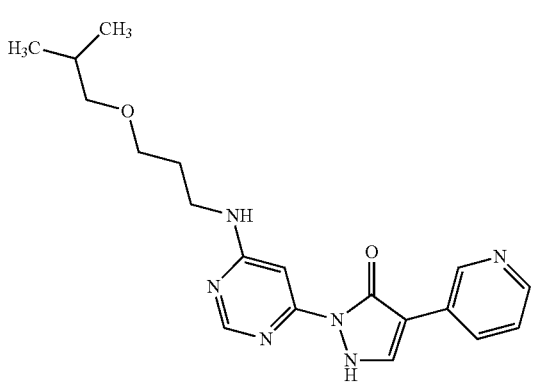 [SMILES: CC(C)COCCCNc1cc(-n2[nH]cc(-c3cccnc3)c2=O)ncn1] | 2% | m/z = 369; 1.57 min |
| 74 | 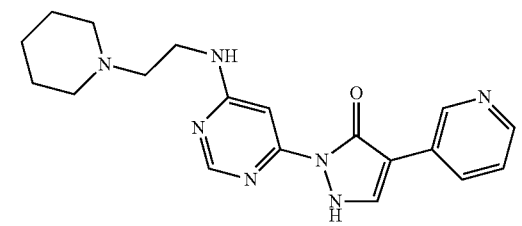 [SMILES: O=c1c(-c2cccnc2)c[nH]n1-c1cc(NCCN2CCCCC2)ncn1] | 27% | m/z = 366; 1.13 min |
| 75 | 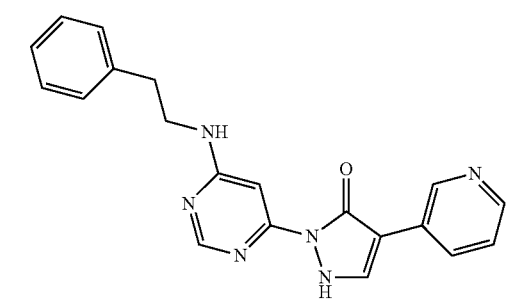 [SMILES: O=c1c(-c2cccnc2)c[nH]n1-c1cc(NCCc2ccccc2)ncn1] | 5% | m/z = 359; 1.56 min |
| 76 | 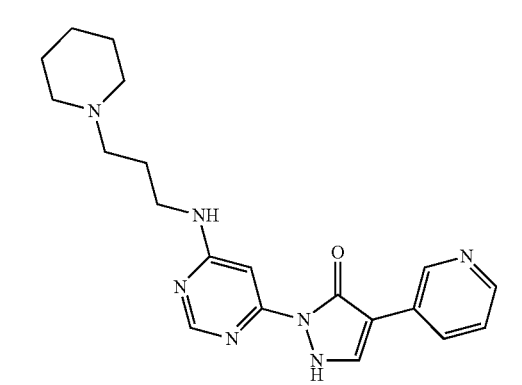 [SMILES: O=c1c(-c2cccnc2)c[nH]n1-c1cc(NCCCN2CCCCC2)ncn1] | 25% | m/z = 380; 1.14 min |

TABLE 4-continued

| Example No. | Structure | Yield (% of theory) | MS (ESI): [M + H]+; LC-MS: $R_t$ (Method 13) |
|---|---|---|---|
| 77 | 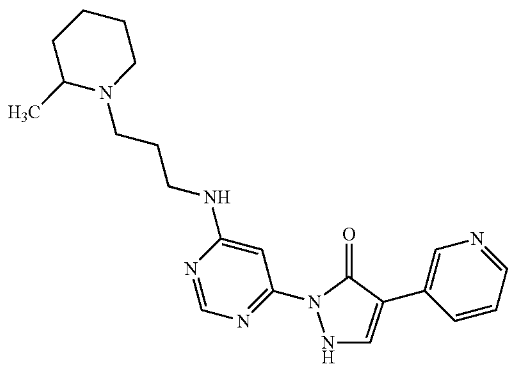 [SMILES: CC1CCCCN1CCCNc1cc(-n2[nH]cc(-c3cccnc3)c2=O)ncn1] | 18% | m/z = 394; 1.17 min |
| 78 | 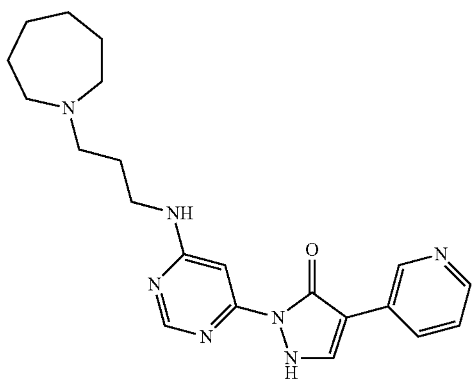 [SMILES: O=c1c(-c2cccnc2)c[nH]n1-c1cc(NCCCN2CCCCCC2)ncn1] | 30% | m/z = 394; 1.18 min |
| 79 | 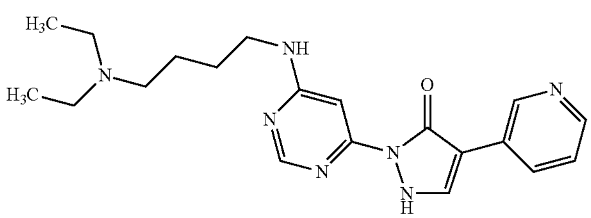 [SMILES: CCN(CC)CCCCNc1cc(-n2[nH]cc(-c3cccnc3)c2=O)ncn1] | 6% | m/z = 382; 0.30 min |
| 80 | 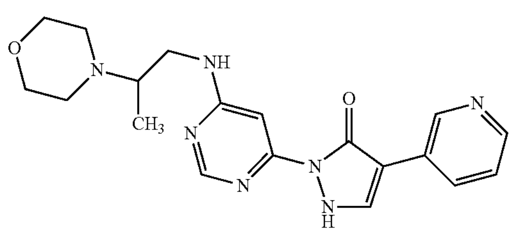 [SMILES: CC(CNc1cc(-n2[nH]cc(-c3cccnc3)c2=O)ncn1)N1CCOCC1] | 11% | m/z = 382; 0.30 min |
| 81 | 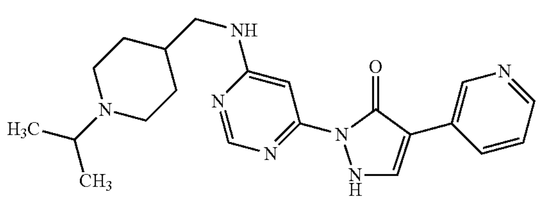 [SMILES: CC(C)N1CCC(CNc2cc(-n3[nH]cc(-c4cccnc4)c3=O)ncn2)CC1] | 24% | m/z = 393; 1.18 min |

TABLE 4-continued

| Example No. | Structure | Yield (% of theory) | MS (ESI): [M + H]+; LC-MS: R_t (Method 13) |
|---|---|---|---|
| 82 | 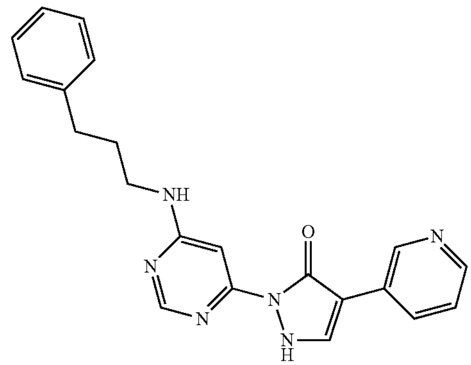 [SMILES: O=c1c(-c2cccnc2)c[nH]n1-c1cc(NCCCc2ccccc2)ncn1] | 12% | m/z = 373; 1.64 min |
| 83 | 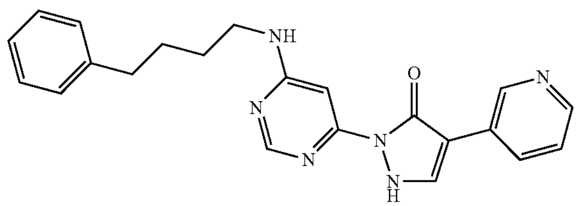 [SMILES: O=c1c(-c2cccnc2)c[nH]n1-c1cc(NCCCCc2ccccc2)ncn1] | 11% | m/z = 387; 1.71 min |
| 84 | 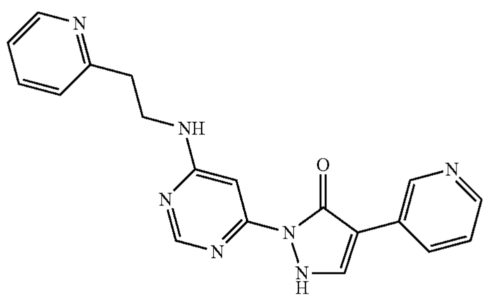 [SMILES: O=c1c(-c2cccnc2)c[nH]n1-c1cc(NCCc2ccccn2)ncn1] | 20% | m/z = 360; 1.18 min |
| 85 | 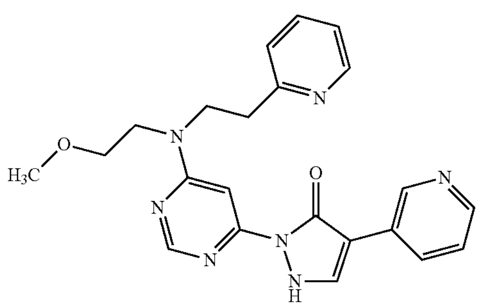 [SMILES: COCCN(CCc1ccccn1)c1cc(-n2[nH]cc(-c3cccnc3)c2=O)ncn1] | 9% | m/z = 418; 1.28 min |
| 86 | 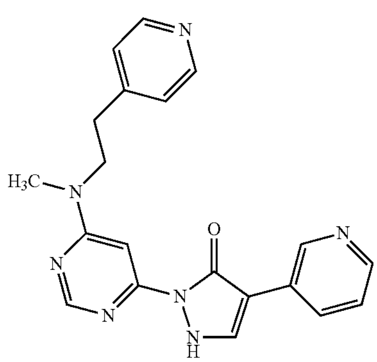 [SMILES: CN(CCc1ccncc1)c1cc(-n2[nH]cc(-c3cccnc3)c2=O)ncn1] | 16% | m/z = 374; 1.19 min |

TABLE 4-continued

| Example No. | Structure | Yield (% of theory) | MS (ESI): [M + H]+; LC-MS: R_t (Method 13) |
|---|---|---|---|
| 87 | 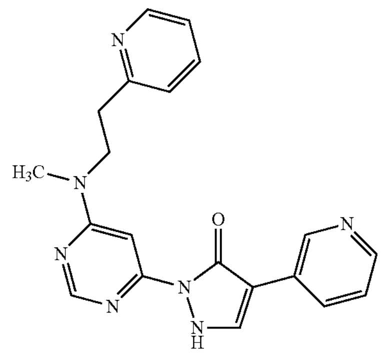 [SMILES: CN(CCc1ccccn1)c1cc(-n2[nH]cc(-c3cccnc3)c2=O)ncn1] | 12% | m/z = 374; 1.21 min |

Example 88

2-[6-(3-Phenylpropoxy)pyrimidin-4-yl]-4-pyridin-3-yl-1,2-dihydro-3H-pyrazol-3-one

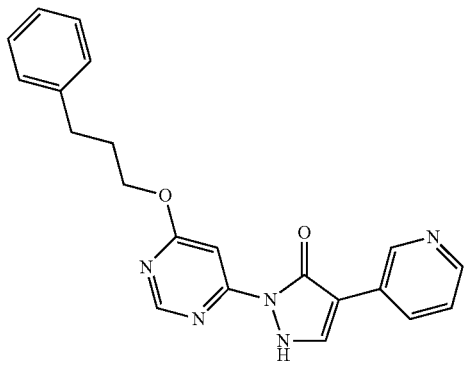 [SMILES: O=c1c(-c2cccnc2)c[nH]n1-c1cc(OCCCc2ccccc2)ncn1]

2.3 g (10.0 mmol) of the Exemplary Compound 23 are dissolved in 30 ml of THF and provided as a stock solution.

5 mg (0.1 mmol) of sodium hydride (60% in mineral oil) are added to a solution of 14 mg (0.1 mmol) of 3-phenylpropan-1-ol in 300 μl of THF, and the mixture is shaken at RT for 10 min. After addition of 300 μl (0.1 mmol) of the above stock solution and 2 mg (0.1 mmol) of tetra-n-butylammonium iodide, the reaction mixture is stirred at RT for 16 h. For work-up, the solvent is evaporated. The residue is taken up in DMSO and filtered. The filtrate is purified by preparative LC-MS (Method 13). The product fractions are concentrated under reduced pressure, and the residue is dried.

Yield: 4 mg (10% of theory)

LC-MS (Method 13): R_t=1.85 min; MS (ESIpos): m/z=374 [M+H]+.

Analogously to the procedure of Example 88, the compounds listed in Table 5 are prepared from 0.1 mmol of the Exemplary Compound 23 and 0.1 mmol of the appropriate alcohol:

TABLE 5

| Example No. | Structure | Yield (% of theory) | MS (ESI): [M + H]+; LC-MS: R_t (Method 13) |
|---|---|---|---|
| 89 | 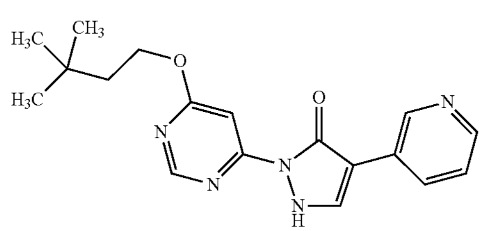 [SMILES: CC(C)(C)CCOc1cc(-n2[nH]cc(-c3cccnc3)c2=O)ncn1] | 15% | m/z = 340; 1.91 min |

TABLE 5-continued

| Example No. | Structure | Yield (% of theory) | MS (ESI): [M + H]⁺; LC-MS: R_t (Method 13) |
|---|---|---|---|
| 90 | 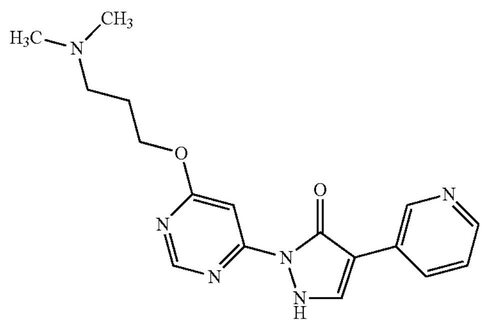 [SMILES: CN(C)CCCOc1cc(-n2[nH]cc(-c3cccnc3)c2=O)ncn1] | 2% | m/z = 341; 0.30 min |
| 91 | 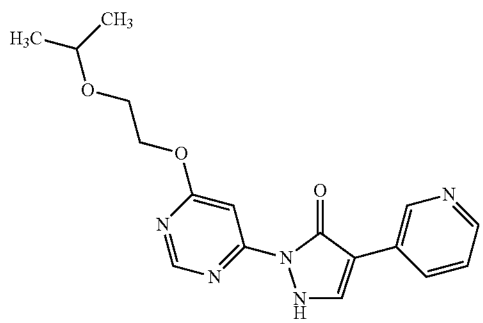 [SMILES: CC(C)OCCOc1cc(-n2[nH]cc(-c3cccnc3)c2=O)ncn1] | 27% | m/z = 342; 1.47 min |
| 92 | 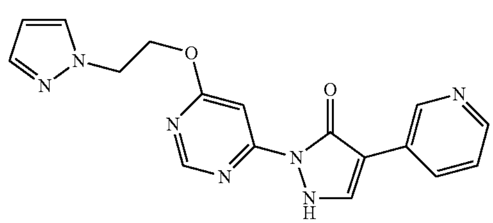 [SMILES: O=c1c(-c2cccnc2)c[nH]n1-c1cc(OCCn2cccn2)ncn1] | 3% | m/z = 350; 1.37 min |
| 93 | 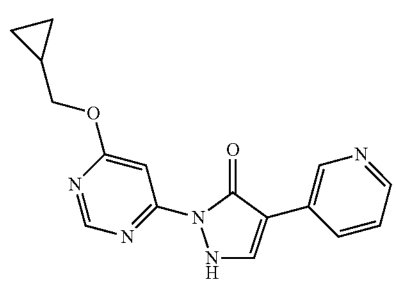 [SMILES: O=c1c(-c2cccnc2)c[nH]n1-c1cc(OCC2CC2)ncn1] | 7% | m/z = 310; 1.52 min |
| 94 | 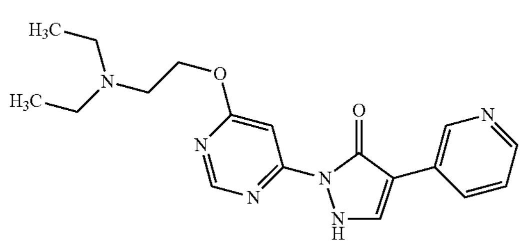 [SMILES: CCN(CC)CCOc1cc(-n2[nH]cc(-c3cccnc3)c2=O)ncn1] | 4% | m/z = 355; 1.09 min |

TABLE 5-continued

| Example No. | Structure | Yield (% of theory) | MS (ESI): [M + H]+; LC-MS: R$_t$ (Method 13) |
|---|---|---|---|
| 95 | 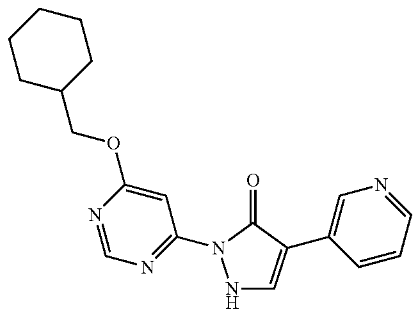 [SMILES: O=c1c(-c2cccnc2)c[nH]n1-c1cc(OCC2CCCCC2)ncn1] | 2% | m/z = 352; 1.92 min |
| 96 | 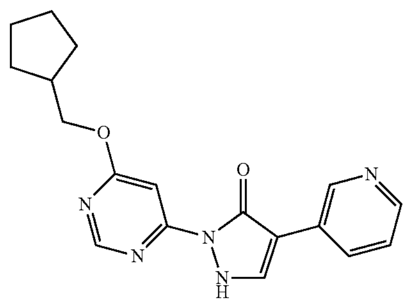 [SMILES: O=c1c(-c2cccnc2)c[nH]n1-c1cc(OCC2CCCC2)ncn1] | 2% | m/z = 338; 1.87 min |
| 97 | 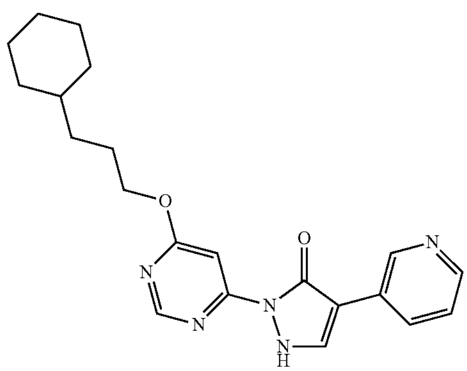 [SMILES: O=c1c(-c2cccnc2)c[nH]n1-c1cc(OCCCC2CCCCC2)ncn1] | 1% | m/z = 380; 2.26 min |
| 98 | 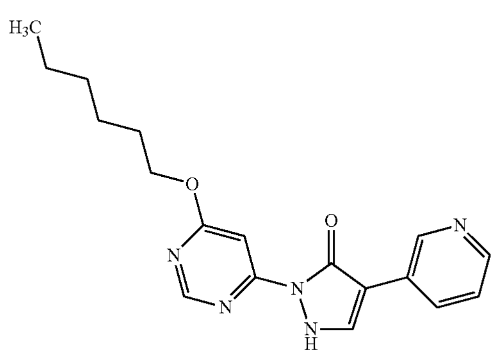 [SMILES: CCCCCCOc1cc(-n2[nH]cc(-c3cccnc3)c2=O)ncn1] | 2% | m/z = 340; 2.01 min |
| 99 | 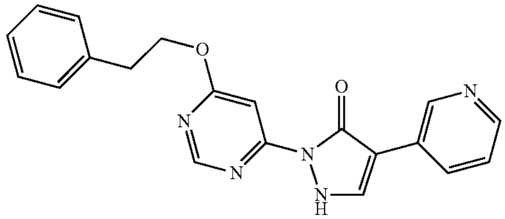 [SMILES: O=c1c(-c2cccnc2)c[nH]n1-c1cc(OCCc2ccccc2)ncn1] | 5% | m/z = 360; 1.73 min |

Example 100

2-{6-[(Azetidin-3-ylmethyl)amino]pyrimidin-4-yl}-4-pyridin-3-yl-1,2-dihydro-3H-pyrazol-3-one dihydrochloride

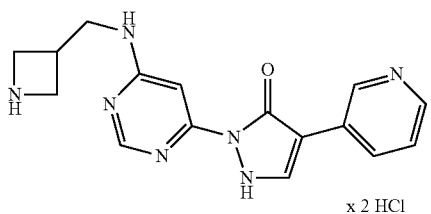 [SMILES: O=c1c(-c2cccnc2)c[nH]n1-c1cc(NCC2CNC2)ncn1]

x 2 HCl

Step a): tert-Butyl 3-({[6-(5-oxo-4-pyridin-3-yl-2,5-dihydro-1H-pyrazol-1-yl)pyrimidin-4-yl]amino}methyl)azetidine-1-carboxylate

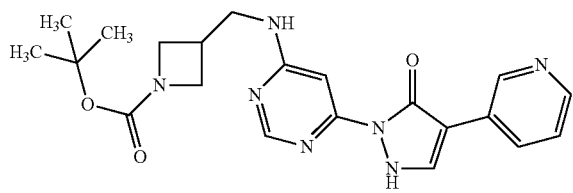 [SMILES: CC(C)(C)OC(=O)N1CC(CNc2cc(-n3[nH]cc(-c4cccnc4)c3=O)ncn2)C1]

300 mg (1.1 mmol) of the compound from Example 23 are initially charged in 6 ml of ethanol. 408 mg (2.2 mmol) of tert-butyl 3-(aminomethyl)azetidine-1-carboxylate are added, and the mixture is reacted initially for 40 min at 120° C. and then for another 40 min at 150° C. in a single-mode microwave oven (CEM Explorer). The solid is then filtered off, washed twice with methanol and discarded, and the wash solutions are combined with the mother liquor. These are concentrated on a rotary evaporator, and the residue is purified by preparative HPLC (RP18 column; mobile phase: acetonitrile/water gradient). The product-containing fractions are combined and concentrated on a rotary evaporator, which gives 354 mg of a residue which, according to LC-MS and $^1$H-NMR, corresponds to the title compound in a purity of about 50% and is reacted further as such.

Step b): 2-{6-[(Azetidin-3-ylmethyl)amino]pyrimidin-4-yl}-4-pyridin-3-yl-1,2-dihydro-3H-pyrazol-3-one dihydrochloride

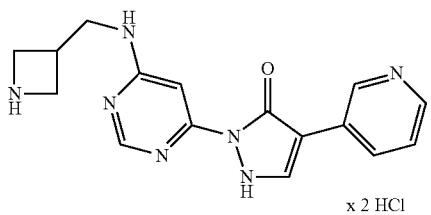 [SMILES: O=c1c(-c2cccnc2)c[nH]n1-c1cc(NCC2CNC2)ncn1]

x 2 HCl 301 mg of the intermediate obtained above are initially charged in 3 ml of dichloromethane, 1.1 ml (14.2 mmol) of TFA are added with stirring at RT and the mixture is stirred at RT for 30 min. The reaction mixture is then diluted with methanol and concentrated on a rotary evaporator. More methanol is added, the mixture is concentrated again, and this procedure is repeated two more times. The residue is then stirred at RT in tert-butyl methyl ether for 30 min, and the solid is filtered off and dried under high vacuum. The residue is then purified by preparative HPLC (RP18 column; mobile phase: acetonitrile/water gradient with 0.1% TFA added to the water). The product-containing fractions are combined and concentrated on a rotary evaporator. The residue is stirred in 4 ml of a 4 N solution of hydrogen chloride in dioxane for 30 min. The solid is filtered off and dried under high vacuum.

Yield: 29 mg (18% of theory)

LC-MS (Method 7): $R_t$=0.21 min; MS (ESIpos): m/z=324 [M+H]$^+$;

$^1$H-NMR (400 MHz, DMSO-d$_6$): δ=10.36 (s, 1H), 9.33 (s, 1H), 8.89 (d, 1H), 8.81 (s, 1H), 8.72 (s, 1H), 8.56 (d, 1H), 8.50 (br. s, 3H), 8.03 (s, 1H), 7.94 (dd, 1H), 4.40 (dd, 1H), 4.30 (dd, 1H), 3.70-3.60 (m, 2H), 3.02-2.92 (m, 2H), 2.75-2.65 (m, 1H).

B. EVALUATION OF THE PHARMACOLOGICAL ACTIVITY

The pharmacological properties of the compounds according to the invention can be demonstrated in the following assays:

Abbreviations

DMEM Dulbecco's modified Eagle medium
FCS fetal calf serum
TMB 3,3',5,5'-tetramethylbenzidine
Tris tris(hydroxymethyl)aminomethane

1. In Vitro Tests for Determination of the Activity and Selectivity of HIF Prolyl 4-hydroxylase Inhibitors 1.a) Inhibition of the Activity of HIF Prolyl Hydroxylase:

Hydroxylated HIF bonds specifically to the von Hippel-Lindau protein-elongin B-elongin C complex (VBC complex). This interaction occurs only if HIF is hydroxylated on a conserved prolyl radical. It is the basis for the biochemical determination of HIF prolyl hydroxylase activity. The test is carried out as described [Oehme F., Jonghaus W., Narouz-Ott L., Huetter J., Flamme I., Anal. Biochem. 330 (1), 74-80 (2004)]:

A clear 96-well microtiter plate coated with NeutrAvidin HBC (Pierce) is incubated with blocker casein for 30 minutes. The plate is then washed three times with 200 µl each time of wash buffer (50 mM Tris, pH 7.5, 100 mM NaCl, 10% (v/v) blocker casein, 0.05% (v/v) Tween 20) per well. The peptide biotin-DLDLEMLAPYIPMDDDFQL (Eurogentec, 4102 Seraing, Belgium) is added in a concentration of 400 nM in 100 µl wash buffer. This peptide serves as a substrate for the prolyl hydroxylation and is bonded to the microtiter plate. After incubation for 60 minutes, the plate is washed three times with wash buffer, incubated with 1 mM biotin in blocker casein for 30 minutes and then washed again three times with wash buffer.

To carry out the prolyl hydroxylase reaction, the peptide substrate bonded to the plate is incubated with a cell lysate containing prolyl hydroxylase for 1 to 60 minutes. The reaction takes place in 100 µl reaction buffer (20 mM Tris, pH 7.5, 5 mM KCl, 1.5 mM MgCl2, 1 µM-1 mM 2-oxoglutarate, 10 µM FeSO4, 2 mM ascorbate) at room temperature. The reaction mixture moreover contains various concentrations of the prolyl hydroxylase inhibitor to be tested. The test substance is preferably, but not exclusively, employed at concentrations of between 1 nM and 100 µM. The reaction is stopped by washing the plate three times with wash buffer.

For quantitative determination of the prolyl hydroxylation, a fusion protein which contains both thioredoxin from *E. coli* and the VBC complex in 80 µl bonding buffer (50 mM Tris, pH 7.5, 120 mM NaCl) is added. After 15 minutes, 10 µl of a solution of polyclonal anti-thioredoxin antibodies from rabbit in bonding buffer are added. After a further 30 minutes, 10 µl of a solution of anti-rabbit immunoglobulin coupled to horseradish peroxidase in bonding buffer are added. After incubation at room temperature for 30 minutes, the plate is washed three times with wash buffer in order to remove non-bonded VBC complex and antibodies. To determine the amount of bonded VBC complex, the plate is incubated with TMB for 15 minutes. The color reaction is ended by addition of 100 µl 1 M sulfuric acid. The amount of bonded VBC complex is determined by measurement of the optical density at 450 nm. It is proportional to the amount of hydroxylated proline in the peptide substrate.

Alternatively, a VBC complex coupled to europium (Perkin Elmer) can be used for detection of the prolyl hydroxylation. In this case, the amount of bonded VBC complex is determined by the fluorescence with respect to time. The use of VBC complex labeled with [$^{35}$S]-methionine is moreover possible. For this, the radioactively labeled VBC complex can be prepared by in vitro transcription-translation in reticulocyte lysate.

The embodiment examples inhibit the activity of HIF prolyl hydroxylase in this test with an $IC_{50}$ value of <30 µM. Representative $IC_{50}$ values for the embodiment examples are reproduced in the following Table 1:

TABLE 1

| Example No. | $IC_{50}$ [µM] |
|---|---|
| 3 | 0.7 |
| 6 | 2.8 |
| 7 | 0.88 |
| 16 | 0.48 |
| 18 | 0.18 |
| 22 | 2.7 |
| 26 | 4.0 |
| 28 | 0.89 |
| 44 | 1.12 |
| 46 | 0.93 |
| 55 | 1.7 |

1.b) Cellular, Functional In Vitro Test:

The activity of the compounds according to the invention is quantified with the aid of a recombinant cell line. The cell is originally derived from a human lung carcinoma cell line (A549, ATCC: American Type Culture Collection, Manassas, Va. 20108, USA). The test cell line is transfected in a stable manner with a vector which contains the reporter gene of *Photinus pyralis* luciferase (called luciferase in the following) under the control of an artificial minimal promoter. The minimal promoter comprises two hypoxia-responsible elements upstream of a TATA box [Oehme F., Ellinghaus P., Kolkhof P., Smith T. J., Ramakrishnan S., Hinter J., Schramm M., Flamme I., *Biochem. Biophys. Res. Commun.* 296 (2), 343-9 (2002)]. Under the effect of hypoxia (for example culturing in the presence of 1% oxygen for 24 hours) or under the action of non-selective dioxygenase inhibitors (for example desferroxamine in a concentration of 100 µM, cobalt chloride in a concentration of 100 µM or N-oxalylglycine diethyl ester in a concentration of 1 mM), the test cell line produces luciferase, which can be detected and quantified with the aid of suitable bioluminescence reagents (for example Steady-Glo® Luciferase Assay System, Promega Corporation, Madison, Wis. 53711, USA) and a suitable luminometer.

Test procedure: On the day before the test, the cells are plated out in an exactly calculated amount of culture medium (DMEM, 10% FCS, 2 mM glutamine) in 384- or 1,536-well microtiter plates and kept in a cell incubator (96% atmospheric humidity, 5% v/v $CO_2$, 37° C.). On the test day, the test substances are added to the culture medium in graduated concentrations. No test substance is added to the cells in batches serving as negative controls. As a positive control for determination of the sensitivity of the cell to inhibitors, desferroxamine for example is added in a final concentration of 100 µM. Six to 24 hours after transfer of the test substances into the wells of the microtiter plates, the resulting light signal is measured in the luminometer. A dose/effect relationship is plotted with the aid of the measurement values, which serves as the basis for determining the half-maximum active concentration (called the $EC_{50}$ value).

1.c) Cellular, Functional In Vitro Test of Modification of the Gene Expression:

To investigate the modification of the expression of specific mRNAs in human cell lines after treatment with test substances, the following cell lines are cultured on 6- or 24-well plates: human hepatoma cells (HUH, JCRB Cell Bank, Japan), human embryonal kidney fibroblasts (HEK/293, ATCC, Manassas, Va. 20108, USA), human cervical carcinoma cells (HeLa, ATCC, Manassas, Va. 20108, USA), human umbilical vein endothelial cells (HUVEC, Cambrex, East Rutherford, N.J. 07073, USA). 24 hours after addition of the test substances, the cells are washed with phosphate-buffered saline and the total RNA is obtained from them using a suitable method (for example Trizol® reagent, Invitrogen GmbH, 76131 Karlsruhe, Germany).

For a typical analysis experiment, 1 µg each of the total RNA obtained in this way is digested with DNase I and translated into a complementary DNA (cDNA) using a suitable reverse transcriptase reaction (ImProm-II Reverse Transcription System, Promega Corporation, Madison, Wis. 53711, USA). 2.5% of the cDNA batch obtained in this way is used in each case for the polymerase chain reaction. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.). The primer-probe combinations used here are generated by means of Primer Express 1.5 Software (Applied Biosystems, Inc.). Specifically, the mRNAs of erythropoietin, carboanhydrase IX, lactate dehydrogenase A and vascular endothelial cell growth factor are investigated.

Substances according to the present invention lead to a significant dose-dependent increase in the mRNA of hypoxia-induced genes in cells of human origin.

2. In Vivo Tests for Detection of the Action in the Cardiovascular System 2.a) In Vivo Test of Modification of Gene Expression:

The test compounds dissolved in suitable solvents are administered to mice or rats either orally by stomach tube administration, intraperitoneally or intravenously. Typical dosages are 0.1, 0.5, 1, 5, 10, 20, 50, 100 and 300 mg substance per kg of body weight and administration. Control animals receive only solvent. 4, 8 or 24 hours after administration of the test substance the animals are sacrificed with an overdose of isoflurane and a subsequent fracture of the neck and the organs to be investigated are removed. Parts of the organs are shock-frozen in liquid nitrogen. Total RNA is obtained from the organ parts as described under B.1.a) and this is translated into a cDNA. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.).

Substances according to the present invention lead to a significant dose-dependent increase in the mRNA of erythropoietin in the kidney after oral or parenteral administration compared with the placebo control.

2.b) Determination of the Erythropoietin Level in Serum:

The test substance in a suitable solvent is administered to mice or rats either intraperitoneally or orally once or twice daily. Typical dosages are 0.1, 0.5, 1, 5, 10, 20, 50, 100 and 300 mg substance per kg of body weight and administration. Placebo control animals receive only solvent. Before the administration and four hours after the last administration of substance, 50 µl of blood are taken from the animals from the retroorbital venous plexus or the tail vein under short anesthesia. The blood is rendered uncoagulable by addition of lithium heparin. The blood plasma is obtained by centrifugation. The content of erythropoietin in the blood plasma is determined with the aid of an erythropoietin-ELISA (Quantikine® mouse Epo Immunoassay, R&D Systems, Inc., Minneapolis, USA) in accordance with the manufacturer's instructions. The measurement values are converted into pg/ml with the aid of a reference measurement ascertained for mouse erythropoietin.

Substances according to the present invention lead to a significant dose-dependent increase in the plasma erythropoietin after oral and parental administration compared with the starting value and the placebo control.

2.c) Determination of the Cell Composition of Peripheral Blood:

The test substance in a suitable solvent is administered to mice or rats either intraperitoneally or orally once or twice daily for several days. Typical dosages are for example 0.1, 0.5, 1, 5, 10, 20, 50, 100 and 300 mg substance per kg of body weight and administration. Control animals receive only solvent. At the end of the study, blood is taken from the animals from the venous plexus of the corner of the eye or the tail vein under short anesthesia and is rendered uncoagulable by addition of sodium citrate. The concentrations of erythrocytes, leukocytes and thrombocytes are determined in the blood samples in a suitable electronic measuring apparatus. The concentration of the reticulocytes is determined by microscope screening of in each case 1000 erythrocytes with the aid of blood smears stained with a stain solution suitable for this purpose (KABE Labortechnik, Nümbrecht). For determination of the hematocrit, blood is taken from the retroorbital venous plexus by means of a hematocrit capillary and the hematocrit value is read off manually after centrifugation of the capillary in a centrifuge suitable for this purpose.

Substances according to the present invention lead to a significant dose-dependent increase in the hematocrit, the erythrocyte count and the reticulocytes after oral and parenteral administration compared with the starting value and the placebo control.

C. EMBODIMENT EXAMPLES FOR PHARMACEUTICAL COMPOSITIONS

The compounds according to the invention can be converted into pharmaceutical formulations as follows:

Tablet:
Composition:

100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm

Preparation:

The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:
Composition:

1000 mg of the compound according to the invention, 1000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.

Preparation:

The Rhodigel is suspended in ethanol and the compound according to the invention is added to the suspension. The water is added with stirring. The mixture is stirred for approx. 6 h until swelling of the Rhodigel has ended.

Solution for Oral Administration:
Composition:

500 mg of the compound according to the invention, 2.5 g polysorbate and 97 g polyethylene glycol 400.20 g of oral solution correspond to an individual dose of 100 mg of the compound according to the invention.

Preparation:

The compound according to the invention is suspended in the mixture of polyethylene glycol and polysorbate, while stirring. The stirring operation is continued until solution of the compound according to the invention is complete.

i.v. Solution:

The compound according to the invention is dissolved in a concentration below the saturation solubility in a physiologically acceptable solvent (for example isotonic saline solution, glucose solution 5% and/or PEG 400 solution 30%). The solution is subjected to sterile filtration and is transferred into sterile and pyrogen-free injection containers.

The invention claimed is:

1. A compound of the formula (I)

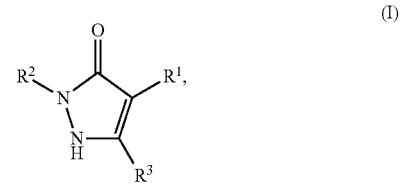

in which

R¹ represents a heteroaryl group of the formula

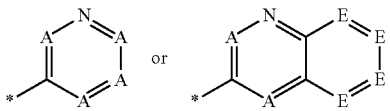

where
* represents the point of attachment to the dihydropyrazolone ring,
A in each individual occurrence represents C—R⁴ or N, where at most two ring members A represent N at the same time,
and
E in each individual occurrence represents C—R⁵ or N, where at most two ring members E represent N at the same time, R² represents a heteroaryl group of the formula

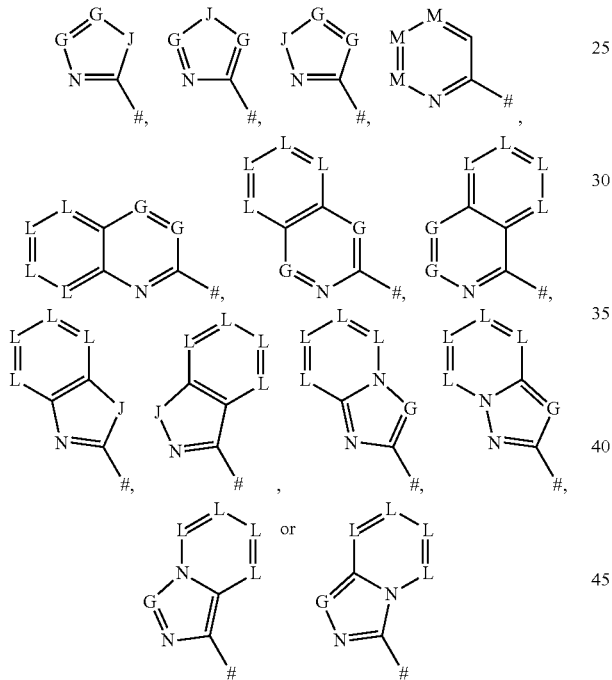

where
# represents the point of attachment to the dihydropyrazolone ring,
G in each individual occurrence represents C—R⁶ or N,
J represents O, S or N—R⁷,
L in each individual occurrence represents C—R⁸ or N, where at most two ring members L represent N at the same time,
and
M in each individual occurrence represents C—R⁹ or N, where in total one or two ring members M represent N,
where
R⁴, R⁶, R⁸ and R⁹ are identical or different and in each individual case independently of one another represent hydrogen or a substituent selected from the group consisting of halogen, cyano, nitro, $(C_1-C_6)$-alkyl, $(C_3-C_7)$-cycloalkyl, 4- to 10-membered heterocycloalkyl, phenyl, 5- or 6-membered heteroaryl, —C(=O)—R¹⁰, —C(=O)—OR¹¹, —C(=O)—NR¹²R¹³, —O—C(=O)—R¹⁴, —O—C(=O)—NR¹⁵R¹⁶, —NR¹⁷—C(=O)—R¹⁸, —NR¹⁹—C(=O)—OR²⁰, —NR²¹—C(=O)—NR²²R²³, —NR²⁴—SO₂—R²⁵, —SO₂—R²⁶, —SO₂—NR²⁷R²⁸, —OR²⁹, —SR³⁰ and —NR³¹R³², where (i) $(C_1-C_6)$-alkyl for its part may be mono- to trisubstituted by identical or different radicals selected from the group consisting of halogen, cyano, oxo, $(C_3-C_7)$-cycloalkyl, 4- to 10-membered heterocycloalkyl, phenyl, 5- or 6-membered heteroaryl, —C(=O)—R¹⁰, —C(=O)—OR¹¹, —C(=O)—NR¹²R¹³, —O—C(=O)—R¹⁴, —O—C(=O)—NR¹⁵R¹⁶, —NR¹⁷—C(=O)—R¹⁸, —NR¹⁹—C(=O)—OR²⁰, —NR²¹—C(=O)—NR²²R²³, —NR²⁴—SO₂—R²⁵, —SO₂—R²⁶, —SO₂—NR²⁷R²⁸, —OR²⁹, —SR³⁰ and —NR³¹R³², where the last-mentioned cycloalkyl, heterocycloalkyl, phenyl and heteroaryl radicals for their part may in each case be substituted up to three times by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, (ii) $(C_3-C_7)$-cycloalkyl, 4- to 10-membered heterocycloalkyl, phenyl and 5- or 6-membered heteroaryl for their part may in each case be mono- to trisubstituted by identical or different radicals selected from the group consisting of $(C_1-C_6)$-alkyl, $(C_3-C_7)$-cycloalkyl, halogen, cyano, oxo, —C(=O)—R¹⁰, —C(=O)—OR¹¹, —C(=O)—NR¹²R¹³, —O—C(=O)—R¹⁴, —O—C(=O)—NR¹⁵R¹⁶, —NR¹⁷—C(=O)—R¹⁸, —NR¹⁹—C(=O)—OR²⁰, —NR²¹—C(=O)—NR²²R²³, —NR²⁴—SO₂—R²⁵, —SO₂—R²⁶, —SO₂—NR²⁷R²⁸, —OR²⁹, —SR³⁰ and —NR³¹R³², where the last-mentioned alkyl radical for its part may be substituted up to three times by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl, (iii) R¹⁰, R¹¹, R¹², R¹⁴, R¹⁵, R¹⁸, R²⁰, R²², R²⁵, R²⁶, R²⁷, R²⁹, R³⁰ and R³¹ independently of one another in each individual occurrence represent a radical selected from the group consisting of hydrogen, $(C_1-C_6)$-alkyl, $(C_3-C_7)$-cycloalkyl, 4- to 7-membered heterocycloalkyl, phenyl and 5- or 6-membered heteroaryl, where $(C_3-C_7)$-cycloalkyl, 4- to 7-membered heterocycloalkyl, phenyl and 5- or 6-membered heteroaryl for their part may in each case be substituted up to three times by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl
and
$(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl,
where the last-mentioned heterocycloalkyl radical for its part may be substituted up to two times by identical or different substituents from the group consisting of $(C_1-C_4)$-alkyl, (iv) $R^{13}$, $R^{16}$, $R^{17}$, $R^{19}$, $R^{21}$, $R^{23}$, $R^{24}$, $R^{28}$ and $R^{32}$ independently of one another in each individual occurrence represent a radical selected from the group consisting of hydrogen and $(C_1-C_6)$-alkyl, where $(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and $(C_1-C_4)$-alkoxycarbonyl, and/or where (v) $R^{12}$ and $R^{13}$, $R^{15}$ and $R^{16}$, $R^{17}$ and $R^{18}$, $R^{19}$ and $R^{20}$, $R^{21}$ and $R^{22}$, $R^{22}$ and $R^{23}$, $R^{24}$ and $R^{25}$, $R^{27}$ and $R^{28}$ and also $R^{31}$ and $R^{32}$ in each case as a pair together with the atoms to which they are attached may form a 5- or 6-membered heterocycloalkyl ring which may be mono- to trisubstituted by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, $R^5$ in each individual case, independently of one another, represents hydrogen or a substituent selected from the group consisting of halogen, cyano, nitro, $(C_1-C_6)$-alkyl, trifluoromethyl, hydroxyl, $(C_1-C_6)$-alkoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl
and
$R^7$ represents hydrogen or a substituent selected from the group consisting of $(C_1-C_6)$-alkyl, $(C_3-C_7)$-cycloalkyl, 4- to 7-membered heterocycloalkyl, phenyl and 5- or 6-membered heteroaryl, where
(i) $(C_1-C_6)$-alkyl for its part may be mono- to trisubstituted by identical or different radicals selected from the group consisting of halogen, cyano, oxo, $(C_3-C_7)$-cycloalkyl, 4- to 7-membered heterocycloalkyl, phenyl, 5- or 6-membered heteroaryl, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$, where the last-mentioned cycloalkyl, heterocycloalkyl, phenyl and heteroaryl radicals for their part may in each case be substituted up to three times by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl,
and
(ii) $(C_3-C_7)$-cycloalkyl, 4- to 7-membered heterocycloalkyl, phenyl and 5- or 6-membered heteroaryl for their part may in each case be mono- to trisubstituted by identical or different radicals selected from the group consisting of $(C_1-C_6)$-alkyl, halogen, cyano, oxo, —C(=O)—$R^{10}$, —C(=O)—$OR^{11}$, —C(=O)—$NR^{12}R^{13}$, —O—C(=O)—$R^{14}$, —O—C(=O)—$NR^{15}R^{16}$, —$NR^{17}$—C(=O)—$R^{18}$, —$NR^{19}$—C(=O)—$OR^{20}$, —$NR^{21}$—C(=O)—$NR^{22}R^{23}$, —$NR^{24}$—$SO_2$—$R^{25}$, —$SO_2$—$R^{26}$, —$SO_2$—$NR^{27}R^{28}$, —$OR^{29}$, —$SR^{30}$ and —$NR^{31}R^{32}$,
where the last-mentioned alkyl radical for its part may be substituted up to three times by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl,
where
(a) $R^{10}$, $R^{11}$, $R^{12}$, $R^{14}$, $R^{15}$, $R^{18}$, $R^{20}$, $R^{22}$, $R^{25}$, $R^{26}$, $R^{27}$, $R^{29}$, $R^{30}$ and $R^{31}$ independently of one another in each individual occurrence represent a radical selected from the group consisting of hydrogen, $(C_1-C_6)$-alkyl, $(C_3-C_7)$-cycloalkyl, 4- to 7-membered heterocycloalkyl, phenyl and 5- or 6-membered heteroaryl, where
$(C_3-C_7)$-cycloalkyl, 4- to 7-membered heterocycloalkyl, phenyl and 5- or 6-membered heteroaryl for their part may in each case be substituted up to three times by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl
and
$(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, $(C_3-C_7)$-cycloalkyl, 4- to 7-membered heterocycloalkyl, phenyl and 5- or 6-membered heteroaryl,
(b) $R^{13}$, $R^{16}$, $R^{17}$, $R^{19}$, $R^{21}$, $R^{23}$, $R^{24}$, $R^{28}$ and $R^{32}$ independently of one another in each individual occurrence represent a radical selected from the group consisting of hydrogen and $(C_1-C_6)$-alkyl, where $(C_1-C_6)$-alkyl may be mono- to trisubstituted by identical or different substituents from the group consisting of halogen, cyano, hydroxyl, trifluoromethoxy, (C₁-C₄)-alkoxy, amino, mono-(C₁-C₄)-alkylamino, di-(C₁-C₄)-alkylamino, hydroxycarbonyl and (C₁-C₄)-alkoxycarbonyl, and/or (c) $R^{12}$ and $R^{13}$, $R^{15}$ and $R^{16}$, $R^{17}$ and $R^{18}$, $R^{19}$ and $R^{20}$, $R^{21}$ and $R^{22}$, $R^{22}$ and $R^{23}$, $R^{24}$ and $R^{25}$, $R^{27}$ and $R^{28}$ and also $R^{31}$ and $R^{32}$ in each case as a pair together with the atoms to which they are attached may form a 5- or 6-membered heterocycloalkyl ring which may be mono- to trisubstituted by identical or different substituents from the group consisting of halogen, cyano, (C₁-C₄)-alkyl, trifluoromethyl, hydroxyl, (C₁-C₄)-alkoxy, trifluoromethoxy, oxo, amino, mono-(C₁-C₄)-alkylamino, di-(C₁-C₄)-alkylamino, hydroxycarbonyl and (C₁-C₄)-alkoxycarbonyl, and $R^3$ represents hydrogen, (C₁-C₆)-alkyl or (C₃-C₇)-cycloalkyl, and salts, solvates and solvates of the salts thereof.

2. The compound of claim 1 in which $R^1$ represents a heteroaryl group of the formula

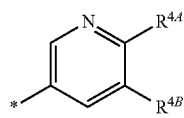

where

* represents the point of attachment to the dihydropyrazolone ring and $R^{4A}$ and $R^{4B}$ are identical or different and independently of one another represent hydrogen or a substituent selected from the group consisting of fluorine, chlorine, bromine, cyano, (C₁-C₆)-alkyl, hydroxyl, (C₁-C₆)-alkoxy, trifluoromethoxy, amino, mono-(C₁-C₆)-alkylamino, di-(C₁-C₆)-alkylamino, hydroxycarbonyl and (C₁-C₆)-alkoxycarbonyl, where the (C₁-C₆)-alkyl radical mentioned for its part may be substituted up to three times by identical or different substituents from the group consisting of fluorine, chlorine, bromine, cyano, hydroxyl, trifluoromethoxy, (C₁-C₄)-alkoxy, amino, mono-(C₁-C₄)-alkylamino, di-(C₁-C₄)-alkylamino, hydroxycarbonyl and (C₁-C₄)-alkoxycarbonyl, $R^2$ represents a heteroaryl group of the formula

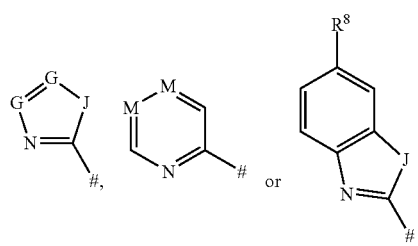

where

\# represents the point of attachment to the dihydropyrazolone ring,

G represents in each case C—$R^6$ or N, where not more than one of the two ring members G represents N, J represents O or S, M represents in each case C—$R^9$ or N, where one of the two ring members M represents N and the other represents C—$R^9$, where $R^6$ and $R^9$ in each individual case independently of one another represent hydrogen or a substituent selected from the group consisting of fluorine, chlorine, bromine, cyano, (C₁-C₆)-alkyl, (C₃-C₆)-cycloalkyl, 4- to 6-membered heterocycloalkyl, phenyl, 5- or 6-membered heteroaryl, —C(=O)—OR¹¹, —C(=O)—NR¹²R¹³, —O—C(=O)—R¹⁴, —O—C(=O)—NR¹⁵R¹⁶, —NR¹⁷—C(=O)—R¹⁸, —NR¹⁹—C(=O)—OR²⁰, —NR²¹—C(=O)—NR²²R²³, —NR²⁴—SO₂—R²⁵, —OR²⁹ and —NR³¹R³², where (i) (C₁-C₆)-alkyl for its part may be mono- to trisubstituted by identical or different radicals selected from the group consisting of fluorine, chlorine, bromine, cyano, (C₃-C₆)-cycloalkyl, 4- to 6-membered heterocycloalkyl, phenyl, 5- or 6-membered heteroaryl, —C(=O)—OR¹¹, —C(=O)—NR¹²R¹³, —O—C(=O)—R¹⁴, —O—C(=O)—NR¹⁵R¹⁶, —NR¹⁷—C(=O)—R¹⁸, —NR¹⁹—C(=O)—OR²⁰, —NR²¹—C(=O)—NR²²R²³, —NR²⁴—SO₂—R²⁵, —OR²⁹ and —NR³¹R³², where the last-mentioned cycloalkyl, heterocycloalkyl, phenyl and heteroaryl radicals for their part may in each case be substituted up to two times by identical or different substituents from the group consisting of fluorine, chlorine, bromine, cyano, (C₁-C₄)-alkyl, trifluoromethyl, hydroxyl, (C₁-C₄)-alkoxy, trifluoromethoxy, oxo, amino, mono-(C₁-C₄)-alkylamino, di-(C₁-C₄)-alkylamino, hydroxycarbonyl and (C₁-C₄)-alkoxycarbonyl, (ii) (C₃-C₆)-cycloalkyl, 4- to 6-membered heterocycloalkyl, phenyl and 5- or 6-membered heteroaryl for their part may in each case be mono- or disubstituted by identical or different substituents from the group consisting of fluorine, chlorine, bromine, cyano, (C₁-C₄)-alkyl, trifluoromethyl, hydroxyl, (C₁-C₄)-alkoxy, trifluoromethoxy, oxo, amino, mono-(C₁-C₄)-alkylamino, di-(C₁-C₄)-alkylamino, hydroxycarbonyl and (C₁-C₄)-alkoxycarbonyl, (iii) $R^{11}$, $R^{12}$, $R^{14}$, $R^{15}$, $R^{18}$, $R^{20}$, $R^{22}$, $R^{25}$, $R^{29}$ and $R^{31}$ independently of one another in each individual occurrence represent a radical selected from the group consisting of hydrogen, (C₁-C₆)-alkyl, (C₃-C₆)-cycloalkyl, 4- to 6-membered heterocycloalkyl, phenyl and 5- or 6-membered heteroaryl, where (C₃-C₆)-cycloalkyl, 4- to 6-membered heterocycloalkyl, phenyl and 5- or 6-membered heteroaryl for their part may in each case be substituted up to three times by identical or different substituents from the group consisting of fluorine, chlorine, bromine, cyano, (C₁-C₄)-alkyl, trifluoromethyl, hydroxyl, (C₁-C₄)-alkoxy, trifluoromethoxy, oxo, amino, mono-(C₁-C₄)-alkylamino, di-($C_1$-$C_4$)-alkylamino, hydroxycarbonyl and ($C_1$-$C_4$)-alkoxycarbonyl
and
($C_1$-$C_6$)-alkyl may be mono- to trisubstituted by identical or different substituents from the group consisting of fluorine, chlorine, bromine, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and 5- or 6-membered heteroaryl, (iv) $R^{13}$, $R^{16}$, $R^{17}$, $R^{19}$, $R^{21}$, $R^{23}$, $R^{24}$ and $R^{32}$ independently of one another in each individual occurrence represent a radical selected from the group consisting of hydrogen and ($C_1$-$C_6$)-alkyl, where ($C_1$-$C_6$)-alkyl may be mono- or disubstituted by identical or different substituents from the group consisting of fluorine, chlorine, bromine, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl, and/or where (v) $R^{12}$ and $R^{13}$, $R^{15}$ and $R^{16}$, $R^{17}$ and $R^{18}$, $R^{19}$ and $R^{20}$, $R^{21}$ and $R^{22}$, $R^{22}$ and $R^{23}$, $R^{24}$ and $R^{25}$ and also $R^{31}$ and $R^{32}$ in each case as a pair together with the atoms to which they are attached may form a 5- or 6-membered heterocycloalkyl ring which may be mono- or disubstituted by identical or different substituents from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, and
$R^8$ represents hydrogen or a substituent selected from the group consisting of fluorine, chlorine, bromine, cyano, ($C_1$-$C_6$)-alkyl, hydroxyl, ($C_1$-$C_6$)-alkoxy, trifluoromethoxy, amino, mono-($C_1$-$C_6$)-alkylamino, di-($C_1$-$C_6$)-alkylamino, hydroxycarbonyl and ($C_1$-$C_6$)-alkoxycarbonyl,
and
$R^3$ represents hydrogen or methyl,
and salts, solvates and solvates of the salts thereof.

3. The compound of claim 1 in which
$R^1$ represents a heteroaryl group of the formula

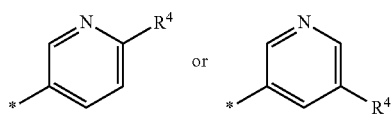

where
* represents the point of attachment to the dihydropyrazolone ring
and
$R^4$ represents hydrogen, fluorine, chlorine, bromine, cyano, ($C_1$-$C_4$)-alkyl, trifluoromethyl, hydroxymethyl, ($C_1$-$C_4$)-alkoxy, trifluoromethoxy, hydroxycarbonyl or ($C_1$-$C_4$)-alkoxycarbonyl, $R^2$ represents a heteroaryl group of the formula

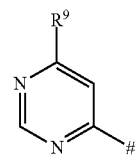

where
# represents the point of attachment to the dihydropyrazolone ring
and
$R^9$ represents hydrogen, fluorine, chlorine, bromine, cyano, ($C_1$-$C_4$)-alkyl, trifluoromethyl, hydroxyl, ($C_1$-$C_4$)-alkoxy, trifluoromethoxy, amino, mono-($C_1$-$C_4$)-alkylamino, di-($C_1$-$C_4$)-alkylamino, hydroxycarbonyl, ($C_1$-$C_4$)-alkoxycarbonyl, 4- to 6-membered heterocycloalkyl, phenyl or 5- or 6-membered heteroaryl, where
($C_1$-$C_4$)-alkyl for its part may be substituted by hydroxyl, ($C_1$-$C_4$)-alkoxy or amino
and
4- to 6-membered heterocycloalkyl, phenyl and 5- or 6-membered heteroaryl for their part may in each case be mono- or disubstituted by identical or different substituents from the group consisting of fluorine, chlorine, bromine, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, and
$R^3$ represents hydrogen,
and salts, solvates and solvates of the salts thereof.

4. The compound of claim 1 in which
$R^1$ represents a heteroaryl group of the formula

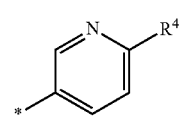

where
* represents the point of attachment to the dihydropyrazolone ring
and
$R^4$ represents hydrogen, fluorine, chlorine, bromine, cyano, ($C_1$-$C_4$)-alkyl, trifluoromethyl, hydroxymethyl, ($C_1$-$C_4$)-alkoxy, trifluoromethoxy, hydroxycarbonyl or ($C_1$-$C_4$)-alkoxycarbonyl, $R^2$ represents a heteroaryl group of the formula

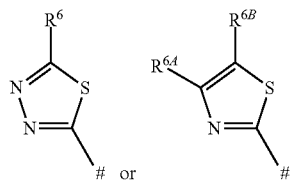

where
# represents the point of attachment to the dihydropyrazolone ring
and
$R^6$, $R^{6A}$ and $R^{6B}$ are identical or different and independently of one another represent hydrogen or a substituent selected from the group consisting of fluorine, chlorine, bromine, cyano, $(C_1\text{-}C_4)$-alkyl, trifluoromethyl, hydroxyl, $(C_1\text{-}C_4)$-alkoxy, trifluoromethoxy, amino, mono-$(C_1\text{-}C_4)$-alkylamino, di-$(C_1\text{-}C_4)$-alkylamino, hydroxycarbonyl, $(C_1\text{-}C_4)$-alkoxycarbonyl, 4- to 6-membered heterocycloalkyl, phenyl and 5- or 6-membered heteroaryl, where
$(C_1\text{-}C_4)$-alkyl for its part may be substituted by hydroxyl, $(C_1\text{-}C_4)$-alkoxy or amino
and
4- to 6-membered heterocycloalkyl, phenyl and 5- or 6-membered heteroaryl for their part may in each case be mono- or disubstituted by identical or different substituents from the group consisting of fluorine, chlorine, bromine, cyano, $(C_1\text{-}C_4)$-alkyl, trifluoromethyl, hydroxyl, $(C_1\text{-}C_4)$-alkoxy, trifluoromethoxy, oxo, amino, mono-$(C_1\text{-}C_4)$-alkylamino, di-$(C_1\text{-}C_4)$-alkylamino, hydroxycarbonyl and $(C_1\text{-}C_4)$-alkoxycarbonyl,
and
$R^3$ represents hydrogen,
and salts, solvates and solvates of the salts thereof.

5. A method of making a compound of the formula (I) as defined in claim 1, characterized in that a compound of the formula (II)

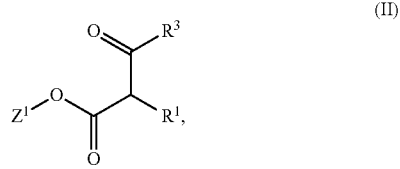

in which $R^1$ and $R^3$ have the meanings given in claim 1 and $Z^1$ represents methyl or ethyl,
is reacted in an inert solvent, if appropriate in the presence of an acid, with a compound of the formula (III)

in which $R^2$ has the meaning given in claim 1,
to give compounds of the formula (IV)

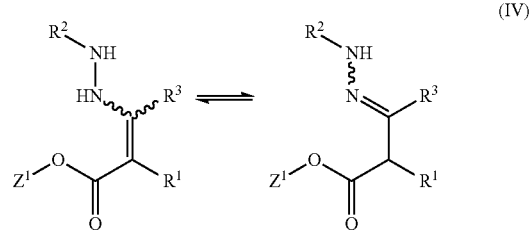

in which $Z^1$, $R^1$, $R^2$ and $R^3$ have the meanings given above, which, already under these reaction conditions or in a subsequent reaction step under the action of a base, cyclize to the compounds of the formula (I), and the compounds of the formula (I) are, if appropriate with the appropriate (i) solvents and/or (ii) bases or acids, converted into their solvates, salts and/or solvates of the salts.

6. A process for the preparation of a compound of the formula (I) as defined in claim 1 in which $R^3$ represents hydrogen, comprising:
condensing a compound of the formula (V)

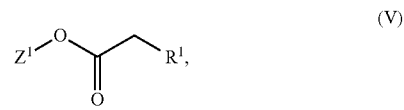

in which $R^1$ has the meaning given in claim 1 and
$Z^1$ represents methyl or ethyl,
with a compound of the formula (VI)

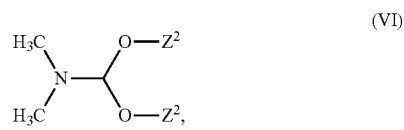

in which
$Z^2$ represents methyl or ethyl,
to give compounds of the formula (VII)

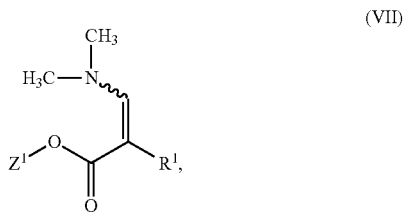

in which $Z^1$ and $R^1$ have the meanings given above, reacting the compound of formula (VII) in the presence of an acid with a compound of the formula (III)

in which $R^2$ has the meaning given in claim 1,
to give compounds of the formula (IV-A)

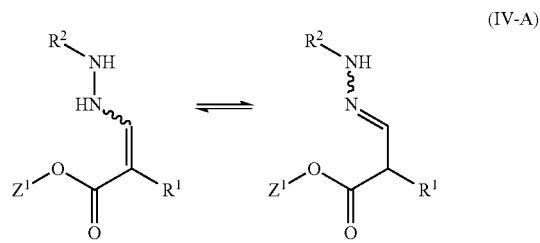

in which $Z^1$, $R^1$ and $R^2$ have the meanings given above, which, already under these reaction conditions or in a subsequent reaction step under the action of a base, cyclize to the compounds of the formula (I) in which $R^3$ represents hydrogen.

7. A pharmaceutical composition comprising the compound of claim 1 in combination with an inert, non-toxic, pharmaceutically suitable auxiliary.

8. A pharmaceutical composition comprising the compound of claim 1 and at least one active compound selected from the group consisting of an ACE inhibitor, an angiotensin II receptor antagonist, a beta receptor blocker, a calcium antagonist, a PDE inhibitor, a mineralocorticoid receptor antagonist, a diuretic, an aspirin, an iron supplement, a vitamin B12 and folic acid supplement, a statin, a digitalis (digoxin) derivative, a tumor chemotherapeutic, and an antibiotic.

9. A method for the treatment of anemia, chronic kidney disease, renal insufficiency, coronary heart disease, angina pectoris, myocardial infarction, arteriosclerosis, pulmonary hypertension, malignant hypertension, and peripheral arterial occlusive disease, comprising administering an effective amount of at least one compound of claim 1, to a human or animal in need thereof.

10. A method for the treatment of anemia, chronic kidney disease, renal insufficiency, coronary heart disease, angina pectoris, myocardial infarction, arteriosclerosis, pulmonary hypertension, malignant hypertension, and peripheral arterial occlusive disease, comprising administering an effective amount of the pharmaceutical composition of claim 7, to a human or animal in need thereof.

* * * * *